United States Patent
Van Almsick et al.

(10) Patent No.: US 8,957,096 B2
(45) Date of Patent: Feb. 17, 2015

(54) HERBICIDALLY ACTIVE OXIME-ETHER-SUBSTITUTED BENZOYLAMIDES

(71) Applicant: Bayer Intellectual Property GmbH, Monheim (DE)

(72) Inventors: Andreas Van Almsick, Karben (DE); Hartmut Ahrens, Egelsbach (DE); Hansjörg Dietrich, Liederbach am Taunus (DE); Isolde Häuser-Hahn, Leverkusen (DE); Ines Heinemann, Hofheim (DE); Elmar Gatzweiler, Bad Nauheim (DE); Christopher Rosinger, Hofheim (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/355,754

(22) PCT Filed: Oct. 29, 2012

(86) PCT No.: PCT/EP2012/071384
§ 371 (c)(1),
(2) Date: May 1, 2014

(87) PCT Pub. No.: WO2013/064459
PCT Pub. Date: May 10, 2013

(65) Prior Publication Data
US 2014/0309112 A1    Oct. 16, 2014

(30) Foreign Application Priority Data
Nov. 3, 2011  (EP) ..................................... 11187666

(51) Int. Cl.
| | | |
|---|---|---|
| *A01N 43/713* | (2006.01) | |
| *A01N 43/653* | (2006.01) | |
| *A01N 43/832* | (2006.01) | |
| *A01N 43/824* | (2006.01) | |
| *C07D 271/08* | (2006.01) | |
| *C07D 271/113* | (2006.01) | |
| *C07D 249/14* | (2006.01) | |
| *C07D 257/06* | (2006.01) | |
| *A01N 43/82* | (2006.01) | |

(52) U.S. Cl.
CPC ............ *A01N 43/713* (2013.01); *A01N 43/653* (2013.01); *A01N 43/82* (2013.01); *C07D 271/113* (2013.01); *C07D 249/14* (2013.01); *C07D 271/08* (2013.01); *C07D 257/06* (2013.01)

USPC ........... 514/364; 514/381; 514/383; 548/251; 548/143; 548/125; 548/265.4

(58) Field of Classification Search
CPC ... A01N 43/713; A01N 43/653; A01N 43/82; C07D 271/08; C07D 271/113; C07D 249/14; C07D 257/06
USPC .......... 514/381, 383, 364; 548/251, 143, 125, 548/265.4
See application file for complete search history.

(56) References Cited

U.S. PATENT DOCUMENTS

| | | | |
|---|---|---|---|
| 8,288,316 B2 | 10/2012 | Kohn et al. | |
| 2011/0152084 A1 | 6/2011 | Kohn et al. | |

FOREIGN PATENT DOCUMENTS

| | | | |
|---|---|---|---|
| DE | 224203 A1 | 7/1985 | |
| DE | 19700019 A1 | 7/1998 | |
| DE | 19700096 A1 | 7/1998 | |
| EP | 0049071 A1 | 4/1982 | |
| EP | 0173657 A2 | 3/1986 | |
| FR | 2407208 A1 | 5/1979 | |
| GB | 1588242 A | * | 4/1981 |
| JP | 11043480 A | 2/1999 | |
| WO | 2004101532 A1 | 11/2004 | |
| WO | 2007115403 A1 | 10/2007 | |
| WO | 2011035874 A1 | 3/2011 | |

OTHER PUBLICATIONS

International Search Report received in PCT/EP2012/071384 mailed Jan. 18, 2013.

* cited by examiner

*Primary Examiner* — Joseph Kosack
*Assistant Examiner* — Matthew Coughlin
(74) *Attorney, Agent, or Firm* — Miles and Stockbridge

(57) ABSTRACT

What is described are oxime ether-substituted benzoylamides of the general formula (I) as herbicides.

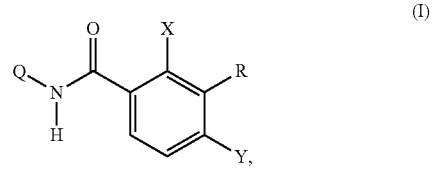

In this formula (I), R, Y and Y are radicals such as hydrogen, organic radicals such as alkyl, and other radicals such as halogen. Q is a tetrazolyl, triazolyl or oxadiazolyl radical.

10 Claims, No Drawings

HERBICIDALLY ACTIVE OXIME-ETHER-SUBSTITUTED BENZOYLAMIDES

CROSS REFERENCE TO RELATED APPLICATIONS

This application is a §371 National Stage Application of PCT/EP2012/071384, filed Oct. 29, 2012 which claims priority to EP 11187666.0, filed Nov. 3, 2011.

BACKGROUND

1. Field of the Invention

The invention relates to the technical field of herbicides, especially that of herbicides for selective control of broad-leaved weeds and weed grasses in crops of useful plants.

2. Description of Related Art

WO2003/010143 and WO2003/010153 disclose N-(tetrazol-5-yl)- and N-(triazol-5-yl)benzamides and their pharmacological action. N-(1,2,5-Oxadiazol-3-yl)benzamides as herbicides are known from WO 2011/035874 A1. EP101748937, of earlier priority but not published before the priority date of the present application, discloses certain N-(tetrazol-5-yl)- and N-(triazol-5-yl)benzamides and -nicotinamides as herbicides.

However, the herbicidal activity and/or the crop plant compatibility of the compounds mentioned in these publications is not always sufficient.

SUMMARY

It is an object of the present invention to provide herbicidally active compounds with improved properties compared to those of the compounds disclosed in the prior art.

It has now been found that benzoylamides substituted in the 3-position of the phenyl ring by certain oxime ether radicals are particularly suitable as herbicides.

Accordingly, the present invention provides benzoylamides of the formula (I) or salts thereof

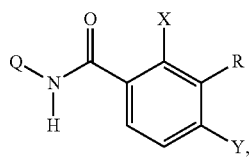

(I)

in which the substituents have the meanings given below:
Q is a Q1, Q2, Q3 or Q4 radical,

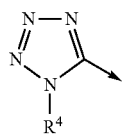

(Q1)

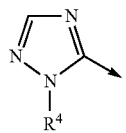

(Q2)

(Q3)

(Q4)

R is —CH=N—OR$^1$, —CH$_2$—O—N=CR$^2$R$^3$,

X is nitro, halogen, cyano, formyl, thiocyanato, ($C_1$-$C_6$)-alkyl, halo-($C_1$-$C_6$)-alkyl, ($C_2$-$C_6$)-alkenyl, halo-($C_2$-$C_6$)-alkenyl, ($C_2$-$C_6$)-alkynyl, halo-($C_2$-$C_6$)-alkynyl, ($C_3$-$C_6$)-cycloalkyl, halo-($C_3$-$C_6$)-cycloalkyl, ($C_3$-$C_6$)-cycloalkyl-($C_1$-$C_6$)-alkyl, halo-($C_3$-$C_6$)-cycloalkyl-($C_1$-$C_6$)-alkyl, COR$^7$, COOR$^7$, OCOOR$^8$, NR$^7$COOR$^8$, C(O)N(R$^7$)$_2$, NR$^7$C(O)N(R$^7$)$_2$, OC(O)N(R$^7$)$_2$, C(O)NR$^7$OR$^7$, OR$^7$, OCOR$^7$, OSO$_2$R$^8$, S(O)$_n$R$^8$, SO$_2$OR$^7$, SO$_2$N(R$^7$)$_2$, NR$^7$SO$_2$R$^8$, NR$^7$OR$^7$, ($C_1$-$C_6$)-alkyl-S(O)$_n$R$^8$, ($C_1$-$C_6$)-alkyl-OR$^7$, ($C_1$-$C_6$)-alkyl-OCOR$^7$, ($C_1$-$C_6$)-alkyl-OSO$_2$R$^8$, ($C_1$-$C_6$)-alkyl-CO$_2$R$^7$, ($C_1$-$C_6$)-alkyl-SO$_2$OR$^8$, ($C_1$-$C_6$)-alkyl-CON(R$^7$)$_2$, ($C_1$-$C_6$)-alkyl-SO$_2$N(R$^7$)$_2$, ($C_1$-$C_6$)-alkyl-NR$^7$COR$^7$, ($C_1$-$C_6$)-alkyl-NR$^7$SO$_2$R$^8$, N(R$^7$)$_2$, P(O)(OR$^9$)$_2$, CH$_2$P(O)(OR$^9$)$_2$, heteroaryl, heterocyclyl, phenyl, ($C_1$-$C_6$)-alkyl-heteroaryl or ($C_1$-$C_6$)-alkyl-heterocyclyl, where the five last-mentioned radicals are each substituted by s radicals from the group consisting of halogen, nitro, cyano, ($C_1$-$C_6$)-alkyl, halo-($C_1$-$C_6$)-alkyl, S(O)$_n$-($C_1$-$C_6$)-alkyl, ($C_1$-$C_6$)-alkoxy and halo-($C_1$-$C_6$)-alkoxy, and where heterocyclyl carries n oxo groups, Y is nitro, halogen, cyano, formyl, thiocyanato, ($C_1$-$C_6$)-alkyl, halo-($C_1$-$C_6$)-alkyl, ($C_2$-$C_6$)-alkenyl, halo-($C_2$-$C_6$)-alkenyl, ($C_2$-$C_6$)-alkynyl, halo-($C_2$-$C_6$)-alkynyl, ($C_3$-$C_6$)-cycloalkyl, halo-($C_3$-$C_6$)-cycloalkyl, ($C_3$-$C_6$)-cycloalkyl-($C_1$-$C_6$)-alkyl, halo-($C_3$-$C_6$)-cycloalkyl-($C_1$-$C_6$)-alkyl, COR$^7$, COOR$^7$, OCOOR$^8$, NR$^1$COOR$^8$, C(O)N(R$^7$)$_2$, NR$^7$C(O)N(R$^7$)$_2$, OC(O)N(R$^7$)$_2$, C(O)NR$^7$OR$^7$, OR$^7$, OSO$_2$R$^8$, S(O)$_n$R$^8$, SO$_2$OR$^8$, SO$_2$N(R$^7$)$_2$, NR$^7$SO$_2$R$^8$, NR$^7$COR$^7$, ($C_1$-$C_6$)-alkyl-S(O)$_n$R$^8$, ($C_1$-$C_6$)-alkyl-OR$^7$, ($C_1$-$C_6$)-alkyl-OCOR$^7$, ($C_1$-$C_6$)-alkyl-OSO$_2$R$^8$, ($C_1$-$C_6$)-alkyl-CO$_2$R$^7$, ($C_1$-$C_6$)-alkyl-SO$_2$OR$^7$, ($C_1$-$C_6$)-alkyl-CON(R$^7$)$_2$, ($C_1$-$C_6$)-alkyl-SO$_2$N(R$^7$)$_2$, ($C_1$-$C_6$)-alkyl-NR$^7$COR$^7$, ($C_1$-$C_6$)-alkyl-NR$^7$SO$_2$R$^8$, N(R$^7$)$_2$, P(O)(OR$^9$)$_2$, heteroaryl, heterocyclyl or phenyl, where the three last-mentioned radicals are each substituted by s radicals from the group consisting of halogen, nitro, cyano, ($C_1$-$C_6$)-alkyl, halo-($C_1$-$C_6$)-alkyl, ($C_3$-$C_6$)-cycloalkyl, S(O)$_n$-($C_1$-$C_6$)-alkyl, ($C_1$-$C_6$)-alkoxy and halo-($C_1$-$C_6$)-alkoxy, and where heterocyclyl carries n oxo groups, R$^1$ is hydrogen, ($C_1$-$C_6$)-alkyl, ($C_2$-$C_6$)-alkenyl, ($C_2$-$C_6$)-alkynyl, ($C_3$-$C_6$)-cycloalkyl, ($C_3$-$C_6$)-cycloalkenyl, ($C_3$-$C_6$)-cycloalkyl-($C_1$-$C_6$)-alkyl, where the six last-mentioned radicals are each substituted by s radicals from the group consisting of cyano, halogen, nitro, thiocyanato, OR$^{10}$, S(O)$_n$R$^{11}$, N(R$^{10}$)$_2$, NR$^{10}$OR$^{10}$, COR$^{10}$, OCOR$^{10}$, SCOR$^{11}$, NR$^{10}$COR$^{10}$, NR$^{10}$SO$_2$R$^{11}$, CO$_2$R$^{10}$, COSR$^{11}$, CON(R$^{10}$)$_2$ and ($C_1$-$C_4$)-alkoxy-($C_2$-$C_6$)-alkoxycarbonyl, or R$^1$ is phenyl, phenyl-($C_1$-$C_6$)-alkyl, heteroaryl, ($C_1$-$C_6$)-alkyl-heteroaryl, heterocyclyl, ($C_1$-$C_6$)-alkyl-heterocyclyl, ($C_1$-$C_6$)-alkyl-O-heteroaryl, ($C_1$-$C_6$)-alkyl-O-heterocyclyl, ($C_1$-$C_6$)-alkyl-NR$^{10}$-heteroaryl, ($C_1$-$C_6$)-alkyl-NR$^{10}$-heterocyclyl, where the ten last-mentioned radicals are each substituted by s radicals from the group consisting of cyano, halogen, nitro, thiocyanato, $(C_1-C_6)$-alkyl, halo-$(C_1-C_6)$-alkyl, $OR^{10}$, $S(O)_nR^{11}$, $N(R^{10})_2$, $NR^{10}OR^{10}$, $COR^{10}$, $OCOR^{10}$, $SCOR^{11}$, $NR^{10}COR^{10}$, $NR^{10}SO_2R^{11}$, $CO_2R^{10}$, $COSR^{11}$, $CON(R^{10})_2$ and $(C_1-C_4)$-alkoxy-$(C_2-C_6)$-alkoxycarbonyl, and where heterocyclyl carries n oxo groups, $R^2$ and $R^3$ independently of one another are each hydrogen, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $(C_1-C_6)$-alkoxy-$(C_1-C_6)$-alkyl, halo-$(C_1-C_6)$-alkoxy-$(C_1-C_6)$-alkyl, phenyl, heteroaryl or heterocyclyl, where the three last-mentioned radicals are each substituted by s radicals from the group consisting of cyano, halogen, nitro, thiocyanato, $(C_1-C_6)$-alkyl, halo-$(C_1-C_6)$-alkyl, $OR^{10}$, $S(O)_nR^{11}$, $N(R^{10})_2$, $NR^{10}OR^{10}$, $COR^{10}$, $OCOR^{10}$, $SCOR^{11}$, $NR^{10}COR^{10}$, $NR^{10}SO_2R^{11}$, $CO_2R^{10}$, $COSR^{11}$, $CON(R^{10})_2$ and $(C_1-C_4)$-alkoxy-$(C_2-C_6)$-alkoxycarbonyl, and where heterocyclyl carries n oxo groups, or $R^2$ and $R^3$ together with the atom to which they are attached form a 5- to 6-membered unsaturated, partially saturated or saturated ring which, in addition to carbon atoms, in each case contains n oxygen and sulfur atoms, $R^4$ is $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, where the six last-mentioned radicals are each substituted by s radicals from the group consisting of nitro, cyano, $SiR^9_3$, $PO(OR^9)_3$, $S(O)_n$-$(C_1-C_6)$-alkyl, $(C_1-C_6)$-alkoxy, halo-$(C_1-C_6)$-alkoxy, $N(R^7)_2$, $COR^7$, $COOR^7$, $OCOR^7$, $OCO_2R^8$, $NR^7COR^7$, $NR^7SO_2R^8$, $(C_3-C_6)$-cycloalkyl, heteroaryl, heterocyclyl, phenyl, W-heteroaryl, W-heterocyclyl, W-phenyl or W-benzyl, where the seven last-mentioned radicals for their part are substituted by s radicals from the group consisting of $(C_1-C_6)$-alkyl, halo-$(C_1-C_6)$-alkyl, $(C_1-C_6)$-alkoxy, halo-$(C_1-C_6)$-alkoxy and halogen, and where heterocyclyl carries n oxo groups, or $R^4$ is $(C_3-C_7)$-cycloalkyl, heteroaryl, heterocyclyl or phenyl, where the four last-mentioned radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$-$(C_1-C_6)$-alkyl, $(C_1-C_6)$-alkoxy, halo-$(C_1-C_6)$-alkoxy and $(C_1-C_6)$-alkoxy-$(C_1-C_4)$-alkyl, $R^5$ is hydrogen, $(C_1-C_6)$-alkyl, halo-$(C_1-C_6)$-alkyl, $(C_2-C_6)$-alkenyl, $(C_2-C_6)$-haloalkenyl, $(C_2-C_6)$-alkynyl, $(C_2-C_6)$-haloalkynyl, $(C_3-C_7)$-cycloalkyl, $(C_1-C_6)$-alkoxy, halo-$(C_1-C_6)$-alkoxy, $(C_2-C_6)$-alkenyloxy, $(C_2-C_6)$-alkynyloxy, cyano, nitro, methylsulfenyl, methylsulfinyl, methylsulfonyl, acetylamino, benzoylamino, methoxycarbonyl, ethoxycarbonyl, methoxycarbonylmethyl, ethoxycarbonylmethyl, benzoyl, methylcarbonyl, piperidinylcarbonyl, trifluoromethylcarbonyl, halogen, amino, aminocarbonyl, methylaminocarbonyl, dimethylaminocarbonyl, methoxymethyl, or heteroaryl, heterocyclyl or phenyl, each of which is substituted by s radicals from the group consisting of $(C_1-C_6)$-alkyl, halo-$(C_1-C_6)$-alkyl, $(C_1-C_6)$-alkoxy, halo-$(C_1-C_6)$-alkoxy and halogen, and where heterocyclyl carries n oxo groups, $R^6$ is hydrogen, $(C_1-C_6)$-alkyl, $R^7O$—$(C_1-C_6)$-alkyl, $CH_2R^{12}$, $(C_3-C_7)$-cycloalkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $OR^7$, $NHR^7$, methoxycarbonyl, ethoxycarbonyl, methoxycarbonylmethyl, ethoxycarbonylmethyl, methylcarbonyl, trifluoromethylcarbonyl, dimethylamino, acetylamino, methylsulfenyl, methylsulfinyl, methylsulfonyl, or heteroaryl, heterocyclyl, benzyl or phenyl, each of which is substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy and $(C_1-C_6)$-alkoxy-$(C_1-C_4)$-alkyl, where heterocyclyl carries n oxo groups, $R^7$ is hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkenyl, $(C_3-C_6)$-cycloalkyl-$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^{10}$-heteroaryl, $(C_1-C_6)$-alkyl-$NR^{10}$-heterocyclyl, where the 16 last-mentioned radicals are each substituted by s radicals from the group consisting of cyano, halogen, nitro, thiocyanato, $OR^{10}$, $S(O)_nR^{11}$, $N(R^{10})_2$, $NR^{10}OR^{10}$, $COR^{10}$, $OCOR^{10}$, $SCOR^{11}$, $NR^{10}COR^{10}$, $NR^{10}SO_2R^{11}$, $CO_2R^{10}$, $COSR^{11}$, $CON(R^{10})_2$ and $(C_1-C_4)$-alkoxy-$(C_2-C_6)$-alkoxycarbonyl, and where heterocyclyl carries n oxo groups, $R^8$ is $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkenyl, $(C_3-C_6)$-cycloalkyl-$(C_1-C_6)$-alkyl, phenyl, phenyl-$(C_1-C_6)$-alkyl, heteroaryl, $(C_1-C_6)$-alkyl-heteroaryl, heterocyclyl, $(C_1-C_6)$-alkyl-heterocyclyl, $(C_1-C_6)$-alkyl-O-heteroaryl, $(C_1-C_6)$-alkyl-O-heterocyclyl, $(C_1-C_6)$-alkyl-$NR^{10}$-heteroaryl, $(C_1-C_6)$-alkyl-$NR^{10}$-heterocyclyl, where the 16 last-mentioned radicals are each substituted by s radicals from the group consisting of cyano, halogen, nitro, thiocyanato, $OR^{10}$, $S(O)_nR^{11}$, $N(R^{10})_2$, $NR^{10}OR^{10}$, $COR^{10}$, $OCOR^{10}$, $SCOR^{11}$, $NR^{10}COR^{10}$, $NR^{10}SO_2R^{11}$, $CO_2R^{10}$, $COSR^{11}$, $CON(R^{10})_2$ and $(C_1-C_4)$-alkoxy-$(C_2-C_6)$-alkoxycarbonyl, and where heterocyclyl carries n oxo groups, $R^9$ is methyl or ethyl, $R^{10}$ is hydrogen, $(C_1-C_6)$-alkyl, halo-$(C_1-C_6)$-alkyl $(C_2-C_6)$-alkenyl, $(C_2-C_6)$-alkynyl, $(C_3-C_6)$-cycloalkyl or $(C_3-C_6)$-cycloalkyl-$(C_1-C_6)$-alkyl, $R^{11}$ is $(C_1-C_6)$-alkyl, $(C_2-C_6)$-alkenyl or $(C_2-C_6)$-alkynyl, $R^{12}$ is acetoxy, acetamido, N-methylacetamido, benzoyloxy, benzamido, N-methylbenzamido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, $(C_1-C_6)$-alkoxy, $(C_3-C_6)$-cycloalkyl, or heteroaryl, heterocyclyl or phenyl each substituted by s radicals from the group consisting of methyl, ethyl, methoxy, trifluoromethyl and halogen, $R^{13}$ is $(C_1-C_6)$-alkyl, $(C_2-C_6)$-alkenyl or $(C_2-C_6)$-alkynyl, phenyl W is O, S, or $NR^{13}$, n is 0, 1 or 2;

s is 0, 1, 2 or 3.

DETAILED DESCRIPTION OF A PREFERRED EMBODIMENT

In the formula (I) and all the formulae which follow, alkyl radicals having more than two carbon atoms may be straight-chain or branched. Alkyl radicals are, for example, methyl, ethyl, n- or isopropyl, n-, iso-, tert- or 2-butyl, pentyls, hexyls such as n-hexyl, isohexyl and 1,3-dimethylbutyl. Analogously, alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl. Alkynyl is, for example, propargyl, but-2-yn-1-yl, but-3-yn-1-yl, 1-methylbut-3-yn-1-yl. The multiple bond may be in any position of the unsaturated radical. Cycloalkyl is a carbocyclic saturated ring system having three to six carbon atoms, for example cyclopropyl, cyclobutyl, cyclopentyl or cyclohexyl. Analogously, cycloalkenyl is a monocyclic alkenyl group having three to six carbon ring members, for example cyclopropenyl, cyclobutenyl, cyclopentenyl and cyclohexenyl, where the double bond may be in any position.

Halogen is fluorine, chlorine, bromine or iodine.

Heterocyclyl is a saturated, semisaturated or fully unsaturated cyclic radical containing 3 to 6 ring atoms, of which 1 to 4 are from the group of oxygen, nitrogen and sulfur, and which may additionally be fused by a benzo ring. For example, heterocyclyl is piperidinyl, pyrrolidinyl, tetrahydrofuranyl, dihydrofuranyl and oxetanyl.

Heteroaryl is an aromatic cyclic radical containing 3 to 6 ring atoms, of which 1 to 4 are from the group of oxygen, nitrogen and sulfur, and which may additionally be fused by a benzo ring. For example, heteroaryl is benzimidazol-2-yl, furanyl, imidazolyl, isoxazolyl, isothiazolyl, oxazolyl, pyrazinyl, pyrimidinyl, pyridazinyl, pyridinyl, benzisoxazolyl, thiazolyl, pyrrolyl, pyrazolyl, thiophenyl, 1,2,3-oxadiazolyl, 1,2,4-oxadiazolyl, 1,2,5-oxadiazolyl, 1,3,4-oxadiazolyl, 1,2,4-triazolyl, 1,2,3-triazolyl, 1,2,5-triazolyl, 1,3,4-triazolyl, 1,2,4-triazolyl, 1,2,4-thiadiazolyl, 1,3,4-thiadiazolyl, 1,2,3-thiadiazolyl, 1,2,5-thiadiazolyl, 2H-1,2,3,4-tetrazolyl, 1H-1,2,3,4-tetrazolyl, 1,2,3,4-oxatriazolyl, 1,2,3,5-oxatriazolyl, 1,2,3,4-thiatriazolyl and 1,2,3,5-thiatriazolyl.

Where a group is substituted by a plurality of radicals, this means that this group is substituted by one or more identical or different representatives of the radicals mentioned. This applies analogously to the construction of ring systems from various atoms and elements. Here, compounds known to the person skilled in the art to be chemically unstable under standard conditions are meant to be excluded from the scope of the claims.

Depending on the nature and the attachment of the substituents, the compounds of the general formula (I) may be present as stereoisomers. When, for example, one or more asymmetric carbon atoms are present, enantiomers and diastereomers may occur. Stereoisomers likewise occur when n is 1 (sulfoxides). Stereoisomers can be obtained from the mixtures obtained in the preparation by customary separation methods, for example by chromatographic separation processes. It is equally possible to selectively prepare stereoisomers by using stereoselective reactions using optically active starting materials and/or auxiliaries. The invention also relates to all stereoisomers and mixtures thereof which are encompassed by the general formula (I) but not defined specifically. Owing to the oxime ether structure, the compounds according to the invention may also be present as geometric isomers (E/Z isomers). The invention also relates to all E/Z isomers and mixtures thereof which are encompassed by the general formula (I) but not defined specifically.

The compounds of the formula (I) may form salts. Salts can be formed by the action of a base on those compounds of the formula (I) which bear an acidic hydrogen atom, for example in the case that $R^1$ contains a COOH group or a sulfonamide group —NHSO$_2$—. Suitable bases are, for example, organic amines such as trialkylamines, morpholine, piperidine or pyridine, and also ammonium, alkali metal or alkaline earth metal hydroxides, carbonates and hydrogencarbonates, especially sodium and potassium hydroxide, sodium and potassium carbonate and sodium and potassium hydrogencarbonate. These salts are compounds in which the acidic hydrogen is replaced by an agriculturally suitable cation, for example metal salts, especially alkali metal salts or alkaline earth metal salts, especially sodium and potassium salts, or else ammonium salts, salts with organic amines or quaternary ammonium salts, for example with cations of the formula [NRR'R''R''']$^+$ in which R to R''' are each independently of one another an organic radical, especially alkyl, aryl, aralkyl or alkylaryl. Also useful are alkylsulfonium and alkylsulfoxonium salts, such as ($C_1$-$C_4$)-trialkylsulfonium and ($C_1$-$C_4$)-trialkylsulfoxonium salts.

The compounds of the formula (I) can form salts by addition of a suitable inorganic or organic acid, for example mineral acids, for example HCl, HBr, $H_2SO_4$, $H_3PO_4$ or $HNO_3$, or organic acids, for example carboxylic acids such as formic acid, acetic acid, propionic acid, oxalic acid, lactic acid or salicylic acid, or sulfonic acids, for example p-toluenesulfonic acid, onto a basic group, for example amino, alkylamino, dialkylamino, piperidino, morpholino or pyridino. These salts then contain the conjugate base of the acid as the anion.

Preference is given to compounds of the general formula (I) in which

Q is a Q1, Q2, Q3 or Q4 radical,

(Q1)

(Q2)

(Q3)

(Q4)

R is —CH=N—OR$^1$, —CH$_2$—O—N=CR$^2$R$^3$,

X is nitro, halogen, cyano, ($C_1$-$C_6$)-alkyl, halo-($C_1$-$C_6$)-alkyl, ($C_2$-$C_6$)-alkenyl, ($C_2$-$C_6$)-alkynyl, ($C_3$-$C_6$)-cycloalkyl, ($C_3$-$C_6$)-cycloalkyl-($C_1$-$C_6$)-alkyl, OR$^7$, S(O)$_n$R$^8$, SO$_2$N(R$^7$)$_2$, NR$^7$SO$_2$R$^8$, ($C_1$-$C_6$)-alkyl-S(O)$_n$R$^8$, ($C_1$-$C_6$)-alkyl-OR$^7$, ($C_1$-$C_6$)-alkyl-CO$_2$R$^7$, ($C_1$-$C_6$)-alkyl-CON(R$^7$)$_2$, ($C_1$-$C_6$)-alkyl-SO$_2$N(R$^7$)$_2$, ($C_1$-$C_6$)-alkyl-NR$^7$COR$^7$, ($C_1$-$C_6$)-alkyl-NR$^7$SO$_2$R$^8$, N(R$^7$)$_2$, P(O)(OR$^9$)$_2$, CH$_2$P(O)(OR$^9$)$_2$, heteroaryl, heterocyclyl, phenyl, ($C_1$-$C_6$)-alkyl-heteroaryl or ($C_1$-$C_6$)-alkyl-heterocyclyl, where the five last-mentioned radicals are each substituted by s radicals from the group consisting of halogen, nitro, cyano, ($C_1$-$C_6$)-alkyl, halo-($C_1$-$C_6$)-alkyl, S(O)$_n$-($C_1$-$C_6$)-alkyl, ($C_1$-$C_6$)-alkoxy and halo-($C_1$-$C_6$)-alkoxy, and where heterocyclyl carries n oxo groups, Y is nitro, halogen, cyano, ($C_1$-$C_6$)-alkyl, halo-($C_1$-$C_6$)-alkyl, ($C_2$-$C_6$)-alkenyl, halo-($C_2$-$C_6$)-alkenyl, ($C_2$-$C_6$)-alkynyl, halo-($C_2$-$C_6$)-alkynyl, ($C_3$-$C_6$)-cycloalkyl, OR$^7$, OSO$_2$R$^8$, S(O)$_n$R$^8$, SO$_2$OR$^8$, SO$_2$N(R$^7$)$_2$, NR$^7$SO$_2$R$^8$, N(R$^7$)$_2$, P(O)(OR$^9$)$_2$, heteroaryl, heterocyclyl or phenyl, where the three last-mentioned radicals are each substituted by s radicals from the group consisting of halogen, nitro, cyano, ($C_1$-$C_6$)-alkyl, halo-($C_1$-$C_6$)-alkyl, ($C_3$-$C_6$)-cycloalkyl, S(O)$_n$-($C_1$-$C_6$)-Alkyl, ($C_1$-$C_6$)-alkoxy and halo-($C_1$-$C_6$)-alkoxy, and where heterocyclyl carries n oxo groups, $R^1$ is hydrogen, ($C_1$-$C_6$)-alkyl, ($C_2$-$C_6$)-alkenyl, ($C_2$-$C_6$)-alkynyl, ($C_3$-$C_6$)-cycloalkyl, ($C_3$-$C_6$)-cycloalkyl-($C_1$-$C_6$)-alkyl, where the five last-mentioned radicals are each substituted by s radicals from the group consisting of cyano, halogen, nitro, $OR^{10}$, $S(O)_nR^{11}$, $COR^{10}$, $OCOR^{10}$, $NR^{10}COR^{10}$, $NR^{10}SO_2R^{11}$, $CO_2R^{10}$, $CON(R^{10})_2$ and ($C_1$-$C_4$)-alkoxy-($C_2$-$C_6$)-alkoxycarbonyl, or $R^1$ is phenyl, phenyl-($C_1$-$C_6$)-alkyl, heteroaryl, ($C_1$-$C_6$)-alkyl-heteroaryl, heterocyclyl, ($C_1$-$C_6$)-alkyl-heterocyclyl, ($C_1$-$C_6$)-alkyl-O-heteroaryl, ($C_1$-$C_6$)-alkyl-O-heterocyclyl, ($C_1$-$C_6$)-alkyl-$NR^{10}$-heteroaryl or ($C_1$-$C_6$)-alkyl-$NR^{10}$-heterocyclyl, where the ten last-mentioned radicals are each substituted by s radicals from the group consisting of cyano, halogen, nitro, thiocyanato, ($C_1$-$C_6$)-alkyl, halo-($C_1$-$C_6$)-alkyl, $OR^{10}$, $S(O)_nR^{11}$, $N(R^{10})_2$, $COR^{10}$, $OCOR^{10}$, $NR^{10}COR^{10}$, $NR^{10}SO_2R^{11}$, $CO_2R^{10}$, $CON(R^{10})_2$ and ($C_1$-$C_4$)-alkoxy-($C_2$-$C_6$)-alkoxycarbonyl, and where heterocyclyl carries n oxo groups, $R^2$ and $R^3$ independently of one another are each hydrogen, ($C_1$-$C_6$)-alkyl, halo-($C_1$-$C_6$)-alkyl, ($C_2$-$C_6$)-alkenyl, halo-($C_2$-$C_6$)-alkenyl, ($C_2$-$C_6$)-alkynyl, halo-($C_2$-$C_6$)-alkynyl, ($C_3$-$C_6$)-cycloalkyl, ($C_1$-$C_6$)-cycloalkyl-($C_1$-$C_6$)-alkyl, ($C_1$-$C_6$)-alkoxy-($C_1$-$C_6$)-alkyl, halo-($C_1$-$C_6$)-alkoxy-($C_1$-$C_6$)-alkyl, phenyl, heteroaryl or heterocyclyl, where the three last-mentioned radicals are each substituted by s radicals from the group consisting of cyano, halogen, nitro, ($C_1$-$C_6$)-alkyl, halo-($C_1$-$C_6$)-alkyl, $OR^{10}$, $S(O)_nR^{11}$, $N(R^{10})_2$, $COR^{10}$, $NR^{10}COR^{10}$, $NR^{10}SO_2R^{11}$, $CO_2R^{10}$, $CON(R^{10})_2$ and ($C_1$-$C_4$)-alkoxy-($C_2$-$C_6$)-alkoxycarbonyl, and where heterocyclyl carries n oxo groups, or $R^2$ and $R^3$ together with the atom to which they are attached form a 5- to 6-membered unsaturated, partially saturated or saturated ring which, in addition to carbon atoms, in each case contains n oxygen and sulfur atoms, $R^4$ is ($C_1$-$C_6$)-alkyl, halo-($C_1$-$C_6$)-alkyl, ($C_2$-$C_6$)-alkenyl, halo-($C_2$-$C_6$)-alkenyl, ($C_2$-$C_6$)-alkynyl, halo-($C_2$-$C_6$)-alkynyl, where the six last-mentioned radicals are each substituted by s radicals from the group consisting of nitro, cyano, $S(O)_n$-($C_1$-$C_6$)-alkyl, ($C_1$-$C_6$)-alkoxy, halo-($C_1$-$C_6$)-alkoxy, $COOR^7$, $NR^7COR^7$, $NR^7SO_2R^8$, ($C_3$-$C_6$)-cycloalkyl, heteroaryl, heterocyclyl, phenyl, W-heteroaryl, W-heterocyclyl, W-phenyl and W-benzyl, where the 7 last-mentioned radicals for their part are substituted by s radicals from the group consisting of ($C_1$-$C_6$)-alkyl, halo-($C_1$-$C_6$)-alkyl, ($C_1$-$C_6$)-alkoxy, halo-($C_1$-$C_6$)-alkoxy and halogen, and where heterocyclyl carries n oxo groups, or $R^4$ is ($C_3$-$C_7$)-cycloalkyl, heteroaryl, heterocyclyl or phenyl, where the four last-mentioned radicals are each substituted by s radicals from the group consisting of halogen, nitro, cyano, ($C_1$-$C_6$)-alkyl, halo-($C_1$-$C_6$)-alkyl, ($C_3$-$C_6$)-cycloalkyl, $S(O)_n$-($C_1$-$C_6$)-alkyl, ($C_1$-$C_6$)-alkoxy, halo-($C_1$-$C_6$)-alkoxy and ($C_1$-$C_6$)-alkoxy-($C_1$-$C_4$)-alkyl, $R^5$ is hydrogen, ($C_1$-$C_6$)-alkyl, halo-($C_1$-$C_6$)-alkyl, ($C_2$-$C_6$)-alkenyl, ($C_2$-$C_6$)-haloalkenyl, ($C_2$-$C_6$)-alkynyl, ($C_2$-$C_6$)-haloalkynyl, ($C_3$-$C_7$)-cycloalkyl, ($C_1$-$C_6$)-alkoxy, halo-($C_1$-$C_6$)-alkoxy, ($C_2$-$C_6$)-alkenyloxy, ($C_2$-$C_6$)-alkynyloxy, cyano, nitro, methylsulfenyl, methylsulfinyl, methylsulfonyl, acetylamino, methoxycarbonyl, methoxycarbonylmethyl, methylcarbonyl, trifluoromethylcarbonyl, halogen, amino, aminocarbonyl, methylaminocarbonyl, dimethylaminocarbonyl, methoxymethyl, or heteroaryl, heterocyclyl or phenyl, each of which is substituted by s radicals from the group consisting of ($C_1$-$C_6$)-alkyl, halo-($C_1$-$C_6$)-alkyl, ($C_1$-$C_6$)-alkoxy, halo-($C_1$-$C_6$)-alkoxy and halogen, and where heterocyclyl carries n oxo groups, $R^6$ is hydrogen, ($C_1$-$C_6$)-alkyl, $R^7O$—($C_1$-$C_6$)-alkyl, $CH_2R^{12}$, ($C_3$-$C_7$)-cycloalkyl, halo-($C_1$-$C_6$)-alkyl, ($C_2$-$C_6$)-alkenyl, ($C_2$-$C_6$)-alkynyl, $OR^7$, $NHR^7$, methoxycarbonyl, methoxycarbonylmethyl, methylcarbonyl, trifluoromethylcarbonyl, dimethylamino, acetylamino, methylsulfenyl, methylsulfinyl, methylsulfonyl, or heteroaryl, heterocyclyl, benzyl or phenyl, each of which is substituted by s radicals from the group consisting of halogen, nitro, cyano, ($C_1$-$C_6$)-alkyl, halo-($C_1$-$C_6$)-alkyl, ($C_3$-$C_6$)-cycloalkyl, $S(O)_n$—($C_1$-$C_6$)-alkyl, ($C_1$-$C_6$)-alkoxy, halo-($C_1$-$C_6$)-alkoxy, ($C_1$-$C_6$)-alkoxy-($C_1$-$C_4$)-alkyl, and where heterocyclyl carries n oxo groups, $R^7$ is hydrogen, ($C_1$-$C_6$)-alkyl, ($C_2$-$C_6$)-alkenyl, ($C_2$-$C_6$)-alkynyl, ($C_3$-$C_6$)-cycloalkyl, ($C_3$-$C_6$)-cycloalkenyl, ($C_3$-$C_6$)-cycloalkyl-($C_1$-$C_6$)-alkyl, phenyl, heteroaryl, heterocyclyl, where the nine last-mentioned radicals are each substituted by s radicals from the group consisting of cyano, halogen, nitro, $OR^{10}$, $S(O)_nR^{11}$, $N(R^{10})_2$, $NR^{10}SO_2R^{11}$, $CO_2R^{10}$, $CON(R^{10})_2$ and ($C_1$-$C_4$)-alkoxy-($C_2$-$C_6$)-alkoxycarbonyl, and where heterocyclyl carries n oxo groups, $R^8$ is ($C_1$-$C_6$)-alkyl, ($C_2$-$C_6$)-alkenyl, ($C_2$-$C_6$)-alkynyl, ($C_3$-$C_6$)-cycloalkyl, ($C_3$-$C_6$)-cycloalkenyl, ($C_3$-$C_6$)-cycloalkyl-($C_1$-$C_6$)-alkyl, phenyl, heteroaryl, heterocyclyl, where the nine last-mentioned radicals are each substituted by s radicals from the group consisting of cyano, halogen, nitro, $OR^{10}$, $S(O)_nR^{11}$, $N(R^{10})_2$, $NR^{10}SO_2R^{11}$, $CO_2R^{10}$, $CON(R^{10})_2$ and ($C_1$-$C_4$)-alkoxy-($C_2$-$C_6$)-alkoxycarbonyl, and where heterocyclyl carries n oxo groups, $R^9$ is methyl or ethyl, $R^{10}$ is hydrogen, ($C_1$-$C_6$)-alkyl, halo-($C_1$-$C_6$)-alkyl ($C_2$-$C_6$)-alkenyl, ($C_2$-$C_6$)-alkynyl, ($C_3$-$C_6$)-cycloalkyl or ($C_3$-$C_6$)-cycloalkyl-($C_1$-$C_6$)-alkyl, $R^{11}$ is ($C_1$-$C_6$)-alkyl, ($C_2$-$C_6$)-alkenyl or ($C_2$-$C_6$)-alkynyl, $R^{12}$ is acetoxy, acetamido, N-methylacetamido, benzoyloxy, benzamido, N-methylbenzamido, methoxycarbonyl, ethoxycarbonyl, benzoyl, methylcarbonyl, trifluoromethylcarbonyl, aminocarbonyl, methylaminocarbonyl, dimethylaminocarbonyl, ($C_1$-$C_6$)-alkoxy, ($C_3$-$C_6$)-cycloalkyl, or heteroaryl, heterocyclyl or phenyl each substituted by s radicals from the group consisting of methyl, methoxy, trifluoromethyl and halogen, $R^{13}$ is ($C_1$-$C_6$)-alkyl, W is O, S or $NR^{13}$, n is 0, 1 or 2;

s is 0, 1, 2 or 3.

Particular preference is given to compounds of the general formula (I) in which

Q is a Q1 or Q2 radical,

(Q1)

(Q2)

R is —CH=N—$OR^1$, —$CH_2$—O—N=$CR^2R^3$,

X is nitro, halogen, ($C_1$-$C_6$)-alkyl, halo-($C_1$-$C_6$)-alkyl, $S(O)_nR^8$, ($C_1$-$C_6$)-alkyl-$S(O)_nR^8$, ($C_1$-$C_6$)-alkyl-$OR^7$, ($C_1$-$C_6$)-alkyl-$SO_2N(R^7)_2$ or ($C_1$-$C_6$)-alkyl-$NR^7SO_2R^8$, Y is nitro, halogen, halo-$(C_1$-$C_6)$-alkyl or $S(O)_n R^8$, $R^1$ is hydrogen, $(C_1$-$C_6)$-alkyl, $(C_2$-$C_6)$-alkenyl, $(C_2$-$C_6)$-alkynyl, $(C_3$-$C_6)$-cycloalkyl or $(C_3$-$C_6)$-cycloalkyl-$(C_1$-$C_6)$-alkyl, where the five last-mentioned radicals are each substituted by s radicals from the group consisting of cyano, halogen, $OR^{10}$ and $S(O)_n R^{11}$, $R^2$ and $R^3$ independently of one another are each hydrogen, $(C_1$-$C_6)$-alkyl, halo-$(C_1$-$C_6)$-alkyl, $(C_2$-$C_6)$-alkenyl, $(C_2$-$C_6)$-alkynyl, $(C_1$-$C_6)$-alkoxy-$(C_1$-$C_6)$-alkyl or halo-$(C_1$-$C_6)$-alkoxy-$(C_1$-$C_6)$-alkyl, $R^4$ is $(C_1$-$C_6)$-alkyl, $(C_2$-$C_6)$-alkenyl or $(C_2$-$C_6)$-alkynyl, where these three radicals are each substituted by s radicals $(C_1$-$C_6)$-alkoxy, $R^5$ is $(C_1$-$C_6)$-alkyl, $(C_2$-$C_6)$-alkenyl, $(C_2$-$C_6)$-alkynyl, $(C_3$-$C_7)$-cycloalkyl, $(C_1$-$C_6)$-alkoxy, $(C_2$-$C_6)$-alkenyloxy, $(C_2$-$C_6)$-alkynyloxy, acetylamino, halogen or methoxymethyl, $R^6$ is $(C_1$-$C_6)$-alkyl, $R^7O$—$(C_1$-$C_6)$-alkyl, $CH_2R^{12}$, $(C_3$-$C_7)$-cycloalkyl, $(C_2$-$C_6)$-alkenyl or $(C_2$-$C_6)$-alkynyl, $R^7$ is hydrogen, $(C_1$-$C_6)$-alkyl, $(C_2$-$C_6)$-alkenyl, $(C_2$-$C_6)$-alkynyl, $(C_3$-$C_6)$-cycloalkyl or $(C_3$-$C_6)$-cycloalkyl-$(C_1$-$C_6)$-alkyl, $R^8$ is $(C_1$-$C_6)$-alkyl, $(C_2$-$C_6)$-alkenyl, $(C_2$-$C_6)$-alkynyl, $(C_3$-$C_6)$-cycloalkyl, $(C_3$-$C_6)$-cycloalkenyl or $(C_3$-$C_6)$-cycloalkyl-$(C_1$-$C_6)$-alkyl, $R^9$ is methyl or ethyl, $R^{10}$ is hydrogen, $(C_1$-$C_6)$-alkyl, $(C_2$-$C_6)$-alkenyl, $(C_2$-$C_6)$-alkynyl, $(C_3$-$C_6)$-cycloalkyl or $(C_3$-$C_6)$-cycloalkyl-$(C_1$-$C_6)$-alkyl, $R^{11}$ is $(C_1$-$C_6)$-alkyl, $(C_2$-$C_6)$-alkenyl or $(C_2$-$C_6)$-alkynyl, $R^{12}$ is acetoxy, acetamido or $(C_3$-$C_6)$-cycloalkyl, $R^{13}$ is $(C_1$-$C_6)$-alkyl, W is O, S or $NR^{13}$, n is 0, 1 or 2;

s is 0, 1, 2 or 3.

Compounds according to the invention in which Q is Q1 or Q2 can be prepared, for example, by the method shown in scheme 1, by base-catalyzed reaction of a benzoyl chloride (11) with a 5-amino-1H-1,2,4-triazole or 5-amino-1H-tetrazole (III):

Scheme 1

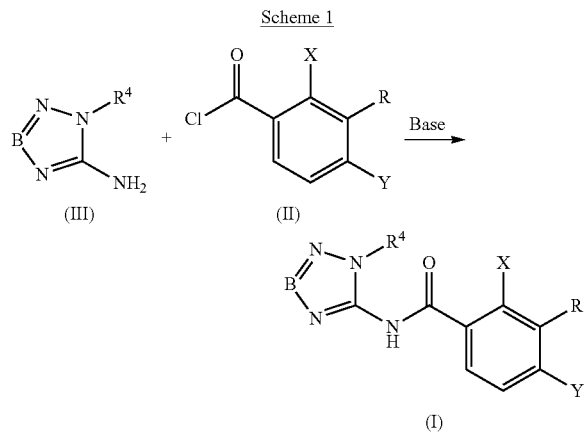

Here, B is CH or N. The benzoyl chlorides of the formula (II) or the benzoic acids on which they are based are known in principle and can be prepared, for example, by the methods described in WO 98/29392, WO98/29384 and JP 11043480.

Compounds according to the invention in which Q is Q1 or Q2 can also be prepared by the method shown in scheme 2, by reaction of a benzoic acid of the formula (IV) with a 5-amino-1H-1,2,4-triazole or 5-amino-1H-tetrazole (III):

Scheme 2

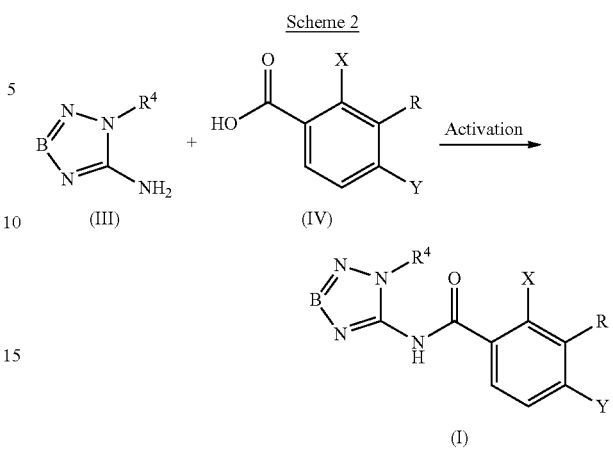

For the activation, it is possible to use dehydrating reagents which are typically used for amidation reactions, for example 1,1'-carbonyldiimidazole (CDI), dicyclohexylcarbodiimide (DCC), 2,4,6-tripropyl-1,3,5,2,4,6-trioxatriphosphinane 2,4,6-trioxide (T3P) etc.

Compounds according to the invention in which Q is Q1 or Q2 can also be prepared by the method shown in scheme 3, by reaction of an N-(1H-1,2,4-triazol-5-yl)benzamide, N-(1H-tetrazol-5-yl)benzamide, N-(1H-1,2,4-triazol-5-yl)nicotinamide or N-(1H-tetrazol-5-yl)nicotinamide:

Scheme 3

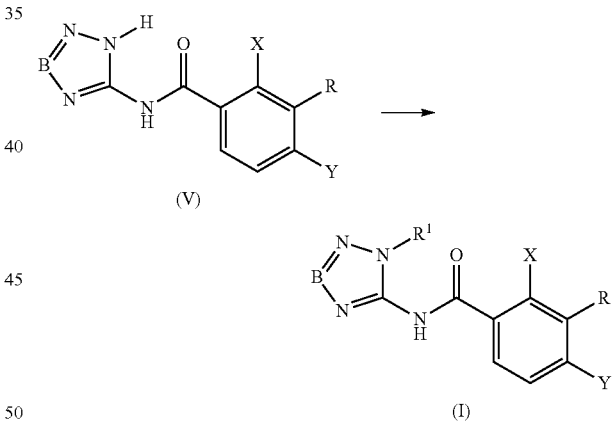

For this reaction shown in scheme 3, it is possible, for example, to use alkylating agents, for example alkyl halides or sulfonates or dialkyl sulfates, in the presence of a base.

It may be appropriate to alter the sequence of reaction steps. For instance, benzoic acids bearing a sulfoxide cannot be converted directly to their acid chlorides. One option here is first to prepare the amide to the thioether stage and then to oxidize the thioether to the sulfoxide.

The 5-amino-1H-tetrazoles of the formula (III) are either commercially available or can be prepared analogously to methods known from the literature. For example, substituted 5-aminotetrazoles can be prepared from aminotetrazole by the method described in Journal of the American Chemical Society (1954), 76, 923-924:

In the above reaction, X is a leaving group such as iodine. Substituted 5-aminotetrazoles can also be synthesized, for example, as described in Journal of the American Chemical Society (1954) 76, 88-89:

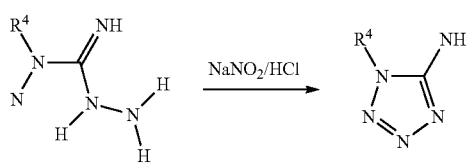

The 5-amino-1H-triazoles of the formula (III) are either commercially available or can be prepared analogously to methods known from the literature. For example, substituted 5-aminotriazoles can be prepared from aminotriazole by the method described in Zeitschrift füer Chemie (1990), 30(12), 436-437:

Substituted 5-aminotriazoles can also be synthesized, for example, as described in Chemische Berichte (1964), 97(2), 396-404:

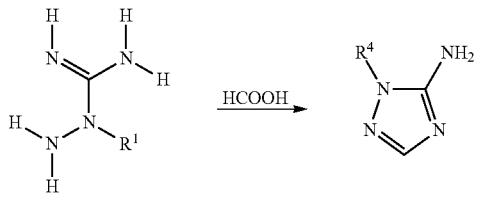

Substituted 5-aminotriazoles can also be synthesized, for example, as described in Angewandte Chemie (1963), 75, 918:

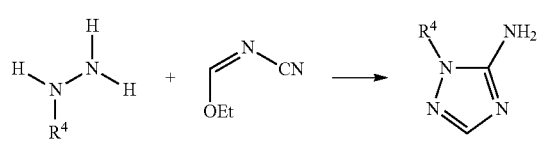

Compounds according to the invention in which Q is Q3 can be prepared, for example, by the method shown in scheme 4, by base-catalyzed reaction of a benzoyl chloride (II) with a 4-amino-1,2,5-oxadiazole (VI):

Scheme 4

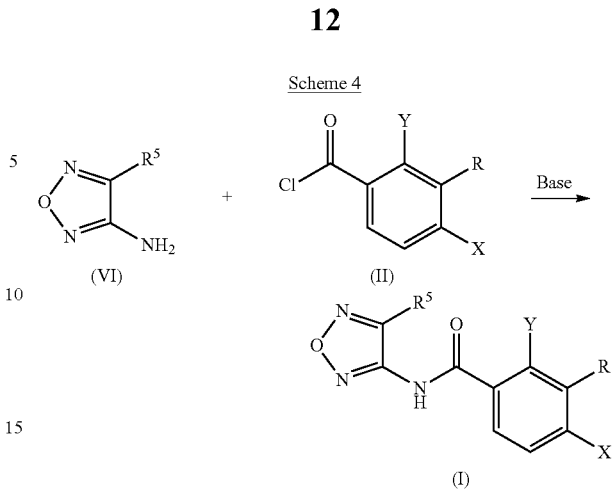

Compounds according to the invention can also be prepared by the method described in scheme 5, by reacting a benzoic acid of the formula (IV) with a 4-amino-1,2,5-oxadiazole (VI):

Scheme 5

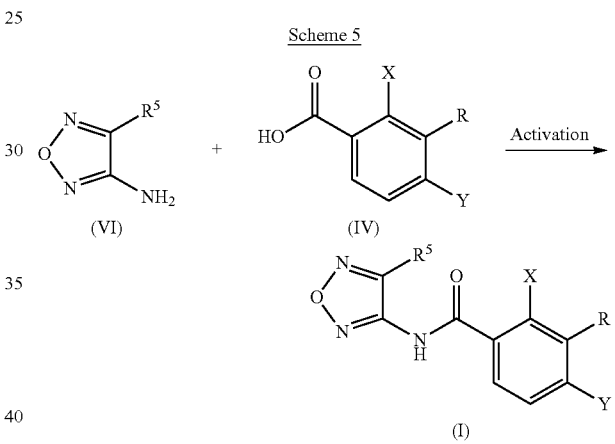

For the activation, it is possible to use dehydrating reagents which are typically used for amidation reactions, for example 1,1'-carbonyldiimidazole (CDI), dicyclohexylcarbodiimide (DCC), 2,4,6-tripropyl-1,3,5,2,4,6-trioxatriphosphinane 2,4,6-trioxide (T3P) etc.

The 4-amino-1,2,5-oxadiazoles of the formula (VI) are either commercially available or known, or can be prepared analogously to methods known from the literature. 3-Alkyl-4-amino-1,2,5-oxadiazoles can be prepared, for example, by the method described in Russian Chemical Bulletin, Int. Ed., Vol. 54, No. 4, pp 1032-1037 (2005) from β-keto esters:

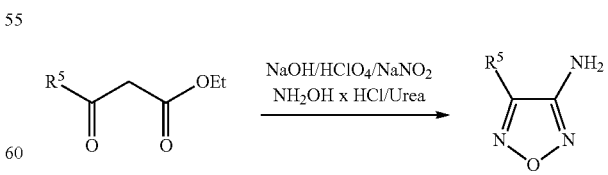

3-Aryl-4-amino-1,2,5-oxadiazoles can be synthesized, for example, as described in Russian Chemical Bulletin, 54(4), 1057-1059, (2005) or Indian Journal of Chemistry, Section B: Organic Chemistry Including Medicinal Chemistry, 26B(7), 690-2, (1987):

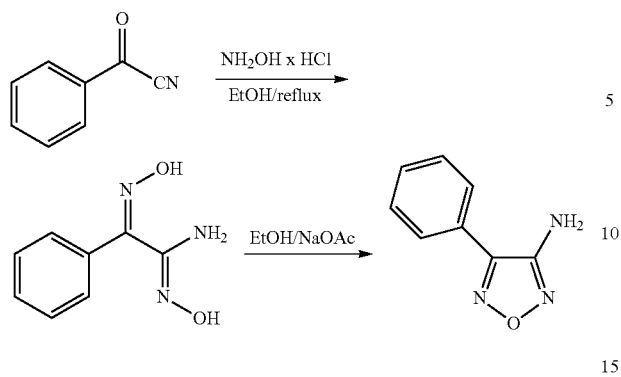

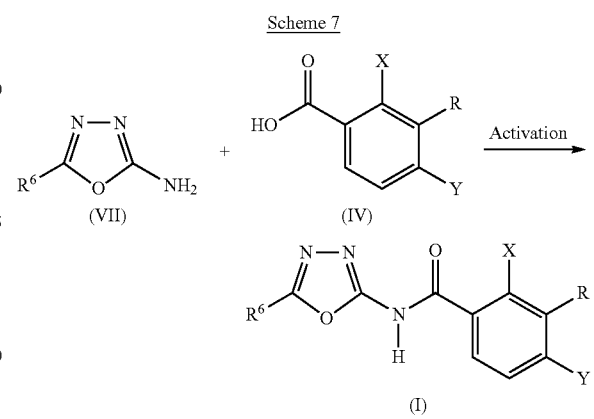

3-Amino-4-halo-1,2,5-oxadiazoles can be prepared, for example, by a Sandmeyer reaction from the commercially available 3,4-diamino-1,2,5-oxadiazole, according to the method described in Heteroatom Chemistry 15(3), 199-207 (2004):

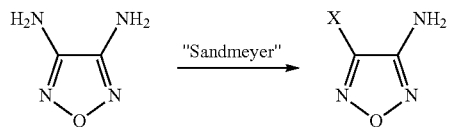

Nucleophilic $R^5$ radicals can be introduced into 3-amino-1,2,5-oxadiazoles by substitution of the leaving group L as described in Journal of Chemical Research, Synopses, (6), 190, 1985 or in or Izvestiya Akademii Nauk SSSR, Seriya Khimicheskaya, (9), 2086-8, 1986 or in Russian Chemical Bulletin (Translation of Izvestiya Akademii Nauk, Seriya Khimicheskaya), 53(3), 596-614, 2004:

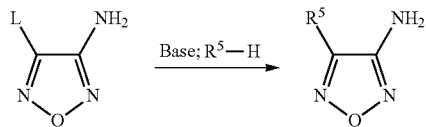

Compounds according to the invention in which Q is Q4 can be prepared, for example, by the method shown in scheme 6, by base-catalyzed reaction of a benzoyl chloride (11) with a 2-amino-1,3,4-oxadiazole (VII):

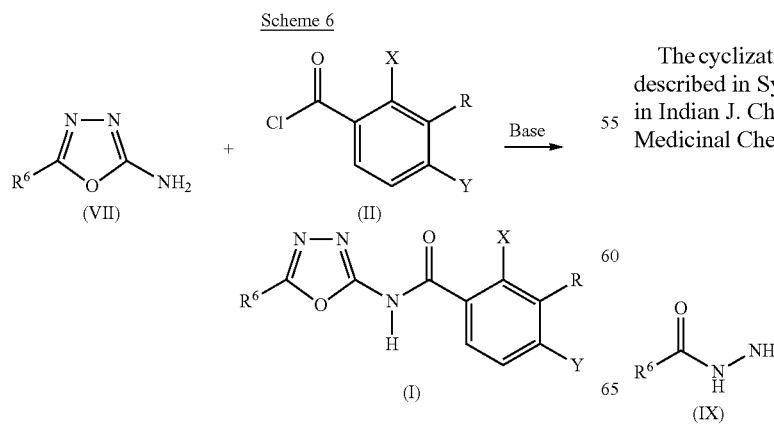

Compounds according to the invention can also be prepared by the method described in scheme 7, by reacting a benzoic acid of the formula (IV) with a 2-amino-1,3,4-oxadiazole (VII):

For the activation, it is possible to use dehydrating reagents which are typically used for amidation reactions, for example 1,1'-carbonyldiimidazole (CDI), dicyclohexylcarbodiimide (DCC), 2,4,6-tripropyl-1,3,5,2,4,6-trioxatriphosphinane 2,4,6-trioxide (T3P) etc.

Compounds according to the invention can also be prepared by the method described in scheme 8, by cyclizing a compound of the formula VIII

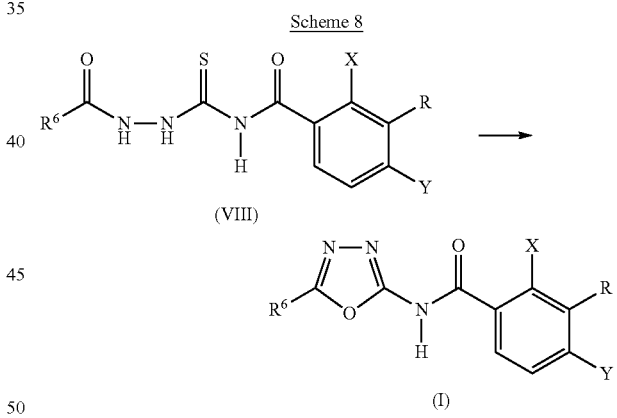

The cyclization can be carried out according to the methods described in Synth. Commun. 31 (12), 1907-1912 (2001) or in Indian J. Chem., Section B: Organic Chemistry Including Medicinal Chemistry; Vol. 43 (10), 2170-2174 (2004).

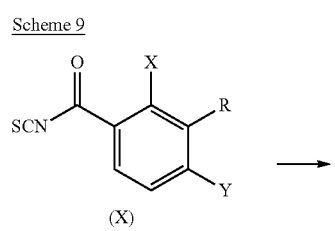

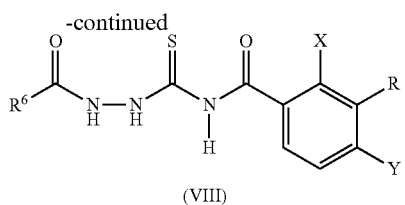

(VIII)

The compound of the formula VIII used in Scheme 8 can be prepared by reacting an acyl isocyanate of the formula X with a hydrazide of the formula IX according to the method described in Synth. Commun. 25(12), 1885-1892 (1995). It may be appropriate to alter the sequence of reaction steps. For instance, benzoic acids bearing a sulfoxide cannot be converted directly to their acid chlorides. One option here is first to prepare the amide to the thioether stage and then to oxidize the thioether to the sulfoxide.

Collections of compounds of the formula (I) and/or salts thereof which can be synthesized by the abovementioned reactions can also be prepared in a parallelized manner, in which case this may be accomplished in a manual, partly automated or fully automated manner. It is possible, for example, to automate the conduct of the reaction, the work-up or the purification of the products and/or intermediates. Overall, this is understood to mean a procedure as described, for example, by D. Tiebes in Combinatorial Chemistry—Synthesis, Analysis, Screening (editor: Ginther Jung), Wiley, 1999, on pages 1 to 34.

For the parallelized conduct of the reaction and workup, it is possible to use a number of commercially available instruments, for example Calypso reaction blocks from Barnstead International, Dubuque, Iowa 52004-0797, USA or reaction stations from Radleys, Shirehill, Saffron Walden, Essex, CB11 3AZ, England, or MultiPROBE Automated Workstations from PerkinElmer, Waltham, Mass. 02451, USA. For the parallelized purification of compounds of the general formula (I) and salts thereof or of intermediates which occur in the course of preparation, available apparatuses include chromatography apparatuses, for example from ISCO, Inc., 4700 Superior Street, Lincoln, Nebr. 68504, USA.

The apparatuses detailed lead to a modular procedure in which the individual working steps are automated, but manual operations have to be carried out between the working steps. This can be circumvented by using partly or fully integrated automation systems in which the respective automation modules are operated, for example, by robots. Automation systems of this type can be purchased, for example, from Caliper, Hopkinton, Mass. 01748, USA.

The implementation of single or multiple synthesis steps can be supported by the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Aside from the methods described here, the compounds of the general formula (I) and salts thereof can be prepared completely or partially by solid-phase supported methods. For this purpose, individual intermediates or all intermediates in the synthesis or a synthesis adapted for the corresponding procedure are bound to a synthesis resin. Solid phase-supported synthesis methods are described adequately in the technical literature, for example Barry A. Bunin in "The Combinatorial Index", Academic Press, 1998 and Combinatorial Chemistry—Synthesis, Analysis, Screening (editor: Ginther Jung), Wiley, 1999. The use of solid-phase-supported synthesis methods permits a number of protocols, which are known from the literature and which for their part may be performed manually or in an automated manner, to be carried out. The reactions can be performed, for example, by means of IRORI technology in microreactors from Nexus Biosystems, 12140 Community Road, Poway, Calif. 92064, USA.

Both on a solid phase and in liquid phase can the procedure of individual or several synthesis steps be supported through the use of microwave technology. The specialist literature describes a series of experimental protocols, for example in Microwaves in Organic and Medicinal Chemistry (editor C. O. Kappe and A. Stadler), Wiley, 2005. The preparation by the processes described here gives compounds of the formula (I) and salts thereof in the form of substance collections, which are called libraries. The present invention also provides libraries comprising at least two compounds of the formula (I) and salts thereof.

The compounds of the formula (I) according to the invention (and/or their salts), hereinbelow also referred to together as "compounds according to the invention", have excellent herbicidal efficacy against a broad spectrum of important monocotyledonous and dicotyledonous annual harmful plants. The active compounds act efficiently even on perennial harmful plants which produce shoots from rhizomes, root stocks and other perennial organs and which are difficult to control.

The present invention therefore also relates to a method for controlling unwanted plants or for regulating the growth of plants, preferably in crops of plants, where one or more compound(s) according to the invention is/are applied to the plants (for example harmful plants such as monocotyledonous or dicotyledonous weeds or undesired crop plants), to the seeds (for example grains, seeds or vegetative propagules such as tubers or shoot parts with buds) or to the area on which the plants grow (for example the area under cultivation). The compounds according to the invention can be deployed, for example, prior to sowing (if appropriate also by incorporation into the soil), prior to emergence or after emergence. Specific examples of some representatives of the monocotyledonous and dicotyledonous weed flora which can be controlled by the compounds according to the invention are as follows, though the enumeration is not intended to impose a restriction to particular species:

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

When the compounds according to the invention are applied to the soil surface before germination, either the weed seedlings are prevented completely from emerging or the weeds grow until they have reached the cotyledon stage, but then stop growing and eventually, after three to four weeks have elapsed, die completely.

If the active compounds are applied post-emergence to the green parts of the plants, growth stops after the treatment, and the harmful plants remain at the growth stage of the time of application, or die completely after a certain time, such that competition by the weeds, which is harmful to the crop plants, is thus eliminated very early and in a lasting manner.

Although the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, in particular *Zea* and *Triticum*, are damaged only to an insignificant extent, or not at all, depending on the structure of the respective compound according to the invention and its application rate. This is why the present compounds are highly suitable for the selective control of unwanted plant growth in plant crops such as agriculturally useful plants or ornamentals.

In addition, the compounds according to the invention (depending on their structure and the application rate) have outstanding growth-regulating properties in crop plants. They engage in the plant's metabolism in a regulatory fashion and can therefore be employed for the influencing, in a targeted manner, of plant constituents and for facilitating harvesting, such as, for example, by triggering desiccation and stunted growth. Moreover, they are also suitable for generally controlling and inhibiting unwanted vegetative growth without destroying the plants in the process. Inhibiting the vegetative growth plays an important role in many monocotyledonous and dicotyledonous crops since for example lodging can be reduced, or prevented completely, hereby.

By virtue of their herbicidal and plant growth-regulating properties, the active compounds can also be used for control of harmful plants in crops of genetically modified plants or plants modified by conventional mutagenesis. In general, the transgenic plants are distinguished by especially advantageous properties, for example by resistances to certain pesticides, mainly certain herbicides, resistances to plant diseases or causative organisms of plant diseases, such as certain insects or microorganisms such as fungi, bacteria or viruses. Other particular properties relate, for example, to the harvested material with regard to quantity, quality, storability, composition and specific constituents. For instance, there are known transgenic plants with an elevated starch content or altered starch quality, or with a different fatty acid composition in the harvested material.

It is preferred, with respect to transgenic crops, to use the compounds according to the invention in economically important transgenic crops of useful plants and ornamentals, for example of cereals such as wheat, barley, rye, oats, millet/sorghum, rice and corn or else crops of sugar beet, cotton, soybean, oilseed rape, potato, tomato, peas and other vegetables. It is preferred to employ the compounds according to the invention as herbicides in crops of useful plants which are resistant, or have been made resistant by recombinant means, to the phytotoxic effects of the herbicides.

Preference is given to the use of the compounds according to the invention or salts thereof in economically important transgenic crops of useful plants and ornamentals, for example of cereals such as wheat, barley, rye, oats, millet/sorghum, rice, cassava and corn, or else crops of sugar beet, cotton, soybean, oilseed rape, potato, tomato, peas and other vegetables. Preferably, the compounds according to the invention can be used as herbicides in crops of useful plants which are resistant, or have been made resistant by recombinant means, to the phytotoxic effects of the herbicides.

Conventional methods of generating novel plants which have modified properties in comparison to plants occurring to date consist, for example, in traditional breeding methods and the generation of mutants. Alternatively, novel plants with modified properties can be generated with the aid of recombinant methods (see, for example, EP-A-0221044, EP-A-0131624). For example, there have been many descriptions of:

recombinant modifications of crop plants for the purpose of modifying the starch synthesized in the plants (e.g. WO 92/11376, WO 92/14827, WO 91/19806), transgenic crop plants which are resistant to particular herbicides of the glufosinate type (cf., for example, EP-A-0242236, EP-A-242246) or glyphosate type (WO 92/00377) or of the sulfonylurea type (EP-A-0257993, U.S. Pat. No. 5,013,659), transgenic crop plants, for example cotton, with the ability to produce *Bacillus thuringiensis* toxins (Bt toxins) which make the plants resistant to particular pests (EP-A-0142924, EP-A-0193259), transgenic crop plants with a modified fatty acid composition (WO 91/13972), genetically modified crop plants with novel constituents or secondary metabolites, for example novel phytoalexins, which bring about an increased disease resistance (EPA 309862, EPA0464461), genetically modified plants with reduced photorespiration which feature higher yields and higher stress tolerance (EPA 0305398), transgenic crop plants which produce pharmaceutically or diagnostically important proteins ("molecular pharming"), transgenic crop plants which are distinguished by higher yields or better quality, transgenic crop plants which are distinguished by a combination, for example of the abovementioned novel properties ("gene stacking").

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431.

To carry out such recombinant manipulations, nucleic acid molecules which allow mutagenesis or a sequence change by recombination of DNA sequences can be introduced into plasmids. With the aid of standard methods, it is possible, for example, to undertake base exchanges, remove parts of sequences or add natural or synthetic sequences. For the joining of the DNA fragments to one another, adaptors or linkers can be attached to the fragments; see, for example, Sambrook et al., 1989, Molecular Cloning, A Laboratory Manual, 2nd ed. Cold Spring Harbor Laboratory Press, Cold Spring Harbor, N.Y.; or Winnacker "Gene und Klone" [Genes and Clones], VCH Weinheim 2nd edition 1996.

The production of plant cells with a reduced activity of a gene product can be achieved, for example, by the expression of at least one appropriate antisense RNA, or of a sense RNA for achievement of a cosuppression effect, or the expression of at least one appropriately constructed ribozyme which specifically cleaves transcripts of the abovementioned gene product. To this end, it is possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. The use of DNA sequences which have a high degree of homology to the coding sequences of a gene product, but are not completely identical to them, is also possible.

When expressing nucleic acid molecules in plants, the protein synthesized can be localized in any desired compartment of the plant cell. However, to achieve localization in a particular compartment, it is possible, for example, to link the coding region with DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give whole plants. In principle, the transgenic plants can be plants of any desired plant species, i.e. not only monocotyledonous, but also dicotyledonous, plants.

Thus, transgenic plants can be obtained whose properties are altered by overexpression, suppression or inhibition of homologous (=natural) genes or gene sequences or the expression of heterologous (=foreign) genes or gene sequences.

Preferably, the inventive compounds can be used in transgenic crops which are resistant to growth regulators, for example dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active ingredients.

On employment of the active compounds according to the invention in transgenic crops, not only do the effects toward harmful plants observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also provides for the use of the inventive compounds as herbicides for control of harmful plants in transgenic crop plants.

The compounds according to the invention can be applied in the form of wettable powders, emulsifiable concentrates, sprayable solutions, dusting products or granules in the customary formulations. The invention therefore also provides herbicidal and plant growth-regulating compositions which comprise the compounds according to the invention.

The compounds according to the invention can be formulated in various ways, according to the biological and/or physicochemical parameters required. Examples of possible formulations include: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical Engineering], volume 7, C. Hanser Verlag Munich, 4th ed. 1986; Wade van Valkenburg, "Pesticide Formulations", Marcel Dekker, N.Y., 1973; K. Martens, "Spray Drying" Handbook, 3rd ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd ed., Darland Books, Caldwell N.J., H.v. Olphen, "Introduction to Clay Colloid Chemistry"; 2nd ed., J. Wiley & Sons, N.Y.; C. Marsden, "Solvents Guide"; 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflächenaktive Äthylenoxidaddukte" [Interface-active Ethylene Oxide Adducts], Wiss. Verlagsgesell., Stuttgart 1976; Winnacker-Küchler, "Chemische Technologie" [Chemical Engineering], volume 7, C. Hanser Verlag Munich, 4th ed. 1986.

Based on these formulations, it is also possible to produce combinations with other pesticidally active compounds, such as, for example, insecticides, acaricides, herbicides, fungicides, and also with safeners, fertilizers and/or growth regulators, for example in the form of a finished formulation or as a tank mix. Suitable safeners are, for example, mefenpyrdiethyl, cyprosulfamide, isoxadifen-ethyl, cloquintocetmexyl and dichlormid.

Wettable powders are preparations which can be dispersed uniformly in water and, in addition to the active ingredient, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To produce the wettable powders, the herbicidal active compounds are ground finely, for example in customary apparatus such as hammer mills, blower mills and air-jet mills, and simultaneously or subsequently mixed with the formulation assistants.

Emulsifiable concentrates are produced by dissolving the active ingredient in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). The emulsifiers used may be, for example: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusts are obtained by grinding the active compound with finely distributed solid substances, for example talc, natural clays, such as kaolin, bentonite and pyrophyllite, or diatomaceous earth.

Suspension concentrates may be water- or oil-based. They may be prepared, for example, by wet grinding by means of commercial bead mills and optional addition of surfactants as have, for example, already been listed above for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be prepared either by spraying the active compound onto granulated inert material capable of adsorption or by applying active compound concentrates to the surface of carrier substances, such as sand, kaolinites or granulated inert material, by means of adhesives, for example polyvinyl alcohol, sodium polyacrylate or mineral oils. Suitable active compounds can also be granulated in the manner customary for the production of fertilizer granules—if desired as a mixture with fertilizers.

Water-dispersible granules are prepared generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London, J. E. Browning, "Agglomeration", Chemical and Engineering 1967, pages 147 ff.; "Perry's Chemical Engineer's Handbook", 5th Ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th ed., Blackwell Scientific Publications, Oxford, 1968, pages 101-103.

The agrochemical formulations contain generally 0.1 to 99% by weight, especially 0.1 to 95% by weight, of compounds according to the invention.

In wettable powders, the active compound concentration is, for example, from about 10 to 90% by weight, the remainder to 100% by weight consisting of customary formulation components. In the case of emulsifiable concentrates, the active compound concentration can be from about 1 to 90, preferably from 5 to 80, % by weight. Formulations in the form of dusts comprise 1 to 30% by weight of active ingredient, preferably usually 5 to 20% by weight of active ingredient; sprayable solutions contain about 0.05 to 80, preferably 2 to 50, % by weight of active ingredient. In the case of water-dispersible granules, the active ingredient content depends partly on whether the active compound is present in liquid or solid form and on which granulation assistants, fillers, etc., are used. In the water-dispersible granules, the content of active compound is, for example, between 1 and 95% by weight, preferably between 10 and 80% by weight.

In addition, the active compound formulations mentioned optionally comprise the respective customary tackifiers, wetting agents, dispersants, emulsifiers, penetrants, preservatives, antifreeze agents and solvents, fillers, carriers and dyes, defoamers, evaporation inhibitors and agents which influence the pH and the viscosity.

Based on these formulations, it is also possible to produce combinations with other pesticidally active compounds, such as, for example, insecticides, acaricides, herbicides, fungicides, and also with safeners, fertilizers and/or growth regulators, for example in the form of a finished formulation or as a tank mix.

Active compounds which can be employed in combination with the compounds according to the invention in mixed formulations or in the tank mix are, for example, known active compounds which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem I, photosystem II, protoporphyrinogen oxidase, as are described in, for example, Weed Research 26 (1986) 441-445 or "The Pesticide Manual", 15th edition, The British Crop Protection Council and the Royal Soc. of Chemistry, 2009 and the literature cited therein. Examples of known herbicides or plant growth regulators which can be combined with the inventive compounds include the active ingredients which follow (the compounds are designated by the "common name" according to the International Organization for Standardization (ISO) or by the chemical name or by the code number) and always encompass all use forms, such as acids, salts, esters and isomers, such as stereoisomers and optical isomers. One administration form or else, in some cases, more than one administration form is mentioned by way of example: acetochlor, acibenzolar, acibenzolar-S-methyl, acifluorfen, acifluorfen-sodium, aclonifen, alachlor, allidochlor, alloxydim, alloxydim-sodium, ametryne, amicarbazone, amidochlor, amidosulfuron, aminocyclopyrachlor, aminopyralid, amitrole, ammonium sulfamate, ancymidol, anilofos, asulam, atrazine, azafenidin, azimsulfuron, aziprotryne, beflubutamid, benazolin, benazolin-ethyl, bencarbazone, benfluralin, benfuresate, bensulide, bensulfuron, bensulfuron-methyl, bentazone, benzfendizone, benzobicyclon, benzofenap, benzofluor, benzoylprop, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat-chloride, chlornitrofen, chlorophthalim, chlorthal-dimethyl, chlortoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat-dibromide, dithiopyr, diuron, DNOC, eglinazine-ethyl, endothal, EPTC, esprocarb, ethalfluralin, ethametsulfuron, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoprop, fenoxaprop, fenoxaprop-P, fenoxaprop-ethyl, fenoxaprop-P-ethyl, fenoxasulfone, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, flurochloridone, fluroxypyr, fluroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, glufosinate-ammonium, glufosinate-P, glufosinate-P-ammonium, glufosinate-P-sodium, glyphosate, glyphosate-isopropylammonium, H-9201, i.e. O-(2,4-dimethyl-6-nitrophenyl)O-ethyl isopropylphosphoramidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl (2,4-dichlorophenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, inabenfide, indanofan, indaziflam, indoleacetic acid (IAA), 4-indol-3-ylbutyric acid (IBA), iodosulfuron, iodosulfuron-methyl-sodium, ioxynil, ipfencarbazone, isocarbamid, isopropalin, isoproturon, isouron, isoxaben, isoxachlortole, isoxaflutole, isoxapyrifop, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chloride, mesosulfuron, mesosulfuron-methyl, mesotrione, methabenzthiazuron, metam, metamifop, metamitron, metazachlor, metazasulfuron, methazole, methiopyrsulfuron, methiozolin, methoxyphenone, methyldymron, 1-methylcyclopropene, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monosulfuron ester, monuron, MT-128, i.e. 6-chloro-N-[(2E)-3-chloroprop-2-en-1-yl]-5-methyl-N-phenylpyridazine-3-amine, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolate-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazole, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, i.e. methyl (2R)-2-({7-[2-chloro-4-(trifluoromethyl)phenoxy]-2-naphthyl}oxy)propanoate, sulcotrione, sulfallate (CDEC), sulfentrazone, sulfometuron, sulfometuron-methyl, sulfosate (glyphosate-trimesium), sulfosulfuron, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, tebutam, tebuthiuron, tecnazene, tefuryltrione, tembotrione, tepraloxydim, terbacil, terbucarb, terbuchlor, terbumeton, terbuthylazine, terbutryne, thenylchlor, thiafluamide, thiazafluron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triafamone, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0862, i.e. 3,4-dichloro-N-{2-[(4,6-dimethoxypyrimidin-2-yl)oxy]benzyl}aniline, and the following compounds:

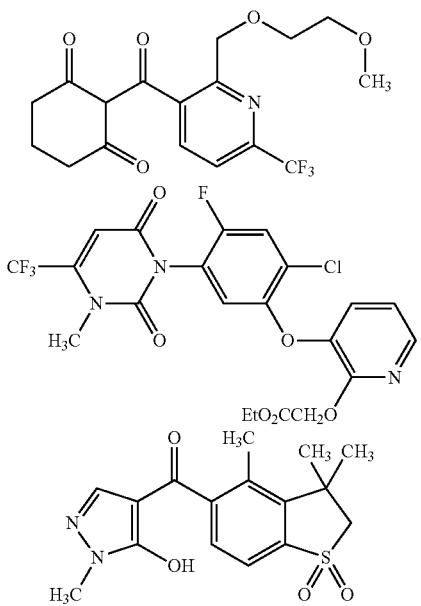

-continued

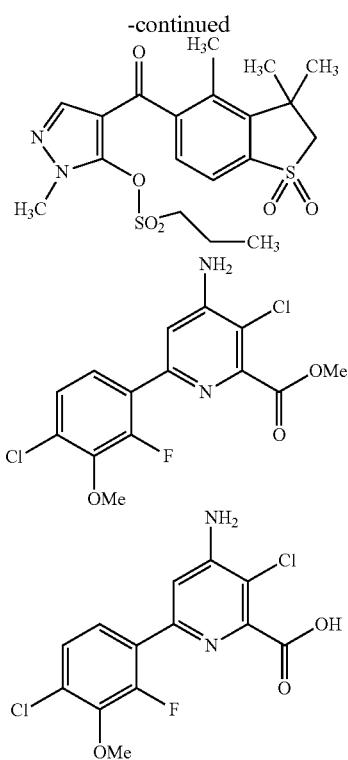

For application, the formulations present in commercial form are, if appropriate, diluted in a customary manner, for example in the case of wettable powders, emulsifiable concentrates, dispersions and water-dispersible granules with water. Preparations in the form of dusts, granules for soil application or granules for broadcasting and sprayable solutions are usually not diluted further with other inert substances prior to application. The required application rate of the compounds of the formula (I) varies with the external conditions, including temperature, humidity and the type of herbicide used. It may vary within wide limits, for example between 0.001 and 1.0 kg/ha or more of active substance; however, preferably it is between 0.005 and 750 g/ha.

The examples which follow illustrate the invention.

A. CHEMICAL EXAMPLES

1. Synthesis of 2,4-dichloro-N-(5-ethyl-1,3,4-oxadiazol-2-yl)-3-[(methoxyimino)methyl]benzamide (Table example 4-040)

400 mg (1.61 mmol) of 2,4-dichloro-3-[(methoxyimino) methyl]benzoic acid and 228 mg (2.0 mmol) of 5-ethyl-1,3, 4-oxadiazole-2-amine were dissolved in 3 ml of pyridine, and 10 mg of 4-dimethylaminopyridine and a drop of DMF were added. At room temperature (RT), 255.83 mg (2.016 mmol) of oxalyl chloride were then added dropwise, and the mixture was stirred at 70° C. for 4 h. 0.5 ml of water was then added to the reaction, which had once more been cooled, and the mixture was stirred for about 30 min, acidified with a saturated $KHSO_4$ solution and extracted three times with in each case 100 ml of ethyl acetate. The combined organic phases were washed once with 20 ml of a saturated $NaHCO_3$ solution, dried over $MgSO_4$, filtered off and concentrated. The residue was purified chromatographically by preparative HPLC. Yield: 99.3 mg (18%) as colorless crystals.

$^1$H-NMR (400 MHz, $CDCl_3$ δ, ppm) 8.21 (s, 1H), 7.63 (d, 1H), 7.42 (d, 1H), 4.03 (s, 3H), 2.86 (q, 2H), 1.38 (t, 3H).

2. Synthesis of 2-chloro-N-(1-ethyl-1H-tetrazol-5-yl)-4-(methylsulfonyl)-3-{[(prop-2-yn-1-yloxy)imino]methyl}benzamide (Table example 1-057)

400 mg (1.15 mmol) of 2-chloro-4-(methylsulfonyl)-3-{ [(prop-2-yn-1-yloxy)imino]methyl}benzoic acid and 171.60 mg (1.44 mmol) of 1-ethyl-1H-tetrazole-5-amine were dissolved in 4 ml of pyridine, and 10 mg of 4-dimethylaminopyridine and a drop of DMF were added. At RT, 186.65 mg (1.441 mmol) of oxalyl chloride were then added dropwise, and the mixture was stirred at 70° C. for 3 h. 0.5 ml of water was then added to the reaction, which had once more been cooled, and the mixture was stirred for about 30 min, acidified with a saturated $KHSO_4$ solution and extracted three times with in each case 100 ml of ethyl acetate. The combined organic phases were washed once with 20 ml of a saturated $NaHCO_3$ solution, dried over $MgSO_4$, filtered off and concentrated. Yield: 351.60 mg (67%) as an orange solid.

$^1$H-NMR (400 MHz, $CDCl_3$ δ, ppm) 8.35 (s, 1H), 7.93 (d, 1H), 7.82 (d, 1H), 4.78 (d, 2H), 4.30 (q, 2H), 3.25 (s, 3H), 2.49 (t, 1H), 1.48 (t, 3H).

3. Synthesis of 2-chloro-4-(methylsulfonyl)-N-(1-methyl-1H-1,2,4-triazol-5-yl)-3-{[(propan-2-ylideneamino)oxy]methyl}benzamide (Table example 6-017)

500 mg (1.56 mmol) of 2-chloro-4-(methylsulfonyl)-3-{ [(propan-2-ylideneamino)oxy]methyl}benzoic acid and 395 mg (1.34 mmol) of 1-methyl-1H-1,2,4-triazole-5-amine were dissolved in 2.5 ml of pyridine, and 10 mg of 4-dimethylaminopyridine and a drop of DMF were added. At RT, 313 mg (2.58 mmol) of thionyl chloride were then added dropwise, and the mixture was stirred at 70° C. for 5 h. 0.5 ml of water was then added to the reaction, which had once more been cooled, and the mixture was stirred for about 30 min, acidified with a saturated $KHSO_4$ solution and extracted three times with in each case 100 ml of ethyl acetate. The combined organic phases were washed once with 20 ml of a saturated $NaHCO_3$ solution, dried over $MgSO_4$, filtered off and concentrated. The residue was purified chromatographically on a silica gel column. Yield: 153 mg (24%) as a colorless oil.

$^1$H-NMR (400 MHz, $CDCl_3$ δ, ppm) 8.14 (d, 1H), 7.69 (d, 1H), 7.27 (s, 1H), 5.73 (s, 2H), 3.89 (s, 3H), 3.37 (s, 3H), 1.84 (s, 3H).

4. Synthesis of 2,4-dichloro-3-{(E)-[(cyclopropylmethoxy)imino]methyl}-N-(4-methyl-1,2,5-oxadiazol-3-yl)benzamide (Table example 3-004)

400 mg (1.39 mmol) of 2,4-dichloro-3-{[(cyclopropylmethoxy)imino]methyl}benzoic acid and 14418 mg (1.39 mmol) of 4-methyl-1,2,5-oxadiazole-3-amine were dissolved in 10 ml of $CH_2Cl_2$, 1.33 g (2.08 mmol) of propanephosphonic anhydride were added at 10-20° C. and the mixture was stirred at RT for 1 h. 700 mg of triethylamine and 34.6 mg (0.278 mmol) of DMAP were then added, and the mixture was stirred at RT for 2 days.

The mixture was washed with water and twice with 6N hydrochloric acid and the organic phase was then dried over $MgSO_4$ and concentrated. The residue was purified chromatographically on a silica gel column (heptane/ethyl acetate 4:1).

Yield: 248.6 mg (48%) as a colorless solid.

¹H-NMR (400 MHz, CDCl₃ δ, ppm) 8.30 (s, 1H), 8.19 (br, s, 1H), 7.66 (d, 1H), 7.51 (d, 1H), 4.06 (d, 2H), 2.49 (s, 3H), 1.25 (m, 1H), 0.61 (m, 2H), 0.37 (m, 2H).

Very particular preference is given to the compounds of the general formula (I) listed in Tables 1 to 8, which can be obtained analogously to the methods described herein.

The abbreviations used denote:

Et=ethyl Me=methyl n-Pr=n-propyl i-Pr=isopropyl c-Pr=cyclopropyl Ph=phenyl

TABLE 1

Compounds of the formula (I) according to the invention in which Q is Q1, R is CH=N—OR¹ and the other radicals have the meanings given in Table 1

| No. | R⁴ | X | Y | R¹ | Physical data (¹H-NMR) |
|---|---|---|---|---|---|
| 1-001 | Me | Cl | Cl | Me | (400 MHz, d⁶-DMSO δ, ppm) 11.88 (br, s, 1H), 8.36 (s, 1H), 7.80 (d, 1H), 7.74 (d, 1H), 4.00 (s, 3H), 3.90 (s, 3H) |
| 1-002 | Me | Cl | Cl | Et | (400 MHz, d⁶-DMSO δ, ppm) 11.88 (br, s, 1H), 8.35 (s, 1H), 7.80 (d, 1H), 7.74 (d, 1H), 4.20 (q, 2H), 4.00 (s, 3H), 1.28 (t, 3H) |
| 1-003 | Me | Cl | Cl | nPr | |
| 1-004 | Me | Cl | Cl | CH₂cPr | (400 MHz, CDCl₃ δ, ppm) 8.20 (s, 1H), 7.65 (d, 1H), 7.38 (d, 1H), 3.98 (d, 2H), 3.88 (s, 3H), 1.18 (m, 1H), 0.58 (m, 2H), 0.32 (m, 2H) |
| 1-005 | Me | Cl | Cl | CH₂CCH | (400 MHz, CDCl₃ δ, ppm) 10.40 (br, s, 1H), 8.32 (s, 1H), 7.68 (d, 1H), 7.52 (d, 1H), 4.83 (d, 2H), 4.11 (s, 3H), 2.53 (t, 1H) |
| 1-006 | Me | Cl | Cl | CH₂CH=CH₂ | |
| 1-007 | Me | Cl | Cl | CH₂CH(Me)₂ | (400 MHz, d⁶-DMSO δ, ppm) 11.88 (br, s, 1H), 8.38 (s, 1H), 7.81 (d, 1H), 7.73 (d, 1H), 4.00 (s, 3H), 3.94 (d, 2H), 2.01 (m, 1H), 0.93 (d, 6H) |
| 1-008 | Me | Cl | Cl | CH₂CH=C(Me)₂ | (400 MHz, CDCl₃ δ, ppm) 10.8 (br, s, 1H), 8.25 (s, 1H), 7.62 (d, 1H), 7.28 (d, 1H), 5.50 (t, 1H), 4.75 (d, 2H), 4.08 (s, 3H), 1.82 (s, 3H), 1.78 (s, 3H) |
| 1-009 | Me | Cl | Cl | CH₂CH₂OMe | |
| 1-010 | Me | Cl | Cl | CH₂CN | |
| 1-011 | Me | Cl | Cl | CH₂CH₂SMe | |
| 1-012 | Me | Cl | Cl | CH₂CF₃ | |
| 1-013 | Me | Cl | Cl | CH₂CHF₂ | |
| 1-014 | Me | Cl | SO₂Me | Me | (400 MHz, CDCl₃ δ, ppm) 8.28 (s, 1H), 7.94 (d, 1H), 7.80 (d, 1H), 3.98 (s, 3H), 3.84 (s, 3H), 3.24 (s, 3H) |
| 1-015 | Me | Cl | SO₂Me | Et | (400 MHz, CDCl₃ δ, ppm) 8.38 (s, 1H), 8.10 (d, 1H), 7.88 (d, 1H), 4.26 (q, 2H), 3.98 (s, 3H), 3.28 (s, 3H), 1.35 (t, 3H) |
| 1-016 | Me | Cl | SO₂Me | nPr | |
| 1-017 | Me | Cl | SO₂Me | CH₂cPr | (400 MHz, CDCl₃ δ, ppm) 8.32 (s, 1H), 7.95 (d, 1H), 7.80 (d, 1H), 3.99 (d, 2H), 3.87 (s, 3H), 3.23 (s, 3H), 1.18 (m, 3H), 0.58 (m, 2H), 0.31 (m, 2H) |
| 1-018 | Me | Cl | SO₂Me | CH₂CCH | (400 MHz, CDCl₃ δ, ppm) 8.35 (s, 1H), 7.92 (d, 1H), 7.82 (d, 1H), 4.75 (d, 2H), 3.85 (s, 3H), 3.25 (s, 3H), 2.49 (m, 1H) |
| 1-019 | Me | Cl | SO₂Me | CH₂CH=CH₂ | |
| 1-020 | Me | Cl | SO₂Me | CH₂CH(Me)₂ | (400 MHz, CDCl₃ δ, ppm) 8.29 (s, 1H), 7.95 (d, 1H), 7.79 (d, 1H), 3.95 (d, 2H), 3.25 (s, 3H), 2.02 (m, 1H), 0.98 (d, 6H) |
| 1-021 | Me | Cl | SO₂Me | CH₂CH=C(Me)₂ | |
| 1-022 | Me | Cl | SO₂Me | CH₂CH₂OMe | |
| 1-023 | Me | Cl | SO₂Me | CH₂CN | |
| 1-024 | Me | Cl | SO₂Me | CH₂CH₂SMe | |
| 1-025 | Me | Cl | SO₂Me | CH₂CF₃ | |
| 1-026 | Me | Cl | SO₂Me | CH₂CHF₂ | |
| 1-027 | Me | SO₂Me | Cl | Me | |
| 1-028 | Me | SO₂Me | Cl | Et | |
| 1-029 | Me | SO₂Me | Cl | nPr | |
| 1-030 | Me | SO₂Me | Cl | CH₂cPr | |
| 1-031 | Me | SO₂Me | Cl | CH₂CCH | |
| 1-032 | Me | SO₂Me | Cl | CH₂CH=CH₂ | |
| 1-033 | Me | SO₂Me | Cl | CH₂CH(Me)₂ | (400 MHz, CDCl₃ δ, ppm) 8.30 (s, 1H), 7.92 (d, 1H), 7.79 (d, 1H), 3.95 (s, 3H), 3.93 (d, 2H), 3.25 (s, 3H), 2.20 (m, 1H), 0.95 (d, 6H) |
| 1-034 | Me | SO₂Me | Cl | CH₂CH=C(Me)₂ | |
| 1-035 | Me | SO₂Me | Cl | CH₂CH₂OMe | |
| 1-036 | Me | SO₂Me | Cl | CH₂CN | |
| 1-037 | Me | SO₂Me | Cl | CH₂CH₂SMe | |
| 1-038 | Me | SO₂Me | Cl | CH₂CF₃ | |
| 1-039 | Me | SO₂Me | Cl | CH₂CHF₂ | |
| 1-040 | Et | Cl | Cl | Me | (400 MHz, CDCl₃ δ, ppm) 11.45 (br, s, 1H), 8.28 (s, 1H), 7.60 (d, 1H), 7.42 (d, 1H), 4.32 (q, 2H), 4.02 (s, 3H), 1.50 (t, 3H) |
| 1-041 | Et | Cl | Cl | Et | (400 MHz, CDCl₃ δ, ppm) 8.18 (s, 1H), 7.68 (d, 1H), 7.40 (d, 1H), 4.32 (q, 2H), 4.28 (q, 2H), 1.48 (t, 3H), 1.38 (t, 3H) |
| 1-042 | Et | Cl | Cl | nPr | |

TABLE 1-continued

Compounds of the formula (I) according to the invention in which Q is Q1, R is CH=N—OR¹ and the other radicals have the meanings given in Table 1

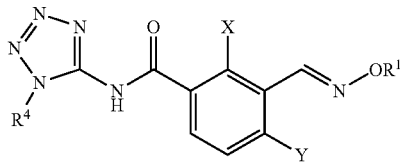

| No. | R⁴ | X | Y | R¹ | Physical data (¹H-NMR) |
|---|---|---|---|---|---|
| 1-043 | Et | Cl | Cl | CH₂cPr | (400 MHz, CDCl₃ δ, ppm) 11.7 (br, s, 1H), 8.22 (s, 1H), 7.58 (d, 1H), 7.40 (d, 1H), 4.32 (q, 2H), 4.02 (d, 2H), 1.49 (t, 3H), 1.10 (m, 1H), 0.60 (m, 2H), 0.33 (m, 2H) |
| 1-044 | Et | Cl | Cl | CH₂CCH | (400 MHz, CDCl₃ δ, ppm) 8.24 (s, 1H), 7.61 (d, 1H), 7.38 (d, 1H), 4.82 (d, 2H), 4.3 (q, 2H), 2.52 (t, 1H), 1.48 (t, 3H) |
| 1-045 | Et | Cl | Cl | CH₂CH=CH₂ | |
| 1-046 | Et | Cl | Cl | CH₂CH(Me)₂ | 400 MHz, CDCl₃ δ, ppm) 8.19 (s, 1H), 7.58 (d, 1H), 7.28 (d, 1H), 4.31 (q, 2H), 3.99 (d, 2H), 2.09 (m, 1H), 1.49 (t, 3H), 0.98 (d, 6H) |
| 1-047 | Et | Cl | Cl | CH₂CH=C(Me)₂ | (400 MHz, CDCl₃ δ, ppm) 8.18 (s, 1H), 7.58 (d, 1H), 7.28 (d, 1H), 5.50 (m, 1H), 4.72 (d, 2H), 4.30 (q, 2H), 1.80 (s, 3H), 1.75 (s, 3H), 1.50 (t, 3H) |
| 1-048 | Et | Cl | Cl | CH₂CH₂OMe | |
| 1-049 | Et | Cl | Cl | CH₂CN | |
| 1-050 | Et | Cl | Cl | CH₂CH₂SMe | |
| 1-051 | Et | Cl | Cl | CH₂CF₃ | |
| 1-052 | Et | Cl | Cl | CH₂CHF₂ | |
| 1-053 | Et | Cl | SO₂Me | Me | (400 MHz, CDCl₃ δ, ppm) 8.28 (s, 1H), 7.95 (d, 1H), 7.82 (d, 1H), 4.28 (q, 2H), 3.90 (s, 3H), 3.25 (s, 3H), 1.48 (t, 3H) |
| 1-054 | Et | Cl | SO₂Me | Et | (400 MHz, CDCl₃ δ, ppm) 8.40 (s, 1H), 8.00 (d, 1H), 7.85 (d, 1H), 4.20 (q, 2H), 4.18 (q, 2H), 3.32 (s, 3H), 1.35 (t, 3H), 1.25 (t, 3H) |
| 1-055 | Et | Cl | SO₂Me | nPr | |
| 1-056 | Et | Cl | SO₂Me | CH₂cPr | (400 MHz, CDCl₃ δ, ppm) 8.32 (s, 1H), 7.95 (d, 1H), 7.80 (d, 1H), 4.31 (q, 2H), 3.98 (d, 2H), 3.32 (s, 3H), 1.48 (t, 3H), 1.18 (m, 1H), 0.58 (m, 2H), 0.32 (m, 2H) |
| 1-057 | Et | Cl | SO₂Me | CH₂CCH | (400 MHz, CDCl₃ δ, ppm) 8.35 (s, 1H), 7.93 (d, 1H), 7.82 (d, 1H), 4.78 (d, 2H), 4.30 (q, 2H), 3.25 (s, 3H), 2.49 (t, 1H), 1.48 (t, 3H) |
| 1-058 | Et | Cl | SO₂Me | CH₂CH=CH₂ | |

TABLE 1-continued

Compounds of the formula (I) according to the invention in which Q is Q1, R is CH=N—OR¹ and the other radicals have the meanings given in Table 1

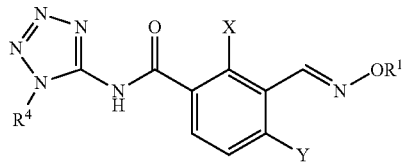

| No. | R⁴ | X | Y | R¹ | Physical data (¹H-NMR) |
|---|---|---|---|---|---|
| 1-059 | Et | Cl | SO₂Me | CH₂CH(Me)₂ | (400 MHz, CDCl₃ δ, ppm) 8.31 (s, 1H), 7.96 (d, 1H), 7.80 (d, 1H), 4.30 (q, 2H), 3.92 (d, 2H), 3.22 (s, 3H), 2.02 (m, 1H), 1.48 (t, 1H), 0.98 (d, 6H) |
| 1-060 | Et | Cl | SO₂Me | CH₂CH=C(Me)₂ | (400 MHz, CDCl₃ δ, ppm) 8.29 (s, 1H), 7.95 (d, 1H), 7.80 (d, 1H), 5.46 (t, 1H), 4.68 (d, 1H), 4.28 (q, 2H), 3.25 (s, 3H), 1.78 (s, 3H), 1.70 (s, 3H), 1.46 (t, 3H) |
| 1-061 | Et | Cl | SO₂Me | CH₂CH₂OMe | |
| 1-062 | Et | Cl | SO₂Me | CH₂CN | |
| 1-063 | Et | Cl | SO₂Me | CH₂CH₂SMe | |
| 1-064 | Et | Cl | SO₂Me | CH₂CF₃ | |
| 1-065 | Et | Cl | SO₂Me | CH₂CHF₂ | |
| 1-066 | Et | SO₂Me | Cl | Me | |
| 1-067 | Et | SO₂Me | Cl | Et | |
| 1-068 | Et | SO₂Me | Cl | nPr | |
| 1-069 | Et | SO₂Me | Cl | CH₂cPr | |
| 1-070 | Et | SO₂Me | Cl | CH₂CCH | |
| 1-071 | Et | SO₂Me | Cl | CH₂C=CH₂ | |
| 1-072 | Et | SO₂Me | Cl | CH₂CH(Me)₂ | |
| 1-073 | Et | SO₂Me | Cl | CH₂CH=C(Me)₂ | |
| 1-074 | Et | SO₂Me | Cl | CH₂CH₂OMe | |
| 1-075 | Et | SO₂Me | Cl | CH₂CN | |
| 1-076 | Et | SO₂Me | Cl | CH₂CH₂SMe | |
| 1-077 | Et | SO₂Me | Cl | CH₂CF₃ | |
| 1-078 | Et | SO₂Me | Cl | CH₂CHF₂ | |
| 1-079 | nPr | Cl | Cl | Me | (400 MHz, CDCl₃ δ, ppm) 10.30 (br, s, 1H), 8.24 (s, 1H), 7.65 (d, 1H), 7.50 (d, 1H), 4.41 (t, 2H), 4.04 (s, 3H), 2.01 (m, 2H), 0.98 (t, 3H) |
| 1-080 | nPr | Cl | Cl | Et | (400 MHz, d⁶-DMSO δ, ppm) 11.78 (br, s, 1H), 8.35 (s, 1H), 7.75 (d, 1H), 7.70 (d, 1H), 4.29 (t, 2H), 4.18 (q, 2H), 1.88 (m, 2H), 1.25 (t, 3H), 0.85 (t, 3H) |
| 1-081 | nPr | Cl | Cl | nPr | |
| 1-082 | nPr | Cl | Cl | CH₂cPr | (400 MHz, CDCl₃ δ, ppm) 8.21 (s, 1H), 7.58 (d, 1H), 7.38 (d, 1H), 4.42 (t, 2H), 4.05 (d, 2H), 2.01 (m, 2H), 1.25 (m, 1H), 0.90 (t, 3H), 0.60 (m, 2H), 0.35 (m, 2H) |
| 1-083 | nPr | Cl | Cl | CH₂CCH | (400 MHz, CDCl₃ δ, ppm) 10.40 (br, s, 1H), 8.32 (s, 1H), 7.68 (d, 1H), 7.50 (d, 1H), 4.83 (d, 2H), 4.41 (d, 2H), 2.54 (t, 1H), 2.03 (m, 2H), 0.98 (t, 3H) |

TABLE 1-continued

Compounds of the formula (I) according to the invention in which Q is Q1, R is CH=N—OR¹ and the other radicals have the meanings given in Table 1

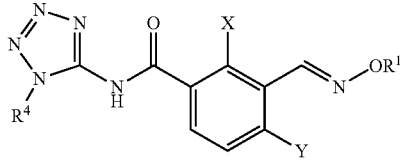

| No. | R⁴ | X | Y | R¹ | Physical data (¹H-NMR) |
|---|---|---|---|---|---|
| 1-084 | nPr | Cl | Cl | CH₂CH=CH₂ | |
| 1-085 | nPr | Cl | Cl | CH₂CH(Me)₂ | (400 MHz, d⁶-DMSO δ, ppm) 11.76 (br, s, 1H), 8.38 (s, 1H), 7.76 (d, 1H), 7.72 (d, 1H), 4.28 (t, 2H), 3.92 (d, 2H), 2.01 (m, 1H), 1.86 (m, 2H), 0.93 (d, 6H), 0.85 (t, 3H) |
| 1-086 | nPr | Cl | Cl | CH₂CH=C(Me)₂ | (400 MHz, CDCl₃ δ, ppm) 11.5 (br, s, 1H), 8.21 (s, 1H), 7.58 (d, 1H), 7.42 (d, 1H), 5.50 (t, 1H), 4.75 (d, 2H), 4.38 (t, 2H), 1.92 (m, 2H), 1.79 (s, 3H), 1.75 (s, 3H), 0.92 (t, 3H) |
| 1-087 | nPr | Cl | Cl | CH₂CH₂OMe | |
| 1-088 | nPr | Cl | Cl | CH₂CN | |
| 1-089 | nPr | Cl | Cl | CH₂CH₂SMe | |
| 1-090 | nPr | Cl | Cl | CH₂CF₃ | |
| 1-091 | nPr | Cl | Cl | CH₂CHF₂ | |
| 1-092 | nPr | Cl | SO₂Me | Me | (400 MHz, CDCl₃ δ, ppm) 8.27 (s, 1H), 7.92 (d, 1H), 7.78 (d, 1H), 4.19 (t, 2H), 3.97 (s, 3H), 3.23 (s, 3H), 1.88 (m, 2H), 2.03 (m, 2H), 0.92 (t, 3H) |
| 1-093 | nPr | Cl | SO₂Me | Et | (400 MHz, CDCl₃ δ, ppm) 8.30 (s, 1H), 7.92 (d, 1H), 7.78 (d, 1H), 4.21 (q, 2H), 4.20 (t, 2H), 3.23 (s, 3H), 1.88 (m, 2H), 1.32 (t, 3H), 0.92 (t, 3H) |
| 1-094 | nPr | Cl | SO₂Me | nPr | |
| 1-095 | nPr | Cl | SO₂Me | CH₂cPr | (400 MHz, CDCl₃ δ, ppm) 8.33 (s, 1H), 7.92 (d, 1H), 7.78 (d, 1H), 4.20 (q, 2H), 3.98 (d, 2H), 3.23 (s, 3H), 1.88 (m, 2H), 1.18 (m, 1H), 0.92 (t, 3H), 0.62 (m, 2H), 0.30 (m, 2H) |
| 1-096 | nPr | Cl | SO₂Me | CH₂CCH | (400 MHz, CDCl₃ δ, ppm) 8.35 (s, 1H), 7.92 (d, 1H), 7.80 (d, 1H), 4.74 (d, 2H), 4.20 (q, 2H), 3.23 (s, 3H), 1.88 (m, 2H), 0.92 (t, 3H) |
| 1-097 | nPr | Cl | SO₂Me | CH₂CH=CH₂ | |
| 1-098 | nPr | Cl | SO₂Me | CH₂CH(Me)₂ | (400 MHz, d⁶-DMSO δ, ppm) 8.49 (s, 1H), 8.07 (d, 1H), 7.96 (d, 1H), 4.25 (t, 2H), 3.90 (d, 2H), 3.32 (s, 3H), 1.98 (m, 1H), 1.95 (m, 2H), 0.98 (d, 6H), 0.85 (t, 3H) |
| 1-099 | nPr | Cl | SO₂Me | CH₂CH=C(Me)₂ | (400 MHz, CDCl₃ δ, ppm) 8.25 (s, 1H), 7.92 (d, 1H), 7.75 (d, 1H), 5.42 (t, 1H), 4.65 (d, 2H), 4.20 (t, 2H), 3.20 (s, 3H), 1.90 (m, 1H), 1.75 (s, 3H), 1.68 (s, 3H), 0.92 (t, 3H) |
| 1-100 | nPr | Cl | SO₂Me | CH₂CH₂OMe | |
| 1-101 | nPr | Cl | SO₂Me | CH₂CN | |
| 1-102 | nPr | Cl | SO₂Me | CH₂CH₂SMe | |
| 1-103 | nPr | Cl | SO₂Me | CH₂CF₃ | |
| 1-104 | nPr | Cl | SO₂Me | CH₂CHF₂ | |
| 1-105 | nPr | SO₂Me | Cl | Me | |
| 1-106 | nPr | SO₂Me | Cl | Et | |
| 1-107 | nPr | SO₂Me | Cl | nPr | |
| 1-108 | nPr | SO₂Me | Cl | CH₂cPr | |
| 1-109 | nPr | SO₂Me | Cl | CH₂CCH | |
| 1-110 | nPr | SO₂Me | Cl | CH₂CH=CH₂ | |
| 1-111 | nPr | SO₂Me | Cl | CH₂CH(Me)₂ | |
| 1-112 | nPr | SO₂Me | Cl | CH₂CH=C(Me)₂ | |
| 1-113 | nPr | SO₂Me | Cl | CH₂CH₂OMe | |
| 1-114 | nPr | SO₂Me | Cl | CH₂CN | |
| 1-115 | nPr | SO₂Me | Cl | CH₂CH₂SMe | |
| 1-116 | nPr | SO₂Me | Cl | CH₂CF₃ | |
| 1-117 | nPr | SO₂Me | Cl | CH₂CHF₂ | |

TABLE 2

Compounds of the formula (I) according to the invention in which Q is Q2, R is CH=N—OR¹ and the other radicals have the meanings given in Table 2

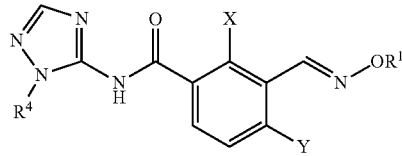

| No. | R⁴ | X | Y | R¹ | Physical data (¹H-NMR) |
|---|---|---|---|---|---|
| 2-001 | Me | Cl | Cl | Me | |
| 2-002 | Me | Cl | Cl | Et | (400 MHz, CDCl₃ δ, ppm) 10.70 (br, s, 1H), 8.22 (s, 1H), 7.45 (s, 1H), 7.30 (d, 2H), 4.29 (q, 2H), 3.79 (s, 3H), 1.25 (t, 3H) |
| 2-003 | Me | Cl | Cl | nPr | |
| 2-004 | Me | Cl | Cl | CH₂cPr | |
| 2-005 | Me | Cl | Cl | CH₂CCH | |
| 2-006 | Me | Cl | Cl | CH₂CH=CH₂ | |
| 2-007 | Me | Cl | Cl | CH₂CH(Me)₂ | |
| 2-008 | Me | Cl | Cl | CH₂CH=C(Me)₂ | |
| 2-009 | Me | Cl | Cl | CH₂CH₂OMe | |
| 2-010 | Me | Cl | Cl | CH₂CN | |
| 2-011 | Me | Cl | Cl | CH₂CH₂SMe | |
| 2-012 | Me | Cl | Cl | CH₂CF₃ | |
| 2-013 | Me | Cl | Cl | CH₂CHF₂ | |
| 2-014 | Me | Cl | SO₂Me | Me | |
| 2-015 | Me | Cl | SO₂Me | Et | (400 MHz, CDCl₃ δ, ppm) 11.30 (br, s, 1H), 8.39 (s, 1H), |

TABLE 2-continued

Compounds of the formula (I) according to the invention in which Q is Q2, R is CH=N—OR¹ and the other radicals have the meanings given in Table 2

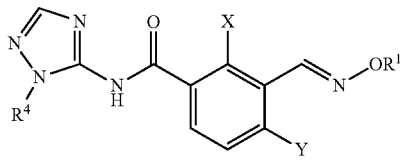

| No. | R⁴ | X | Y | R¹ | Physical data (¹H-NMR) |
|---|---|---|---|---|---|
| | | | | | 8.10 (d, 1H), 7.81 (d, 1H), 7.62 (s, 1H), 4.27 (q, 2H), 3.87 (s, 3H), 3.26 (s, 3H), 1.35 (t, 3H) |
| 2-016 | Me | Cl | SO₂Me | nPr | |
| 2-017 | Me | Cl | SO₂Me | CH₂cPr | |
| 2-018 | Me | Cl | SO₂Me | CH₂CCH | |
| 2-019 | Me | Cl | SO₂Me | CH₂CH=CH₂ | |
| 2-020 | Me | Cl | SO₂Me | CH₂CH(Me)₂ | |
| 2-021 | Me | Cl | SO₂Me | CH₂CH=C(Me)₂ | |
| 2-022 | Me | Cl | SO₂Me | CH₂CH₂OMe | |
| 2-023 | Me | Cl | SO₂Me | CH₂CN | |
| 2-024 | Me | Cl | SO₂Me | CH₂CH₂SMe | |
| 2-025 | Me | Cl | SO₂Me | CH₂CF₃ | |
| 2-026 | Me | Cl | SO₂Me | CH₂CHF₂ | |
| 2-027 | Me | SO₂Me | Cl | Me | |
| 2-028 | Me | SO₂Me | Cl | Et | |
| 2-029 | Me | SO₂Me | Cl | nPr | |
| 2-030 | Me | SO₂Me | Cl | CH₂cPr | |
| 2-031 | Me | SO₂Me | Cl | CH₂CCH | |
| 2-032 | Me | SO₂Me | Cl | CH₂CH=CH₂ | |
| 2-033 | Me | SO₂Me | Cl | CH₂CH(Me)₂ | |
| 2-034 | Me | SO₂Me | Cl | CH₂CH=C(Me)₂ | |
| 2-035 | Me | SO₂Me | Cl | CH₂CH₂OMe | |
| 2-036 | Me | SO₂Me | Cl | CH₂CN | |
| 2-037 | Me | SO₂Me | Cl | CH₂CH₂SMe | |
| 2-038 | Me | SO₂Me | Cl | CH₂CF₃ | |
| 2-039 | Me | SO₂Me | Cl | CH₂CHF₂ | |
| 2-040 | Et | Cl | Cl | Me | |
| 2-041 | Et | Cl | Cl | Et | |
| 2-042 | Et | Cl | Cl | nPr | |
| 2-043 | Et | Cl | Cl | CH₂cPr | |
| 2-044 | Et | Cl | Cl | CH₂CCH | |
| 2-045 | Et | Cl | Cl | CH₂CH=CH₂ | |
| 2-046 | Et | Cl | Cl | CH₂CH(Me)₂ | |
| 2-047 | Et | Cl | Cl | CH₂CH=C(Me)₂ | |
| 2-048 | Et | Cl | Cl | CH₂CH₂OMe | |
| 2-049 | Et | Cl | Cl | CH₂CN | |
| 2-050 | Et | Cl | Cl | CH₂CH₂SMe | |
| 2-051 | Et | Cl | Cl | CH₂CF₃ | |
| 2-052 | Et | Cl | Cl | CH₂CHF₂ | |
| 2-053 | Et | Cl | SO₂Me | Me | |
| 2-054 | Et | Cl | SO₂Me | Et | |
| 2-055 | Et | Cl | SO₂Me | nPr | |
| 2-056 | Et | Cl | SO₂Me | CH₂cPr | |
| 2-057 | Et | Cl | SO₂Me | CH₂CCH | |
| 2-058 | Et | Cl | SO₂Me | CH₂CH=CH₂ | |
| 2-059 | Et | Cl | SO₂Me | CH₂CH(Me)₂ | |
| 2-060 | Et | Cl | SO₂Me | CH₂CH=C(Me)₂ | |
| 2-061 | Et | Cl | SO₂Me | CH₂CH₂OMe | |
| 2-062 | Et | Cl | SO₂Me | CH₂CN | |
| 2-063 | Et | Cl | SO₂Me | CH₂CH₂SMe | |
| 2-064 | Et | Cl | SO₂Me | CH₂CF₃ | |
| 2-065 | Et | Cl | SO₂Me | CH₂CHF₂ | |
| 2-066 | Et | SO₂Me | Cl | Me | |
| 2-067 | Et | SO₂Me | Cl | Et | |
| 2-068 | Et | SO₂Me | Cl | nPr | |
| 2-069 | Et | SO₂Me | Cl | CH₂cPr | |
| 2-070 | Et | SO₂Me | Cl | CH₂CCH | |
| 2-071 | Et | SO₂Me | Cl | CH₂CH=CH₂ | |
| 2-072 | Et | SO₂Me | Cl | CH₂CH(Me)₂ | |
| 2-073 | Et | SO₂Me | Cl | CH₂CH=C(Me)₂ | |
| 2-074 | Et | SO₂Me | Cl | CH₂CH₂OMe | |
| 2-075 | Et | SO₂Me | Cl | CH₂CN | |

TABLE 2-continued

Compounds of the formula (I) according to the invention in which Q is Q2, R is CH=N—OR¹ and the other radicals have the meanings given in Table 2

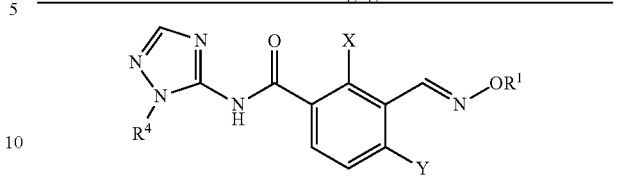

| No. | R⁴ | X | Y | R¹ | Physical data (¹H-NMR) |
|---|---|---|---|---|---|
| 2-076 | Et | SO₂Me | Cl | CH₂CH₂SMe | |
| 2-077 | Et | SO₂Me | Cl | CH₂CF₃ | |
| 2-078 | Et | SO₂Me | Cl | CH₂CHF₂ | |
| 2-079 | nPr | Cl | Cl | Me | |
| 2-080 | nPr | Cl | Cl | Et | |
| 2-081 | nPr | Cl | Cl | nPr | |
| 2-082 | nPr | Cl | Cl | CH₂cPr | |
| 2-083 | nPr | Cl | Cl | CH₂CCH | |
| 2-084 | nPr | Cl | Cl | CH₂CH=CH₂ | |
| 2-085 | nPr | Cl | Cl | CH₂CH(Me)₂ | |
| 2-086 | nPr | Cl | Cl | CH₂CH=C(Me)₂ | |
| 2-087 | nPr | Cl | Cl | CH₂CH₂OMe | |
| 2-088 | nPr | Cl | Cl | CH₂CN | |
| 2-089 | nPr | Cl | Cl | CH₂CH₂SMe | |
| 2-090 | nPr | Cl | Cl | CH₂CF₃ | |
| 2-091 | nPr | Cl | Cl | CH₂CHF₂ | |
| 2-092 | nPr | Cl | SO₂Me | Me | |
| 2-093 | nPr | Cl | SO₂Me | Et | |
| 2-094 | nPr | Cl | SO₂Me | nPr | |
| 2-095 | nPr | Cl | SO₂Me | CH₂cPr | |
| 2-096 | nPr | Cl | SO₂Me | CH₂CCH | |
| 2-097 | nPr | Cl | SO₂Me | CH₂CH=CH₂ | |
| 2-098 | nPr | Cl | SO₂Me | CH₂CH(Me)₂ | |
| 2-099 | nPr | Cl | SO₂Me | CH₂CH=C(Me)₂ | |
| 2-100 | nPr | Cl | SO₂Me | CH₂CH₂OMe | |
| 2-101 | nPr | Cl | SO₂Me | CH₂CN | |
| 2-102 | nPr | Cl | SO₂Me | CH₂CH₂SMe | |
| 2-103 | nPr | Cl | SO₂Me | CH₂CF₃ | |
| 2-104 | nPr | Cl | SO₂Me | CH₂CHF₂ | |
| 2-105 | nPr | SO₂Me | Cl | Me | |
| 2-106 | nPr | SO₂Me | Cl | Et | |
| 2-107 | nPr | SO₂Me | Cl | nPr | |
| 2-108 | nPr | SO₂Me | Cl | CH₂cPr | |
| 2-109 | nPr | SO₂Me | Cl | CH₂CCH | |
| 2-110 | nPr | SO₂Me | Cl | CH₂CH=CH₂ | |
| 2-111 | nPr | SO₂Me | Cl | CH₂CH(Me)₂ | |
| 2-112 | nPr | SO₂Me | Cl | CH₂CH=C(Me)₂ | |
| 2-113 | nPr | SO₂Me | Cl | CH₂CH₂OMe | |
| 2-114 | nPr | SO₂Me | Cl | CH₂CN | |
| 2-115 | nPr | SO₂Me | Cl | CH₂CH₂SMe | |
| 2-116 | nPr | SO₂Me | Cl | CH₂CF₃ | |
| 2-117 | nPr | SO₂Me | Cl | CH₂CHF₂ | |

TABLE 3

Compounds of the formula (I) according to the invention in which Q is Q3, R is CH=N—OR¹ and the other radicals have the meanings given in Table 3

| No. | R⁵ | X | Y | R¹ | Physical data (¹H-NMR) |
|---|---|---|---|---|---|
| 3-001 | Me | Cl | Cl | Me | (400 MHz, CDCl₃ δ, ppm) 8.24 (s, 1H), 8.20 (br, s, 1H), 7.67 |

TABLE 3-continued

Compounds of the formula (I) according to the invention in which Q is Q3, R is CH=N—OR$^1$ and the other radicals have the meanings given in Table 3

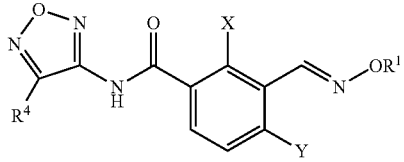
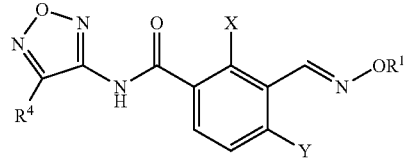

| No. | R$^5$ | X | Y | R$^1$ | Physical data ($^1$H-NMR) |
|---|---|---|---|---|---|
| 3-002 | Me | Cl | Cl | Et | (d, 1H), 7.52 (d, 1H), 4.05 (s, 1H), 2.49 (s, 3H) (400 MHz, CDCl$_3$ δ, ppm) 8.25 (s, 1H), 8.19 (br, s, 1H), 7.66 (d, 1H), 7.52 (d, 1H), 4.29 (q, 2H), 2.48 (s, 3H), 1.36 (t, 3H) |
| 3-003 | Me | Cl | Cl | nPr | |
| 3-004 | Me | Cl | Cl | CH$_2$cPr | (400 MHz, CDCl$_3$ δ, ppm) 8.30 (s, 1H), 8.19 (br, s, 1H), 7.66 (d, 1H), 7.51 (d, 1H), 4.06 (d, 2H), 2.49 (s, 3H), 1.25 (m, 1H), 0.61 (m, 2H), 0.37 (m, 2H) |
| 3-005 | Me | Cl | Cl | CH$_2$CCH | (400 MHz, CDCl$_3$ δ, ppm) 8.32 (s, 1H), 8.20 (br, s, 1H), 7.68 (d, 1H), 7.52 (d, 1H), 4.84 (d, 2H), 2.54 (m, 1H), 2.49 (s, 3H) |
| 3-006 | Me | Cl | Cl | CH$_2$CH=CH$_2$ | |
| 3-007 | Me | Cl | Cl | CH$_2$CH(Me)$_2$ | |
| 3-008 | Me | Cl | Cl | CH$_2$CH=C(Me)$_2$ | |
| 3-009 | Me | Cl | Cl | CH$_2$CH$_2$OMe | |
| 3-010 | Me | Cl | Cl | CH$_2$CN | |
| 3-011 | Me | Cl | Cl | CH$_2$CH$_2$SMe | |
| 3-012 | Me | Cl | Cl | CH$_2$CF$_3$ | |
| 3-013 | Me | Cl | Cl | CH$_2$CHF$_2$ | |
| 3-014 | Me | Cl | SO$_2$Me | Me | (400 MHz, CDCl$_3$ δ, ppm) 8.73 (br, s, 1H), 8.28 (s, 1H), 7.98 (d, 1H), 7.79 (d, 1H), 4.01 (s, 3H), 3.27 (s, 3H), 2.50 (s, 3H) |
| 3-015 | Me | Cl | SO$_2$Me | Et | (400 MHz, CDCl$_3$ δ, ppm) 8.58 (br, s, 1H), 8.31 (s, 1H), 8.01 (d, 1H), 7.81 (d, 1H), 4.25 (q, 2H), 3.25 (s, 3H), 2.50 (s, 3H), 1.32 (t, 3H) |
| 3-016 | Me | Cl | SO$_2$Me | nPr | |
| 3-017 | Me | Cl | SO$_2$Me | CH$_2$cPr | (400 MHz, CDCl$_3$ δ, ppm) 8.75 (br, s, 1H), 8.32 (s, 1H), 7.97 (d, 1H), 7.78 (d, 1H), 4.01 (d, 2H), 3.25 (s, 3H), 2.50 (s, 3H), 1.18 (m, 1H), 0.60 (m, 2H), 0.32 (m, 2H) |
| 3-018 | Me | Cl | SO$_2$Me | CH$_2$CCH | (400 MHz, CDCl$_3$ δ, ppm) 8.42 (s, 1H), 8.31 (br, s, 1H), 8.11 (d, 1H), 7.88 (d, 1H), 4.78 (d, 2H), 3.29 (s, 3H), 2.50 (s, 3H), 2.50 (t, 1H), 1.18 (m, 1H), 0.60 (m, 2H), 0.32 (m, 2H) |
| 3-019 | Me | Cl | SO$_2$Me | CH$_2$CH=CH$_2$ | |
| 3-020 | Me | Cl | SO$_2$Me | CH$_2$CH(Me)$_2$ | (400 MHz, CDCl$_3$ δ, ppm) 8.74 (br, s, 1H), 8.30 (s, 1H), 7.96 (d, 1H), 7.78 (d, 1H), 3.96 (d, 2H), 3.24 (s, 3H), 2.50 (s, 3H), 2.02 (m, 1H), 0.97 (d, 6H) |
| 3-021 | Me | Cl | SO$_2$Me | CH$_2$CH=C(Me)$_2$ | |
| 3-022 | Me | Cl | SO$_2$Me | CH$_2$CH$_2$OMe | |
| 3-023 | Me | Cl | SO$_2$Me | CH$_2$CN | |
| 3-024 | Me | Cl | SO$_2$Me | CH$_2$CH$_2$SMe | |
| 3-025 | Me | Cl | SO$_2$Me | CH$_2$CF$_3$ | |
| 3-026 | Me | Cl | SO$_2$Me | CH$_2$CHF$_2$ | |
| 3-027 | Me | SO$_2$Me | Cl | Me | |
| 3-028 | Me | SO$_2$Me | Cl | Et | |
| 3-029 | Me | SO$_2$Me | Cl | nPr | |
| 3-030 | Me | SO$_2$Me | Cl | CH$_2$cPr | |
| 3-031 | Me | SO$_2$Me | Cl | CH$_2$CCH | |
| 3-032 | Me | SO$_2$Me | Cl | CH$_2$CH=CH$_2$ | |
| 3-033 | Me | SO$_2$Me | Cl | CH$_2$CH(Me)$_2$ | |
| 3-034 | Me | SO$_2$Me | Cl | CH$_2$CH=C(Me)$_2$ | |
| 3-035 | Me | SO$_2$Me | Cl | CH$_2$CH$_2$OMe | |
| 3-036 | Me | SO$_2$Me | Cl | CH$_2$CN | |
| 3-037 | Me | SO$_2$Me | Cl | CH$_2$CH$_2$SMe | |
| 3-038 | Me | SO$_2$Me | Cl | CH$_2$CF$_3$ | |
| 3-039 | Me | SO$_2$Me | Cl | CH$_2$CHF$_2$ | |
| 3-040 | OMe | Cl | Cl | Me | |
| 3-041 | OMe | Cl | Cl | Et | |
| 3-042 | OMe | Cl | Cl | nPr | |
| 3-043 | OMe | Cl | Cl | CH$_2$cPr | |
| 3-044 | OMe | Cl | Cl | CH$_2$CCH | |
| 3-045 | OMe | Cl | Cl | CH$_2$CH=CH$_2$ | |
| 3-046 | OMe | Cl | Cl | CH$_2$CH(Me)$_2$ | |
| 3-047 | OMe | Cl | Cl | CH$_2$CH=C(Me)$_2$ | |
| 3-048 | OMe | Cl | Cl | CH$_2$CH$_2$OMe | |
| 3-049 | OMe | Cl | Cl | CH$_2$CN | |
| 3-050 | OMe | Cl | Cl | CH$_2$CH$_2$SMe | |
| 3-051 | OMe | Cl | Cl | CH$_2$CF$_3$ | |
| 3-052 | OMe | Cl | Cl | CH$_2$CHF$_2$ | |
| 3-053 | OMe | Cl | SO$_2$Me | Me | |
| 3-054 | OMe | Cl | SO$_2$Me | Et | |
| 3-055 | OMe | Cl | SO$_2$Me | nPr | |
| 3-056 | OMe | Cl | SO$_2$Me | CH$_2$cPr | |
| 3-057 | OMe | Cl | SO$_2$Me | CH$_2$CCH | |
| 3-058 | OMe | Cl | SO$_2$Me | CH$_2$CH=CH$_2$ | |
| 3-059 | OMe | Cl | SO$_2$Me | CH$_2$CH(Me)$_2$ | |
| 3-060 | OMe | Cl | SO$_2$Me | CH$_2$CH=C(Me)$_2$ | |
| 3-061 | OMe | Cl | SO$_2$Me | CH$_2$CH$_2$OMe | |
| 3-062 | OMe | Cl | SO$_2$Me | CH$_2$CN | |
| 3-063 | OMe | Cl | SO$_2$Me | CH$_2$CH$_2$SMe | |
| 3-064 | OMe | Cl | SO$_2$Me | CH$_2$CF$_3$ | |
| 3-065 | OMe | Cl | SO$_2$Me | CH$_2$CHF$_2$ | |
| 3-066 | OMe | SO$_2$Me | Cl | Me | |
| 3-067 | OMe | SO$_2$Me | Cl | Et | |
| 3-068 | OMe | SO$_2$Me | Cl | nPr | |
| 3-069 | OMe | SO$_2$Me | Cl | CH$_2$cPr | |
| 3-070 | OMe | SO$_2$Me | Cl | CH$_2$CCH | |
| 3-071 | OMe | SO$_2$Me | Cl | CH$_2$CH=CH$_2$ | |
| 3-072 | OMe | SO$_2$Me | Cl | CH$_2$CH(Me)$_2$ | |
| 3-073 | OMe | SO$_2$Me | Cl | CH$_2$CH=C(Me)$_2$ | |

TABLE 3-continued

Compounds of the formula (I) according to the invention in which Q is Q3, R is CH=N—OR$^1$ and the other radicals have the meanings given in Table 3

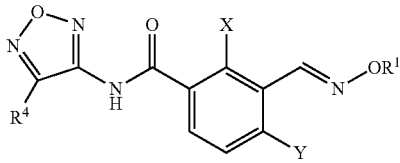

| No. | R$^5$ | X | Y | R$^1$ | Physical data ($^1$H-NMR) |
|---|---|---|---|---|---|
| 3-074 | OMe | SO$_2$Me | Cl | CH$_2$CH$_2$OMe | |
| 3-075 | OMe | SO$_2$Me | Cl | CH$_2$CN | |
| 3-076 | OMe | SO$_2$Me | Cl | CH$_2$CH$_2$SMe | |
| 3-077 | OMe | SO$_2$Me | Cl | CH$_2$CF$_3$ | |
| 3-078 | OMe | SO$_2$Me | Cl | CH$_2$CHF$_2$ | |
| 3-079 | Cl | Cl | Cl | Me | |
| 3-080 | Cl | Cl | Cl | Et | |
| 3-081 | Cl | Cl | Cl | nPr | |
| 3-082 | Cl | Cl | Cl | CH$_2$cPr | |
| 3-083 | Cl | Cl | Cl | CH$_2$CCH | |
| 3-084 | Cl | Cl | Cl | CH$_2$CH=CH$_2$ | |
| 3-085 | Cl | Cl | Cl | CH$_2$CH(Me)$_2$ | |
| 3-086 | Cl | Cl | Cl | CH$_2$CH=C(Me)$_2$ | |
| 3-087 | Cl | Cl | Cl | CH$_2$CH$_2$OMe | |
| 3-088 | Cl | Cl | Cl | CH$_2$CN | |
| 3-089 | Cl | Cl | Cl | CH$_2$CH$_2$SMe | |
| 3-090 | Cl | Cl | Cl | CH$_2$CF$_3$ | |
| 3-091 | Cl | Cl | Cl | CH$_2$CHF$_2$ | |
| 3-092 | Cl | Cl | SO$_2$Me | Me | |
| 3-093 | Cl | Cl | SO$_2$Me | Et | |
| 3-094 | Cl | Cl | SO$_2$Me | nPr | |
| 3-095 | Cl | Cl | SO$_2$Me | CH$_2$cPr | |
| 3-096 | Cl | Cl | SO$_2$Me | CH$_2$CCH | |
| 3-097 | Cl | Cl | SO$_2$Me | CH$_2$CH=CH$_2$ | |
| 3-098 | Cl | Cl | SO$_2$Me | CH$_2$CH(Me)$_2$ | |
| 3-099 | Cl | Cl | SO$_2$Me | CH$_2$CH=C(Me)$_2$ | |
| 3-100 | Cl | Cl | SO$_2$Me | CH$_2$CH$_2$OMe | |
| 3-101 | Cl | Cl | SO$_2$Me | CH$_2$CN | |
| 3-102 | Cl | Cl | SO$_2$Me | CH$_2$CH$_2$SMe | |
| 3-103 | Cl | Cl | SO$_2$Me | CH$_2$CF$_3$ | |
| 3-104 | Cl | Cl | SO$_2$Me | CH$_2$CHF$_2$ | |
| 3-105 | Cl | SO$_2$Me | Cl | Me | |
| 3-106 | Cl | SO$_2$Me | Cl | Et | |
| 3-107 | Cl | SO$_2$Me | Cl | nPr | |
| 3-108 | Cl | SO$_2$Me | Cl | CH$_2$cPr | |
| 3-109 | Cl | SO$_2$Me | Cl | CH$_2$CCH | |
| 3-110 | Cl | SO$_2$Me | Cl | CH$_2$CH=CH$_2$ | |
| 3-111 | Cl | SO$_2$Me | Cl | CH$_2$CH(Me)$_2$ | |
| 3-112 | Cl | SO$_2$Me | Cl | CH$_2$CH=C(Me)$_2$ | |
| 3-113 | Cl | SO$_2$Me | Cl | CH$_2$CH$_2$OMe | |
| 3-114 | Cl | SO$_2$Me | Cl | CH$_2$CN | |
| 3-115 | Cl | SO$_2$Me | Cl | CH$_2$CH$_2$SMe | |
| 3-116 | Cl | SO$_2$Me | Cl | CH$_2$CF$_3$ | |
| 3-117 | Cl | SO$_2$Me | Cl | CH$_2$CHF$_2$ | |

TABLE 4

Compounds of the formula (I) according to the invention in which Q is Q4, R is CH=N—OR$^1$ and the other radicals have the meanings given in Table 4

| No. | R$^6$ | X | Y | R$^1$ | Physical data ($^1$H-NMR) |
|---|---|---|---|---|---|
| 4-001 | Me | Cl | Cl | Me | 400 MHz, DMSO-d$_6$, 12.31 (bs, 1H); 8.34 (s, 1H), 7.70 (s, 2H), 3.94 (s, 3H), 2.50 (s, 3H) |
| 4-002 | Me | Cl | Cl | Et | |
| 4-003 | Me | Cl | Cl | nPr | |
| 4-004 | Me | Cl | Cl | CH$_2$cPr | |
| 4-005 | Me | Cl | Cl | CH$_2$CCH | |
| 4-006 | Me | Cl | Cl | CH$_2$CH=CH$_2$ | |
| 4-007 | Me | Cl | Cl | CH$_2$CH(Me)$_2$ | |
| 4-008 | Me | Cl | Cl | CH$_2$CH=C(Me)$_2$ | |
| 4-009 | Me | Cl | Cl | CH$_2$CH$_2$OMe | |
| 4-010 | Me | Cl | Cl | CH$_2$CN | |
| 4-011 | Me | Cl | Cl | CH$_2$CH$_2$SMe | |
| 4-012 | Me | Cl | Cl | CH$_2$CF$_3$ | |
| 4-013 | Me | Cl | Cl | CH$_2$CHF$_2$ | |
| 4-014 | Me | Cl | SO$_2$Me | Me | |
| 4-015 | Me | Cl | SO$_2$Me | Et | |
| 4-016 | Me | Cl | SO$_2$Me | nPr | |
| 4-017 | Me | Cl | SO$_2$Me | CH$_2$cPr | 400 MHz, DMSO-d$_6$, 12.48 (bs, 1H); 8.49 (s, 1H), 8.09 (d, 1H), 7.97 (d, 1H), 3.97 (d, 2H), 3.38 (s, 3H), 2.50 (s, 3H), 1.16 (m, 1H), 0.55 (m, 2H), 0.28 (m, 2H). |
| 4-018 | Me | Cl | SO$_2$Me | CH$_2$CCH | |
| 4-019 | Me | Cl | SO$_2$Me | CH$_2$CH=CH$_2$ | |
| 4-020 | Me | Cl | SO$_2$Me | CH$_2$CH(Me)$_2$ | |
| 4-021 | Me | Cl | SO$_2$Me | CH$_2$CH=C(Me)$_2$ | |
| 4-022 | Me | Cl | SO$_2$Me | CH$_2$CH$_2$OMe | |
| 4-023 | Me | Cl | SO$_2$Me | CH$_2$CN | |
| 4-024 | Me | Cl | SO$_2$Me | CH$_2$CH$_2$SMe | |
| 4-025 | Me | Cl | SO$_2$Me | CH$_2$CF$_3$ | |
| 4-026 | Me | Cl | SO$_2$Me | CH$_2$CHF$_2$ | |
| 4-027 | Me | SO$_2$Me | Cl | Me | |
| 4-028 | Me | SO$_2$Me | Cl | Et | |
| 4-029 | Me | SO$_2$Me | Cl | nPr | |
| 4-030 | Me | SO$_2$Me | Cl | CH$_2$cPr | |
| 4-031 | Me | SO$_2$Me | Cl | CH$_2$CCH | |
| 4-032 | Me | SO$_2$Me | Cl | CH$_2$CH=CH$_2$ | |
| 4-033 | Me | SO$_2$Me | Cl | CH$_2$CH(Me)$_2$ | |
| 4-034 | Me | SO$_2$Me | Cl | CH$_2$CH=C(Me)$_2$ | |
| 4-035 | Me | SO$_2$Me | Cl | CH$_2$CH$_2$OMe | |
| 4-036 | Me | SO$_2$Me | Cl | CH$_2$CN | |
| 4-037 | Me | SO$_2$Me | Cl | CH$_2$CH$_2$SMe | |
| 4-038 | Me | SO$_2$Me | Cl | CH$_2$CF$_3$ | |
| 4-039 | Me | SO$_2$Me | Cl | CH$_2$CHF$_2$ | |
| 4-040 | Et | Cl | Cl | Me | (400 MHz, CDCl$_3$ δ, ppm) 8.21 (s, 1H), 7.63 (d, |

TABLE 4-continued

Compounds of the formula (I) according to the invention in which Q is Q4, R is CH=N—OR¹ and the other radicals have the meanings given in Table 4

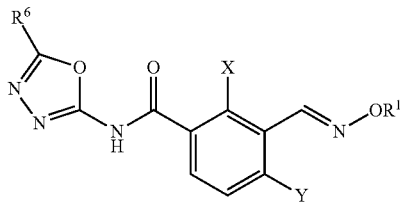

| No. | R⁶ | X | Y | R¹ | Physical data (¹H-NMR) |
|---|---|---|---|---|---|
| | | | | | 1H), 7.42 (d, 1H), 4.03 (s, 3H), 2.86 (q, 2H), 1.38 (t, 3H) |
| 4-041 | Et | Cl | Cl | Et | |
| 4-042 | Et | Cl | Cl | nPr | |
| 4-043 | Et | Cl | Cl | CH₂cPr | |
| 4-044 | Et | Cl | Cl | CH₂CCH | |
| 4-045 | Et | Cl | Cl | CH₂CH=CH₂ | |
| 4-046 | Et | Cl | Cl | CH₂CH(Me)₂ | |
| 4-047 | Et | Cl | Cl | CH₂CH=C(Me)₂ | |
| 4-048 | Et | Cl | Cl | CH₂CH₂OMe | |
| 4-049 | Et | Cl | Cl | CH₂CN | |
| 4-050 | Et | Cl | Cl | CH₂CH₂SMe | |
| 4-051 | Et | Cl | Cl | CH₂CF₃ | |
| 4-052 | Et | Cl | Cl | CH₂CHF₂ | |
| 4-053 | Et | Cl | SO₂Me | Me | |
| 4-054 | Et | Cl | SO₂Me | Et | |
| 4-055 | Et | Cl | SO₂Me | nPr | |
| 4-056 | Et | Cl | SO₂Me | CH₂cPr | |
| 4-057 | Et | Cl | SO₂Me | CH₂CCH | |
| 4-058 | Et | Cl | SO₂Me | CH₂CH=CH₂ | |
| 4-059 | Et | Cl | SO₂Me | CH₂CH(Me)₂ | |
| 4-060 | Et | Cl | SO₂Me | CH₂CH=C(Me)₂ | |
| 4-061 | Et | Cl | SO₂Me | CH₂CH₂OMe | |
| 4-062 | Et | Cl | SO₂Me | CH₂CN | |
| 4-063 | Et | Cl | SO₂Me | CH₂CH₂SMe | |
| 4-064 | Et | Cl | SO₂Me | CH₂CF₃ | |
| 4-065 | Et | Cl | SO₂Me | CH₂CHF₂ | |
| 4-066 | Et | SO₂Me | Cl | Me | |
| 4-067 | Et | SO₂Me | Cl | Et | |
| 4-068 | Et | SO₂Me | Cl | nPr | |
| 4-069 | Et | SO₂Me | Cl | CH₂cPr | |
| 4-070 | Et | SO₂Me | Cl | CH₂CCH | |
| 4-071 | Et | SO₂Me | Cl | CH₂CH=CH₂ | |
| 4-072 | Et | SO₂Me | Cl | CH₂CH(Me)₂ | |
| 4-073 | Et | SO₂Me | Cl | CH₂CH=C(Me)₂ | |
| 4-074 | Et | SO₂Me | Cl | CH₂CH₂OMe | |
| 4-075 | Et | SO₂Me | Cl | CH₂CN | |
| 4-076 | Et | SO₂Me | Cl | CH₂CH₂SMe | |
| 4-077 | Et | SO₂Me | Cl | CH₂CF₃ | |
| 4-078 | Et | SO₂Me | Cl | CH₂CHF₂ | |
| 4-079 | CH₂OMe | Cl | Cl | Me | |
| 4-080 | CH₂OMe | Cl | Cl | Et | |
| 4-081 | CH₂OMe | Cl | Cl | nPr | |
| 4-082 | CH₂OMe | Cl | Cl | CH₂cPr | |
| 4-083 | CH₂OMe | Cl | Cl | CH₂CCH | |
| 4-084 | CH₂OMe | Cl | Cl | CH₂CH=CH₂ | |
| 4-085 | CH₂OMe | Cl | Cl | CH₂CH(Me)₂ | |
| 4-086 | CH₂OMe | Cl | Cl | CH₂CH=C(Me)₂ | |
| 4-087 | CH₂OMe | Cl | Cl | CH₂CH₂OMe | |
| 4-088 | CH₂OMe | Cl | Cl | CH₂CN | |
| 4-089 | CH₂OMe | Cl | Cl | CH₂CH₂SMe | |
| 4-090 | CH₂OMe | Cl | Cl | CH₂CF₃ | |
| 4-091 | CH₂OMe | Cl | Cl | CH₂CHF₂ | |
| 4-092 | CH₂OMe | Cl | SO₂Me | Me | (400 MHz, CDCl₃ δ, ppm) 8.26 (s, 1H), 7.95 (d, 1H), 7.84 (d, 1H), 4.49 (s, 2H), 4.00 (s, 3H), 3.42 (s, 3H), 3.24 (s, 3H) |
| 4-093 | CH₂OMe | Cl | SO₂Me | Et | (400 MHz, CDCl₃ δ, ppm) 8.36 (s, 1H), 8.12 (d, 1H), 7.85 (d, 1H), 4.60 (s, 2H), 4.27 (q, 2H), 3.49 (s, 3H), 3.28 (s, 3H), 1.35 (t, 3H) |
| 4-094 | CH₂OMe | Cl | SO₂Me | nPr | |
| 4-095 | CH₂OMe | Cl | SO₂Me | CH₂cPr | |
| 4-096 | CH₂OMe | Cl | SO₂Me | CH₂CCH | 400 MHz, DMSO-d₆ 12.49 (bs, 1H); 8.57 (s, 1H), 8.10 (d, 1H), 8.00 (d, 1H), 4.81 (s, 2H), 3.38 (s, 3H), 3.32 (s, 1H), 2.50 (s, 3H) |
| 4-097 | CH₂OMe | Cl | SO₂Me | CH₂CH=CH₂ | |
| 4-098 | CH₂OMe | Cl | SO₂Me | CH₂CH(Me)₂ | |
| 4-099 | CH₂OMe | Cl | SO₂Me | CH₂CH=C(Me)₂ | |
| 4-100 | CH₂OMe | Cl | SO₂Me | CH₂CH₂OMe | |
| 4-101 | CH₂OMe | Cl | SO₂Me | CH₂CN | |
| 4-102 | CH₂OMe | Cl | SO₂Me | CH₂CH₂SMe | |
| 4-103 | CH₂OMe | Cl | SO₂Me | CH₂CF₃ | |
| 4-104 | CH₂OMe | Cl | SO₂Me | CH₂CHF₂ | |
| 4-105 | CH₂OMe | SO₂Me | Cl | Me | |
| 4-106 | CH₂OMe | SO₂Me | Cl | Et | |
| 4-107 | CH₂OMe | SO₂Me | Cl | nPr | |
| 4-108 | CH₂OMe | SO₂Me | Cl | CH₂cPr | |
| 4-109 | CH₂OMe | SO₂Me | Cl | CH₂CCH | |
| 4-110 | CH₂OMe | SO₂Me | Cl | CH₂CH=CH₂ | |
| 4-111 | CH₂OMe | SO₂Me | Cl | CH₂CH(Me)₂ | |
| 4-112 | CH₂OMe | SO₂Me | Cl | CH₂CH=C(Me)₂ | |
| 4-113 | CH₂OMe | SO₂Me | Cl | CH₂CH₂OMe | |
| 4-114 | CH₂OMe | SO₂Me | Cl | CH₂CN | |
| 4-115 | CH₂OMe | SO₂Me | Cl | CH₂CH₂SMe | |
| 4-116 | CH₂OMe | SO₂Me | Cl | CH₂CF₃ | |
| 4-117 | CH₂OMe | SO₂Me | Cl | CH₂CHF₂ | |

TABLE 5

Compounds of the formula (I) according to the invention in which Q is Q1, R is $CH_2-O-N=CR^2R^3$ and the other radicals have the meanings given in Table 5

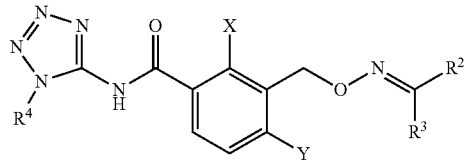

| No. | $R^4$ | X | Y | $R^2$ | $R^3$ | Physical data ($^1$H-NMR) |
|---|---|---|---|---|---|---|
| 5-001 | Me | Cl | Cl | H | H | |
| 5-002 | Me | Cl | Cl | H | Me | |
| 5-003 | Me | Cl | Cl | H | Et | |
| 5-004 | Me | Cl | Cl | Me | Me | (400 MHz, CDCl$_3$ δ, ppm) 10.55 (br, s, 1H), 7.65 (d, 1H), 7.49 (d, 1H), 5.38 (s, 2H), 4.11 (s, 3H), 1.86 (s, 3H), 1.83 (s, 3H) |
| 5-005 | Me | Cl | Cl | Et | Et | |
| 5-006 | Me | Cl | Cl | H | Ph | |
| 5-007 | Me | Cl | Cl | H | CH$_2$OMe | |
| 5-008 | Me | Cl | Cl | H | CH$_2$cPr | |
| 5-009 | Me | Cl | Cl | H | CH$_2$CH$_2$OMe | |
| 5-010 | Me | Cl | Cl | Me | Ph | |
| 5-011 | Me | Cl | Cl | Me | CH$_2$OMe | |
| 5-012 | Me | Cl | Cl | Me | CH$_2$cPr | |
| 5-013 | Me | Cl | Cl | Me | CH$_2$CH$_2$OMe | |
| 5-014 | Me | Cl | SO$_2$Me | H | H | |
| 5-015 | Me | Cl | SO$_2$Me | H | Me | |
| 5-016 | Me | Cl | SO$_2$Me | H | Et | |
| 5-017 | Me | Cl | SO$_2$Me | Me | Me | (400 MHz, CDCl$_3$ δ, ppm) 10.80 (br, s, 1H), 8.11 (d, 1H), 7.77 (d, 1H), 5.69 (s, 2H), 4.12 (s, 3H), 3.36 (s, 3H), 1.82 (s, 3H), 1.81 (s, 3H) |
| 5-018 | Me | Cl | SO$_2$Me | Et | Et | |
| 5-019 | Me | Cl | SO$_2$Me | H | Ph | |
| 5-020 | Me | Cl | SO$_2$Me | H | CH$_2$OMe | |
| 5-021 | Me | Cl | SO$_2$Me | H | CH$_2$cPr | |
| 5-022 | Me | Cl | SO$_2$Me | H | CH$_2$CH$_2$OMe | |
| 5-023 | Me | Cl | SO$_2$Me | Me | Ph | |
| 5-024 | Me | Cl | SO$_2$Me | Me | CH$_2$OMe | |
| 5-025 | Me | Cl | SO$_2$Me | Me | CH$_2$cPr | |
| 5-026 | Me | Cl | SO$_2$Me | Me | CH$_2$CH$_2$OMe | |
| 5-027 | Me | SO$_2$Me | Cl | H | H | |
| 5-028 | Me | SO$_2$Me | Cl | H | Me | |
| 5-029 | Me | SO$_2$Me | Cl | H | Et | |
| 5-030 | Me | SO$_2$Me | Cl | Me | Me | |
| 5-031 | Me | SO$_2$Me | Cl | Et | Et | |
| 5-032 | Me | SO$_2$Me | Cl | H | Ph | |
| 5-033 | Me | SO$_2$Me | Cl | H | CH$_2$OMe | |
| 5-034 | Me | SO$_2$Me | Cl | H | CH$_2$cPr | |
| 5-035 | Me | SO$_2$Me | Cl | H | CH$_2$CH$_2$OMe | |
| 5-036 | Me | SO$_2$Me | Cl | Me | Ph | |
| 5-037 | Me | SO$_2$Me | Cl | Me | CH$_2$OMe | |
| 5-038 | Me | SO$_2$Me | Cl | Me | CH$_2$cPr | |
| 5-039 | Me | SO$_2$Me | Cl | Me | CH$_2$CH$_2$OMe | |
| 5-040 | Et | Cl | Cl | H | H | |
| 5-041 | Et | Cl | Cl | H | Me | |
| 5-042 | Et | Cl | Cl | H | Et | |
| 5-043 | Et | Cl | Cl | Me | Me | (400 MHz, CDCl$_3$ δ, ppm) 10.04 (br, s, 1H), 7.66 (d, 1H), 7.49 (d, 1H), 5.39 (s, 2H), 4.48 (q, 2H), 1.88 (s, 3H), 1.83 (s, 3H), 1.62 (t, 3H) |
| 5-044 | Et | Cl | Cl | Et | Et | |
| 5-045 | Et | Cl | Cl | H | Ph | |
| 5-046 | Et | Cl | Cl | H | CH$_2$OMe | |
| 5-047 | Et | Cl | Cl | H | CH$_2$cPr | |
| 5-048 | Et | Cl | Cl | H | CH$_2$CH$_2$OMe | |
| 5-049 | Et | Cl | Cl | Me | Ph | |
| 5-050 | Et | Cl | Cl | Me | CH$_2$OMe | |
| 5-051 | Et | Cl | Cl | Me | CH$_2$cPr | |
| 5-052 | Et | Cl | Cl | Me | CH$_2$CH$_2$OMe | |
| 5-053 | Et | Cl | SO$_2$Me | H | H | |
| 5-054 | Et | Cl | SO$_2$Me | H | Me | |
| 5-055 | Et | Cl | SO$_2$Me | H | Et | |
| 5-056 | Et | Cl | SO$_2$Me | Me | Me | (400 MHz, CDCl$_3$ δ, ppm) 10.38 (br, s, 1H), 8.16 (d, 1H), 7.78 (d, 1H), 5.70 (s, 2H), 4.48 (q, 2H), 3.35 (s, 3H), 1.80 (s, 3H), 1.79 (s, 3H), 1.64 (t, 3H) |
| 5-057 | Et | Cl | SO$_2$Me | Et | Et | |
| 5-058 | Et | Cl | SO$_2$Me | H | Ph | |
| 5-059 | Et | Cl | SO$_2$Me | H | CH$_2$OMe | |
| 5-060 | Et | Cl | SO$_2$Me | H | CH$_2$cPr | |
| 5-061 | Et | Cl | SO$_2$Me | H | CH$_2$CH$_2$OMe | |
| 5-062 | Et | Cl | SO$_2$Me | Me | Ph | |
| 5-063 | Et | Cl | SO$_2$Me | Me | CH$_2$OMe | |
| 5-064 | Et | Cl | SO$_2$Me | Me | CH$_2$cPr | |
| 5-065 | Et | Cl | SO$_2$Me | Me | CH$_2$CH$_2$OMe | |
| 5-066 | Et | SO$_2$Me | Cl | H | H | |
| 5-067 | Et | SO$_2$Me | Cl | H | Me | |
| 5-068 | Et | SO$_2$Me | Cl | H | Et | |
| 5-069 | Et | SO$_2$Me | Cl | Me | Me | |
| 5-070 | Et | SO$_2$Me | Cl | Et | Et | |
| 5-071 | Et | SO$_2$Me | Cl | H | Ph | |
| 5-072 | Et | SO$_2$Me | Cl | H | CH$_2$OMe | |
| 5-073 | Et | SO$_2$Me | Cl | H | CH$_2$cPr | |
| 5-074 | Et | SO$_2$Me | Cl | H | CH$_2$CH$_2$OMe | |
| 5-075 | Et | SO$_2$Me | Cl | Me | Ph | |
| 5-076 | Et | SO$_2$Me | Cl | Me | CH$_2$OMe | |
| 5-077 | Et | SO$_2$Me | Cl | Me | CH$_2$cPr | |
| 5-078 | Et | SO$_2$Me | Cl | Me | CH$_2$CH$_2$OMe | |
| 5-079 | nPr | Cl | Cl | H | H | |
| 5-080 | nPr | Cl | Cl | H | Me | |
| 5-081 | nPr | Cl | Cl | H | Et | |
| 5-082 | nPr | Cl | Cl | Me | Me | (400 MHz, CDCl$_3$ δ, ppm) 10.32 (br, s, 1H), 7.63 (d, 1H), 7.47 (d, 1H), 5.38 (s, 2H), 4.41 (t, 2H), 2.02 (m, 2H), 1.87 (s, 3H), 1.83 (s, 3H), 0.98 (t, 3H) |
| 5-083 | nPr | Cl | Cl | Et | Et | |
| 5-084 | nPr | Cl | Cl | H | Ph | |
| 5-085 | nPr | Cl | Cl | H | CH$_2$OMe | |
| 5-086 | nPr | Cl | Cl | H | CH$_2$cPr | |
| 5-087 | nPr | Cl | Cl | H | CH$_2$CH$_2$OMe | |
| 5-088 | nPr | Cl | Cl | Me | Ph | |
| 5-089 | nPr | Cl | Cl | Me | CH$_2$OMe | |
| 5-090 | nPr | Cl | Cl | Me | CH$_2$cPr | |
| 5-091 | nPr | Cl | Cl | Me | CH$_2$CH$_2$OMe | |
| 5-092 | nPr | Cl | SO$_2$Me | H | H | |
| 5-093 | nPr | Cl | SO$_2$Me | H | Me | |
| 5-094 | nPr | Cl | SO$_2$Me | H | Et | |

TABLE 5-continued

Compounds of the formula (I) according to the invention in which Q is Q1, R is CH$_2$—O—N═CR$^2$R$^3$ and the other radicals have the meanings given in Table 5

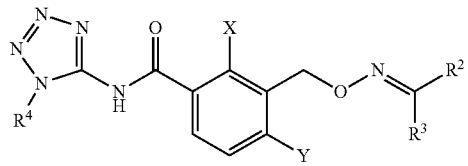

| No. | R$^4$ | X | Y | R$^2$ | R$^3$ | Physical data ($^1$H-NMR) |
|---|---|---|---|---|---|---|
| 5-095 | nPr | Cl | SO$_2$Me | Me | Me | (400 MHz, CDCl$_3$ δ, ppm) 10.50 (br, s, 1H), 8.15 (d, 1H), 7.80 (d, 1H), 5.70 (s, 2H), 4.44 (t, 2H), 3.36 (s, 3H), 2.05 (m, 2H), 1.82 (s, 3H), 1.81 (s, 3H), 1.00 (t, 3H) |
| 5-096 | nPr | Cl | SO$_2$Me | Et | Et | |
| 5-097 | nPr | Cl | SO$_2$Me | H | Ph | |
| 5-098 | nPr | Cl | SO$_2$Me | H | CH$_2$OMe | |
| 5-099 | nPr | Cl | SO$_2$Me | H | CH$_2$cPr | |
| 5-100 | nPr | Cl | SO$_2$Me | H | CH$_2$CH$_2$OMe | |
| 5-101 | nPr | Cl | SO$_2$Me | Me | Ph | |
| 5-102 | nPr | Cl | SO$_2$Me | Me | CH$_2$OMe | |
| 5-103 | nPr | Cl | SO$_2$Me | Me | CH$_2$cPr | |
| 5-104 | nPr | Cl | SO$_2$Me | Me | CH$_2$CH$_2$OMe | |
| 5-105 | nPr | SO$_2$Me | Cl | H | H | |
| 5-106 | nPr | SO$_2$Me | Cl | H | Me | |
| 5-107 | nPr | SO$_2$Me | Cl | H | Et | |
| 5-108 | nPr | SO$_2$Me | Cl | Me | Me | |
| 5-109 | nPr | SO$_2$Me | Cl | Et | Et | |
| 5-110 | nPr | SO$_2$Me | Cl | H | Ph | |
| 5-111 | nPr | SO$_2$Me | Cl | H | CH$_2$OMe | |
| 5-112 | nPr | SO$_2$Me | Cl | H | CH$_2$cPr | |
| 5-113 | nPr | SO$_2$Me | Cl | H | CH$_2$CH$_2$OMe | |
| 5-114 | nPr | SO$_2$Me | Cl | Me | Ph | |
| 5-115 | nPr | SO$_2$Me | Cl | Me | CH$_2$OMe | |
| 5-116 | nPr | SO$_2$Me | Cl | Me | CH$_2$cPr | |
| 5-117 | nPr | SO$_2$Me | Cl | Me | CH$_2$CH$_2$OMe | |

TABLE 6

Compounds of the formula (I) according to the invention in which Q is Q2, R is CH$_2$—O—N═CR$^2$R$^3$ and the other radicals have the meanings given in Table 6

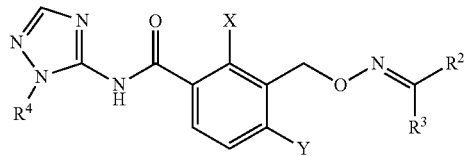

| No. | R$^4$ | X | Y | R$^2$ | R$^3$ | Physical data ($^1$H-NMR) |
|---|---|---|---|---|---|---|
| 6-001 | Me | Cl | Cl | H | H | |
| 6-002 | Me | Cl | Cl | H | Me | |
| 6-003 | Me | Cl | Cl | H | Et | |
| 6-004 | Me | Cl | Cl | Me | Me | (400 MHz, CDCl$_3$ δ, ppm) 7.52 (d, 1H), 7.46 (s, 1H), 7.42 (d, 1H), 5.38 (s, 2H), 3.88 (s, 3H), 1.88 (s, 3H), 1.83 (s, 3H) |
| 6-005 | Me | Cl | Cl | Et | Et | |
| 6-006 | Me | Cl | Cl | H | Ph | |
| 6-007 | Me | Cl | Cl | H | CH$_2$OMe | |

TABLE 6-continued

Compounds of the formula (I) according to the invention in which Q is Q2, R is CH$_2$—O—N═CR$^2$R$^3$ and the other radicals have the meanings given in Table 6

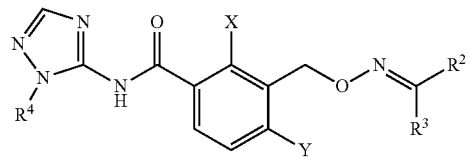

| No. | R$^4$ | X | Y | R$^2$ | R$^3$ | Physical data ($^1$H-NMR) |
|---|---|---|---|---|---|---|
| 6-008 | Me | Cl | Cl | H | CH$_2$cPr | |
| 6-009 | Me | Cl | Cl | H | CH$_2$CH$_2$OMe | |
| 6-010 | Me | Cl | Cl | Me | Ph | |
| 6-011 | Me | Cl | Cl | Me | CH$_2$OMe | |
| 6-012 | Me | Cl | Cl | Me | CH$_2$cPr | |
| 6-013 | Me | Cl | Cl | Me | CH$_2$CH$_2$OMe | |
| 6-014 | Me | Cl | SO$_2$Me | H | H | |
| 6-015 | Me | Cl | SO$_2$Me | H | Me | |
| 6-016 | Me | Cl | SO$_2$Me | H | Et | |
| 6-017 | Me | Cl | SO$_2$Me | Me | Me | (400 MHz, CDCl$_3$ δ, ppm) 8.14 (d, 1H), 7.69 (d, 1H), 7.27 (s, 1H), 5.73 (s, 2H), 3.89 (s, 3H), 3.37 (s, 3H), 1.84 (s, 3H) |
| 6-018 | Me | Cl | SO$_2$Me | Et | Et | |
| 6-019 | Me | Cl | SO$_2$Me | H | Ph | |
| 6-020 | Me | Cl | SO$_2$Me | H | CH$_2$OMe | |
| 6-021 | Me | Cl | SO$_2$Me | H | CH$_2$cPr | |
| 6-022 | Me | Cl | SO$_2$Me | H | CH$_2$CH$_2$OMe | |
| 6-023 | Me | Cl | SO$_2$Me | Me | Ph | |
| 6-024 | Me | Cl | SO$_2$Me | Me | CH$_2$OMe | |
| 6-025 | Me | Cl | SO$_2$Me | Me | CH$_2$cPr | |
| 6-026 | Me | Cl | SO$_2$Me | Me | CH$_2$CH$_2$OMe | |
| 6-027 | Me | SO$_2$Me | Cl | H | H | |
| 6-028 | Me | SO$_2$Me | Cl | H | Me | |
| 6-029 | Me | SO$_2$Me | Cl | H | Et | |
| 6-030 | Me | SO$_2$Me | Cl | Me | Me | |
| 6-031 | Me | SO$_2$Me | Cl | Et | Et | |
| 6-032 | Me | SO$_2$Me | Cl | H | Ph | |
| 6-033 | Me | SO$_2$Me | Cl | H | CH$_2$OMe | |
| 6-034 | Me | SO$_2$Me | Cl | H | CH$_2$cPr | |
| 6-035 | Me | SO$_2$Me | Cl | H | CH$_2$CH$_2$OMe | |
| 6-036 | Me | SO$_2$Me | Cl | Me | Ph | |
| 6-037 | Me | SO$_2$Me | Cl | Me | CH$_2$OMe | |
| 6-038 | Me | SO$_2$Me | Cl | Me | CH$_2$cPr | |
| 6-039 | Me | SO$_2$Me | Cl | Me | CH$_2$CH$_2$OMe | |
| 6-040 | Et | Cl | Cl | H | H | |
| 6-041 | Et | Cl | Cl | H | Me | |
| 6-042 | Et | Cl | Cl | H | Et | |
| 6-043 | Et | Cl | Cl | Me | Me | |
| 6-044 | Et | Cl | Cl | Et | Et | |
| 6-045 | Et | Cl | Cl | H | Ph | |
| 6-046 | Et | Cl | Cl | H | CH$_2$OMe | |
| 6-047 | Et | Cl | Cl | H | CH$_2$cPr | |
| 6-048 | Et | Cl | Cl | H | CH$_2$CH$_2$OMe | |
| 6-049 | Et | Cl | Cl | Me | Ph | |
| 6-050 | Et | Cl | Cl | Me | CH$_2$OMe | |
| 6-051 | Et | Cl | Cl | Me | CH$_2$cPr | |
| 6-052 | Et | Cl | Cl | Me | CH$_2$CH$_2$OMe | |
| 6-053 | Et | Cl | SO$_2$Me | H | H | |
| 6-054 | Et | Cl | SO$_2$Me | H | Me | |
| 6-055 | Et | Cl | SO$_2$Me | H | Et | |
| 6-056 | Et | Cl | SO$_2$Me | Me | Me | |
| 6-057 | Et | Cl | SO$_2$Me | Et | Et | |
| 6-058 | Et | Cl | SO$_2$Me | H | Ph | |
| 6-059 | Et | Cl | SO$_2$Me | H | CH$_2$OMe | |
| 6-060 | Et | Cl | SO$_2$Me | H | CH$_2$cPr | |
| 6-061 | Et | Cl | SO$_2$Me | H | CH$_2$CH$_2$OMe | |
| 6-062 | Et | Cl | SO$_2$Me | Me | Ph | |
| 6-063 | Et | Cl | SO$_2$Me | Me | CH$_2$OMe | |
| 6-064 | Et | Cl | SO$_2$Me | Me | CH$_2$cPr | |
| 6-065 | Et | Cl | SO$_2$Me | Me | CH$_2$CH$_2$OMe | |

TABLE 6-continued

Compounds of the formula (I) according to the invention in which Q is Q2, R is $CH_2$—O—N=$CR^2R^3$ and the other radicals have the meanings given in Table 6

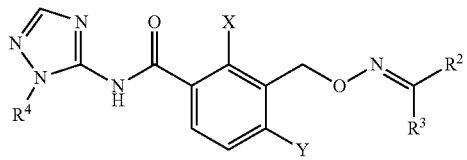

| No. | $R^4$ | X | Y | $R^2$ | $R^3$ | Physical data ($^1$H-NMR) |
|---|---|---|---|---|---|---|
| 6-066 | Et | SO$_2$Me | Cl | H | H | |
| 6-067 | Et | SO$_2$Me | Cl | H | Me | |
| 6-068 | Et | SO$_2$Me | Cl | H | Et | |
| 6-069 | Et | SO$_2$Me | Cl | Me | Me | |
| 6-070 | Et | SO$_2$Me | Cl | Et | Et | |
| 6-071 | Et | SO$_2$Me | Cl | H | Ph | |
| 6-072 | Et | SO$_2$Me | Cl | H | CH$_2$OMe | |
| 6-073 | Et | SO$_2$Me | Cl | H | CH$_2$cPr | |
| 6-074 | Et | SO$_2$Me | Cl | H | CH$_2$CH$_2$OMe | |
| 6-075 | Et | SO$_2$Me | Cl | Me | Ph | |
| 6-076 | Et | SO$_2$Me | Cl | Me | CH$_2$OMe | |
| 6-077 | Et | SO$_2$Me | Cl | Me | CH$_2$cPr | |
| 6-078 | Et | SO$_2$Me | Cl | Me | CH$_2$CH$_2$OMe | |
| 6-079 | nPr | Cl | Cl | H | H | |
| 6-080 | nPr | Cl | Cl | H | Me | |
| 6-081 | nPr | Cl | Cl | H | Et | |
| 6-082 | nPr | Cl | Cl | Me | Me | |
| 6-083 | nPr | Cl | Cl | Et | Et | |
| 6-084 | nPr | Cl | Cl | H | Ph | |
| 6-085 | nPr | Cl | Cl | H | CH$_2$OMe | |
| 6-086 | nPr | Cl | Cl | H | CH$_2$cPr | |
| 6-087 | nPr | Cl | Cl | H | CH$_2$CH$_2$OMe | |
| 6-088 | nPr | Cl | Cl | Me | Ph | |
| 6-089 | nPr | Cl | Cl | Me | CH$_2$OMe | |
| 6-090 | nPr | Cl | Cl | Me | CH$_2$cPr | |
| 6-091 | nPr | Cl | Cl | Me | CH$_2$CH$_2$OMe | |
| 6-092 | nPr | Cl | SO$_2$Me | H | H | |
| 6-093 | nPr | Cl | SO$_2$Me | H | Me | |
| 6-094 | nPr | Cl | SO$_2$Me | H | Et | |
| 6-095 | nPr | Cl | SO$_2$Me | Me | Me | |
| 6-096 | nPr | Cl | SO$_2$Me | Et | Et | |
| 6-097 | nPr | Cl | SO$_2$Me | H | Ph | |
| 6-098 | nPr | Cl | SO$_2$Me | H | CH$_2$OMe | |
| 6-099 | nPr | Cl | SO$_2$Me | H | CH$_2$cPr | |
| 6-100 | nPr | Cl | SO$_2$Me | H | CH$_2$CH$_2$OMe | |
| 6-101 | nPr | Cl | SO$_2$Me | Me | Ph | |
| 6-102 | nPr | Cl | SO$_2$Me | Me | CH$_2$OMe | |
| 6-103 | nPr | Cl | SO$_2$Me | Me | CH$_2$cPr | |
| 6-104 | nPr | Cl | SO$_2$Me | Me | CH$_2$CH$_2$OMe | |
| 6-105 | nPr | SO$_2$Me | Cl | H | H | |
| 6-106 | nPr | SO$_2$Me | Cl | H | Me | |
| 6-107 | nPr | SO$_2$Me | Cl | H | Et | |
| 6-108 | nPr | SO$_2$Me | Cl | Me | Me | |
| 6-109 | nPr | SO$_2$Me | Cl | Et | Et | |
| 6-110 | nPr | SO$_2$Me | Cl | H | Ph | |
| 6-111 | nPr | SO$_2$Me | Cl | H | CH$_2$OMe | |
| 6-112 | nPr | SO$_2$Me | Cl | H | CH$_2$cPr | |
| 6-113 | nPr | SO$_2$Me | Cl | H | CH$_2$CH$_2$OMe | |
| 6-114 | nPr | SO$_2$Me | Cl | Me | Ph | |
| 6-115 | nPr | SO$_2$Me | Cl | Me | CH$_2$OMe | |
| 6-116 | nPr | SO$_2$Me | Cl | Me | CH$_2$cPr | |
| 6-117 | nPr | SO$_2$Me | Cl | Me | CH$_2$CH$_2$OMe | |

TABLE 7

Compound of the formula (I) according to the invention in which Q is Q3, R is $CH_2$—O—N=$CR^2R^3$ and the other radicals have the meanings given in Table 7

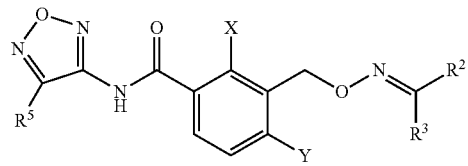

| No. | $R^5$ | X | Y | $R^2$ | $R^3$ | Physical data ($^1$H-NMR) |
|---|---|---|---|---|---|---|
| 7-001 | Me | Cl | Cl | H | H | |
| 7-002 | Me | Cl | Cl | H | Me | |
| 7-003 | Me | Cl | Cl | H | Et | |
| 7-004 | Me | Cl | Cl | Me | Me | |
| 7-005 | Me | Cl | Cl | Et | Et | |
| 7-006 | Me | Cl | Cl | H | Ph | |
| 7-007 | Me | Cl | Cl | H | CH$_2$OMe | |
| 7-008 | Me | Cl | Cl | H | CH$_2$cPr | |
| 7-009 | Me | Cl | Cl | H | CH$_2$CH$_2$OMe | |
| 7-010 | Me | Cl | Cl | Me | Ph | |
| 7-011 | Me | Cl | Cl | Me | CH$_2$OMe | |
| 7-012 | Me | Cl | Cl | Me | CH$_2$cPr | |
| 7-013 | Me | Cl | Cl | Me | CH$_2$CH$_2$OMe | |
| 7-014 | Me | Cl | SO$_2$Me | H | H | |
| 7-015 | Me | Cl | SO$_2$Me | H | Me | |
| 7-016 | Me | Cl | SO$_2$Me | H | Et | |
| 7-017 | Me | Cl | SO$_2$Me | Me | Me | (400 MHz, CDCl$_3$ δ, ppm) 8.60 (br, s, 1H), 8.00 (d, 1H), 7.72 (d, 1H), 5.69 (s, 2H), 3.33 (s, 3H), 2.52 (s, 3H), 1.82 (s, 3H), 181 (s, 3H) |
| 7-018 | Me | Cl | SO$_2$Me | Et | Et | |
| 7-019 | Me | Cl | SO$_2$Me | H | Ph | |
| 7-020 | Me | Cl | SO$_2$Me | H | CH$_2$OMe | |
| 7-021 | Me | Cl | SO$_2$Me | H | CH$_2$cPr | |
| 7-022 | Me | Cl | SO$_2$Me | H | CH$_2$CH$_2$OMe | |
| 7-023 | Me | Cl | SO$_2$Me | Me | Ph | |
| 7-024 | Me | Cl | SO$_2$Me | Me | CH$_2$OMe | |
| 7-025 | Me | Cl | SO$_2$Me | Me | CH$_2$cPr | |
| 7-026 | Me | Cl | SO$_2$Me | Me | CH$_2$CH$_2$OMe | |
| 7-027 | Me | SO$_2$Me | Cl | H | H | |
| 7-028 | Me | SO$_2$Me | Cl | H | Me | |
| 7-029 | Me | SO$_2$Me | Cl | H | Et | |
| 7-030 | Me | SO$_2$Me | Cl | Me | Me | |
| 7-031 | Me | SO$_2$Me | Cl | Et | Et | |
| 7-032 | Me | SO$_2$Me | Cl | H | Ph | |
| 7-033 | Me | SO$_2$Me | Cl | H | CH$_2$OMe | |
| 7-034 | Me | SO$_2$Me | Cl | H | CH$_2$cPr | |
| 7-035 | Me | SO$_2$Me | Cl | H | CH$_2$CH$_2$OMe | |
| 7-036 | Me | SO$_2$Me | Cl | Me | Ph | |
| 7-037 | Me | SO$_2$Me | Cl | Me | CH$_2$OMe | |
| 7-038 | Me | SO$_2$Me | Cl | Me | CH$_2$cPr | |
| 7-039 | Me | SO$_2$Me | Cl | Me | CH$_2$CH$_2$OMe | |
| 7-040 | OMe | Cl | Cl | H | H | |
| 7-041 | OMe | Cl | Cl | H | Me | |
| 7-042 | OMe | Cl | Cl | H | Et | |
| 7-043 | OMe | Cl | Cl | Me | Me | |
| 7-044 | OMe | Cl | Cl | Et | Et | |
| 7-045 | OMe | Cl | Cl | H | Ph | |
| 7-046 | OMe | Cl | Cl | H | CH$_2$OMe | |
| 7-047 | OMe | Cl | Cl | H | CH$_2$cPr | |
| 7-048 | OMe | Cl | Cl | H | CH$_2$CH$_2$OMe | |
| 7-049 | OMe | Cl | Cl | Me | Ph | |
| 7-050 | OMe | Cl | Cl | Me | CH$_2$OMe | |
| 7-051 | OMe | Cl | Cl | Me | CH$_2$cPr | |
| 7-052 | OMe | Cl | Cl | Me | CH$_2$CH$_2$OMe | |
| 7-053 | OMe | Cl | SO$_2$Me | H | H | |
| 7-054 | OMe | Cl | SO$_2$Me | H | Me | |
| 7-055 | OMe | Cl | SO$_2$Me | H | Et | |
| 7-056 | OMe | Cl | SO$_2$Me | Me | Me | |
| 7-057 | OMe | Cl | SO$_2$Me | Et | Et | |
| 7-058 | OMe | Cl | SO$_2$Me | H | Ph | |

TABLE 7-continued

Compound of the formula (I) according to the invention in which Q is Q3, R is CH₂—O—N=CR²R³ and the other radicals have the meanings given in Table 7

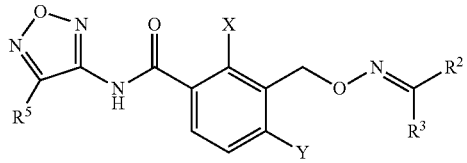

| No. | R⁵ | X | Y | R² | R³ | Physical data (¹H-NMR) |
|---|---|---|---|---|---|---|
| 7-059 | OMe | Cl | SO₂Me | H | CH₂OMe | |
| 7-060 | OMe | Cl | SO₂Me | H | CH₂cPr | |
| 7-061 | OMe | Cl | SO₂Me | H | CH₂CH₂OMe | |
| 7-062 | OMe | Cl | SO₂Me | Me | Ph | |
| 7-063 | OMe | Cl | SO₂Me | Me | CH₂OMe | |
| 7-064 | OMe | Cl | SO₂Me | Me | CH₂cPr | |
| 7-065 | OMe | Cl | SO₂Me | Me | CH₂CH₂OMe | |
| 7-066 | OMe | SO₂Me | Cl | H | H | |
| 7-067 | OMe | SO₂Me | Cl | H | Me | |
| 7-068 | OMe | SO₂Me | Cl | H | Et | |
| 7-069 | OMe | SO₂Me | Cl | Me | Me | |
| 7-070 | OMe | SO₂Me | Cl | Et | Et | |
| 7-071 | OMe | SO₂Me | Cl | H | Ph | |
| 7-072 | OMe | SO₂Me | Cl | H | CH₂OMe | |
| 7-073 | OMe | SO₂Me | Cl | H | CH₂cPr | |
| 7-074 | OMe | SO₂Me | Cl | H | CH₂CH₂OMe | |
| 7-075 | OMe | SO₂Me | Cl | Me | Ph | |
| 7-076 | OMe | SO₂Me | Cl | Me | CH₂OMe | |
| 7-077 | OMe | SO₂Me | Cl | Me | CH₂cPr | |
| 7-078 | OMe | SO₂Me | Cl | Me | CH₂CH₂OMe | |
| 7-079 | Cl | Cl | Cl | H | H | |
| 7-080 | Cl | Cl | Cl | H | Me | |
| 7-081 | Cl | Cl | Cl | H | Et | |
| 7-082 | Cl | Cl | Cl | Me | Me | |
| 7-083 | Cl | Cl | Cl | Et | Et | |
| 7-084 | Cl | Cl | Cl | H | Ph | |
| 7-085 | Cl | Cl | Cl | H | CH₂OMe | |
| 7-086 | Cl | Cl | Cl | H | CH₂cPr | |
| 7-087 | Cl | Cl | Cl | H | CH₂CH₂OMe | |
| 7-088 | Cl | Cl | Cl | Me | Ph | |
| 7-089 | Cl | Cl | Cl | Me | CH₂OMe | |
| 7-090 | Cl | Cl | Cl | Me | CH₂cPr | |
| 7-091 | Cl | Cl | Cl | Me | CH₂CH₂OMe | |
| 7-092 | Cl | Cl | SO₂Me | H | H | |
| 7-093 | Cl | Cl | SO₂Me | H | Me | |
| 7-094 | Cl | Cl | SO₂Me | H | Et | |
| 7-095 | Cl | Cl | SO₂Me | Me | Me | |
| 7-096 | Cl | Cl | SO₂Me | Et | Et | |
| 7-097 | Cl | Cl | SO₂Me | H | Ph | |
| 7-098 | Cl | Cl | SO₂Me | H | CH₂OMe | |
| 7-099 | Cl | Cl | SO₂Me | H | CH₂cPr | |
| 7-100 | Cl | Cl | SO₂Me | H | CH₂CH₂OMe | |
| 7-101 | Cl | Cl | SO₂Me | Me | Ph | |
| 7-102 | Cl | Cl | SO₂Me | Me | CH₂OMe | |
| 7-103 | Cl | Cl | SO₂Me | Me | CH₂cPr | |
| 7-104 | Cl | Cl | SO₂Me | Me | CH₂CH₂OMe | |
| 7-105 | Cl | SO₂Me | Cl | H | H | |
| 7-106 | Cl | SO₂Me | Cl | H | Me | |
| 7-107 | Cl | SO₂Me | Cl | H | Et | |
| 7-108 | Cl | SO₂Me | Cl | Me | Me | |
| 7-109 | Cl | SO₂Me | Cl | Et | Et | |
| 7-110 | Cl | SO₂Me | Cl | H | Ph | |
| 7-111 | Cl | SO₂Me | Cl | H | CH₂OMe | |
| 7-112 | Cl | SO₂Me | Cl | H | CH₂cPr | |
| 7-113 | Cl | SO₂Me | Cl | H | CH₂CH₂OMe | |
| 7-114 | Cl | SO₂Me | Cl | Me | Ph | |
| 7-115 | Cl | SO₂Me | Cl | Me | CH₂OMe | |
| 7-116 | Cl | SO₂Me | Cl | Me | CH₂cPr | |
| 7-117 | Cl | SO₂Me | Cl | Me | CH₂CH₂OMe | |

TABLE 8

Compounds of the formula (I) according to the invention in which Q is Q4, R is CH₂—O—N=CR²R³ and the other radicals have the meanings given in Table 8

| No. | R⁶ | X | Y | R² | R³ | Physical data (¹H-NMR) |
|---|---|---|---|---|---|---|
| 8-001 | Me | Cl | Cl | H | H | |
| 8-002 | Me | Cl | Cl | H | Me | |
| 8-003 | Me | Cl | Cl | H | Et | |
| 8-004 | Me | Cl | Cl | Me | Me | |
| 8-005 | Me | Cl | Cl | Et | Et | |
| 8-006 | Me | Cl | Cl | H | Ph | |
| 8-007 | Me | Cl | Cl | H | CH₂OMe | |
| 8-008 | Me | Cl | Cl | H | CH₂cPr | |
| 8-009 | Me | Cl | Cl | H | CH₂CH₂OMe | |
| 8-010 | Me | Cl | Cl | Me | Ph | |
| 8-011 | Me | Cl | Cl | Me | CH₂OMe | |
| 8-012 | Me | Cl | Cl | Me | CH₂cPr | |
| 8-013 | Me | Cl | Cl | Me | CH₂CH₂OMe | |
| 8-014 | Me | Cl | SO₂Me | H | H | 400 MHz, DMSO-d₆, 12.46 (bs, 1H); 8.11 (d, 1H), 7,.92 (d, 1H), 7.13 (d, 1H), 6.71(d, 1 H), 5.70 (s, 2H), 3.38 (s, 3H), 2.50 (s, 3H) |
| 8-015 | Me | Cl | SO₂Me | H | Me | 400 MHz, DMSO-d₆, 12.49 (bs, 1H); 8.11 (d, 1H), 7.91 (d, 1H), 7,.50 (q, 1H), 5.67 (s, 2H), 3.39 (s, 3H), 2.50 (s, 3H), 1.78 (d, 3H) |
| 8-016 | Me | Cl | SO₂Me | H | Et | |
| 8-017 | Me | Cl | SO₂Me | Me | Me | 400 MHz, DMSO-d₆, 12.45 (bs, 1H); 8.10 (d, 1H), 7.91 (d, 1H), 5.60 (s, 2H), 3.43 (s, 3H), 2.50 (s, 3H), 1.81 (s, 3H), 1.77 (s, 3H). |
| 8-018 | Me | Cl | SO₂Me | Et | Et | |
| 8-019 | Me | Cl | SO₂Me | H | Ph | |
| 8-020 | Me | Cl | SO₂Me | H | CH₂OMe | |
| 8-021 | Me | Cl | SO₂Me | H | CH₂cPr | |
| 8-022 | Me | Cl | SO₂Me | H | CH₂CH₂OMe | |
| 8-023 | Me | Cl | SO₂Me | Me | Ph | |
| 8-024 | Me | Cl | SO₂Me | Me | CH₂OMe | |
| 8-025 | Me | Cl | SO₂Me | Me | CH₂cPr | |
| 8-026 | Me | Cl | SO₂Me | Me | CH₂CH₂OMe | |
| 8-027 | Me | SO₂Me | Cl | H | H | |
| 8-028 | Me | SO₂Me | Cl | H | Me | |
| 8-029 | Me | SO₂Me | Cl | H | Et | |
| 8-030 | Me | SO₂Me | Cl | Me | Me | |
| 8-031 | Me | SO₂Me | Cl | Et | Et | |
| 8-032 | Me | SO₂Me | Cl | H | Ph | |

TABLE 8-continued

Compounds of the formula (I) according to the invention in which Q is Q4, R is CH$_2$—O—N=CR$^2$R$^3$ and the other radicals have the meanings given in Table 8

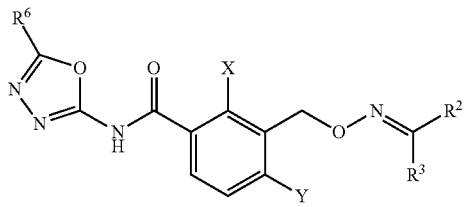

| No. | R$^6$ | X | Y | R$^2$ | R$^3$ | Physical data ($^1$H-NMR) |
|---|---|---|---|---|---|---|
| 8-033 | Me | SO$_2$Me | Cl | H | CH$_2$OMe | |
| 8-034 | Me | SO$_2$Me | Cl | H | CH$_2$cPr | |
| 8-035 | Me | SO$_2$Me | Cl | H | CH$_2$CH$_2$OMe | |
| 8-036 | Me | SO$_2$Me | Cl | Me | Ph | |
| 8-037 | Me | SO$_2$Me | Cl | Me | CH$_2$OMe | |
| 8-038 | Me | SO$_2$Me | Cl | Me | CH$_2$cPr | |
| 8-039 | Me | SO$_2$Me | Cl | Me | CH$_2$CH$_2$OMe | |
| 8-040 | Et | Cl | Cl | H | H | |
| 8-041 | Et | Cl | Cl | H | Me | |
| 8-042 | Et | Cl | Cl | H | Et | |
| 8-043 | Et | Cl | Cl | Me | Me | |
| 8-044 | Et | Cl | Cl | Et | Et | |
| 8-045 | Et | Cl | Cl | H | Ph | |
| 8-046 | Et | Cl | Cl | H | CH$_2$OMe | |
| 8-047 | Et | Cl | Cl | H | CH$_2$cPr | |
| 8-048 | Et | Cl | Cl | H | CH$_2$CH$_2$OMe | |
| 8-049 | Et | Cl | Cl | Me | Ph | |
| 8-050 | Et | Cl | Cl | Me | CH$_2$OMe | |
| 8-051 | Et | Cl | Cl | Me | CH$_2$cPr | |
| 8-052 | Et | Cl | Cl | Me | CH$_2$CH$_2$OMe | |
| 8-053 | Et | Cl | SO$_2$Me | H | H | |
| 8-054 | Et | Cl | SO$_2$Me | H | Me | |
| 8-055 | Et | Cl | SO$_2$Me | H | Et | |
| 8-056 | Et | Cl | SO$_2$Me | Me | Me | |
| 8-057 | Et | Cl | SO$_2$Me | Et | Et | |
| 8-058 | Et | Cl | SO$_2$Me | H | Ph | |
| 8-059 | Et | Cl | SO$_2$Me | H | CH$_2$OMe | |
| 8-060 | Et | Cl | SO$_2$Me | H | CH$_2$cPr | |
| 8-061 | Et | Cl | SO$_2$Me | H | CH$_2$CH$_2$OMe | |
| 8-062 | Et | Cl | SO$_2$Me | Me | Ph | |
| 8-063 | Et | Cl | SO$_2$Me | Me | CH$_2$OMe | |
| 8-064 | Et | Cl | SO$_2$Me | Me | CH$_2$cPr | |
| 8-065 | Et | Cl | SO$_2$Me | Me | CH$_2$CH$_2$OMe | |
| 8-066 | Et | SO$_2$Me | Cl | H | H | |
| 8-067 | Et | SO$_2$Me | Cl | H | Me | |
| 8-068 | Et | SO$_2$Me | Cl | H | Et | |
| 8-069 | Et | SO$_2$Me | Cl | Me | Me | |
| 8-070 | Et | SO$_2$Me | Cl | Et | Et | |
| 8-071 | Et | SO$_2$Me | Cl | H | Ph | |
| 8-072 | Et | SO$_2$Me | Cl | H | CH$_2$OMe | |
| 8-073 | Et | SO$_2$Me | Cl | H | CH$_2$cPr | |
| 8-074 | Et | SO$_2$Me | Cl | H | CH$_2$CH$_2$OMe | |
| 8-075 | Et | SO$_2$Me | Cl | Me | Ph | |
| 8-076 | Et | SO$_2$Me | Cl | Me | CH$_2$OMe | |
| 8-077 | Et | SO$_2$Me | Cl | Me | CH$_2$cPr | |
| 8-078 | Et | SO$_2$Me | Cl | Me | CH$_2$CH$_2$OMe | |
| 8-079 | CH$_2$OMe | Cl | Cl | H | H | |
| 8-080 | CH$_2$OMe | Cl | Cl | H | Me | |
| 8-081 | CH$_2$OMe | Cl | Cl | H | Et | |
| 8-082 | CH$_2$OMe | Cl | Cl | Me | Me | |
| 8-083 | CH$_2$OMe | Cl | Cl | Et | Et | |
| 8-084 | CH$_2$OMe | Cl | Cl | H | Ph | |
| 8-085 | CH$_2$OMe | Cl | Cl | H | CH$_2$OMe | |
| 8-086 | CH$_2$OMe | Cl | Cl | H | CH$_2$cPr | |
| 8-087 | CH$_2$OMe | Cl | Cl | H | CH$_2$CH$_2$OMe | |
| 8-088 | CH$_2$OMe | Cl | Cl | Me | Ph | |
| 8-089 | CH$_2$OMe | Cl | Cl | Me | CH$_2$OMe | |
| 8-090 | CH$_2$OMe | Cl | Cl | Me | CH$_2$cPr | |
| 8-091 | CH$_2$OMe | Cl | Cl | Me | CH$_2$CH$_2$OMe | |
| 8-092 | CH$_2$OMe | Cl | SO$_2$Me | H | H | |
| 8-093 | CH$_2$OMe | Cl | SO$_2$Me | H | Me | |
| 8-094 | CH$_2$OMe | Cl | SO$_2$Me | H | Et | |

TABLE 8-continued

Compounds of the formula (I) according to the invention in which Q is Q4, R is CH$_2$—O—N=CR$^2$R$^3$ and the other radicals have the meanings given in Table 8

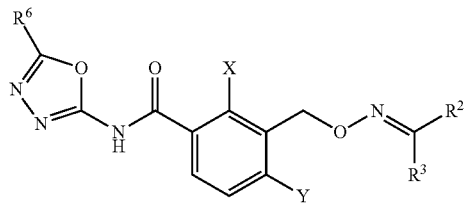

| No. | R$^6$ | X | Y | R$^2$ | R$^3$ | Physical data ($^1$H-NMR) |
|---|---|---|---|---|---|---|
| 8-095 | CH$_2$OMe | Cl | SO2Me | Me | Me | |
| 8-096 | CH$_2$OMe | Cl | SO$_2$Me | Et | Et | |
| 8-097 | CH$_2$OMe | Cl | SO$_2$Me | H | Ph | |
| 8-098 | CH$_2$OMe | Cl | SO$_2$Me | H | CH$_2$OMe | |
| 8-099 | CH$_2$OMe | Cl | SO$_2$Me | H | CH$_2$cPr | |
| 8-100 | CH$_2$OMe | Cl | SO$_2$Me | H | CH$_2$CH$_2$OMe | |
| 8-101 | CH$_2$OMe | Cl | SO$_2$Me | Me | Ph | |
| 8-102 | CH$_2$OMe | Cl | SO$_2$Me | Me | CH$_2$OMe | |
| 8-103 | CH$_2$OMe | Cl | SO$_2$Me | Me | CH$_2$cPr | |
| 8-104 | CH$_2$OMe | Cl | SO$_2$Me | Me | CH$_2$CH$_2$OMe | |
| 8-105 | CH$_2$OMe | SO$_2$Me | Cl | H | H | |
| 8-106 | CH$_2$OMe | SO$_2$Me | Cl | H | Me | |
| 8-107 | CH$_2$OMe | SO$_2$Me | Cl | H | Et | |
| 8-108 | CH$_2$OMe | SO$_2$Me | Cl | Me | Me | |
| 8-109 | CH$_2$OMe | SO$_2$Me | Cl | Et | Et | |
| 8-110 | CH$_2$OMe | SO$_2$Me | Cl | H | Ph | |
| 8-111 | CH$_2$OMe | SO$_2$Me | Cl | H | CH$_2$OMe | |
| 8-112 | CH$_2$OMe | SO$_2$Me | Cl | H | CH$_2$cPr | |
| 8-113 | CH$_2$OMe | SO$_2$Me | Cl | H | CH$_2$CH$_2$OMe | |
| 8-114 | CH$_2$OMe | SO$_2$Me | Cl | Me | Ph | |
| 8-115 | CH$_2$OMe | SO$_2$Me | Cl | Me | CH$_2$OMe | |
| 8-116 | CH$_2$OMe | SO$_2$Me | Cl | Me | CH$_2$cPr | |
| 8-117 | CH$_2$OMe | SO$_2$Me | Cl | Me | CH$_2$CH$_2$OMe | |

In the case of mixtures of E and Z isomers, only the signals of the main E isomer are stated.

B. FORMULATION EXAMPLES a) A dust is obtained by mixing 10 parts by weight of a compound of the formula (I) and/or a salt thereof and 90 parts by weight of talc as inert substance and comminuting the mixture in a hammer mill.

b) A readily water-dispersible wettable powder is obtained by mixing 25 parts by weight of a compound of the formula (I) and/or salts thereof, 64 parts by weight of kaolin-containing quartz as an inert substance, 10 parts by weight of potassium lignosulfonate and 1 part by weight of sodium oleoylmethyltaurate as a wetting agent and dispersant, and grinding the mixture in a pinned-disk mill.

c) A readily water-dispersible dispersion concentrate is obtained by mixing parts by weight of a compound of the formula (I) and/or salts thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.), and grinding the mixture in a ball mill to a fineness of below 5 microns.

d) An emulsifiable concentrate is obtained from 15 parts by weight of a compound of the formula (I) and/or salts thereof, 75 parts by weight of cyclohexanone as a solvent and 10 parts by weight of ethoxylated nonylphenol as an emulsifier.

e) Water-dispersible granules are obtained by mixing
   75 parts by weight of a compound of the formula (I) and/or salts thereof,
   10 parts by weight of calcium lignosulfonate,
   5 parts by weight of sodium laurylsulfate,
   3 parts by weight of polyvinyl alcohol and
   7 parts by weight of kaolin,
   grinding the mixture in a pinned-disk mill, and granulating the powder in a fluidized bed by spray application of water as a granulating liquid.
f) Water-dispersible granules are also obtained by homogenizing and precomminuting
   25 parts by weight of a compound of the formula (I) and/or salts thereof,
   5 parts by weight of sodium 2,2'-dinaphthylmethane-6,6'-disulfonate,
   2 parts by weight of sodium oleoylmethyltaurate,
   1 part by weight of polyvinyl alcohol,
   17 parts by weight of calcium carbonate and
   50 parts by weight of water
   in a colloid mill, then grinding the mixture in a bead mill and atomizing and drying the resulting suspension in a spray tower by means of a one-substance nozzle.

C. BIOLOGICAL EXAMPLES

1. Pre-Emergence Herbicidal Action Against Harmful Plants

Seeds of monocotyledonous and dicotyledonous weed plants and crop plants are placed in wood-fiber pots in sandy loam and covered with soil. The compounds according to the invention, formulated in the form of wettable powders (WP) or as emulsion concentrates (EC), are then applied as aqueous suspension or emulsion at a water application rate of 600 to 800 l/ha (converted) with the addition of 0.2% of wetting agent to the surface of the covering soil. After the treatment, the pots are placed in a greenhouse and kept under good growth conditions for the test plants. The damage to the test plants is assessed visually after a test period of 3 weeks by comparison with untreated controls (herbicidal activity in percent (%): 100% activity=the plants have died, 0% activity=like control plants). Here, the compounds Nos. 1-002, 1-004, 1-007, 1-008, 1-043, 1-044, 1-046, 1-047, 1-060, 1-079, 1-080, 1-082, 1-083, 1-085, 1-095, 1-096, 1-098, 1-099, 1-059, 2-015, 3-015, 3-018, 3-020, 4-001, 4-118, 5-004, 5-017, 5-043, 5-056, 5-082, 5-095, 6-017, 7-017, 8-017 and 8-014, for example, each show, at an application rate of 320 g/ha, an activity of at least 80% against *Abuthilon theophrasti* and *Amaranthus retroflexus*. The compounds Nos. 1-001, 1-005, 1-014, 1-015, 1-017, 1-018, 1-020, 1-033, 1-040, 1-041, 1-053, 1-054, 1-056, 1-057, 1-092, 1-093, 3-014, 3-015, 8-014, 8-017 and 8-015 each show, at an application rate of 320 g/ha, an activity of at least 80% against *Setaria viridis* and *Stellaria media*. The compounds Nos. 3-017, 4-092 and 6-004 show, at an application rate of 320 g/ha, an activity of at least 80% against *Amaranthus retroflexus* and *Veronica persica*.

2. Post-Emergence Herbicidal Action Against Harmful Plants

Seeds of monocotyledonous and dicotyledonous weed and crop plants are placed in sandy loam in wood-fiber pots, covered with soil and cultivated in a greenhouse under good growth conditions. 2 to 3 weeks after sowing, the test plants are treated at the one-leaf stage. The inventive compounds formulated in the form of wettable powders (WP) or as emulsion concentrates (EC) are then sprayed onto the green parts of the plants as an aqueous suspension or emulsion at a water application rate of 600 to 800 l/ha (converted) with addition of 0.2% wetting agent. After the test plants have been left to stand in the greenhouse under optimal growth conditions for about 3 weeks, the action of the formulations is assessed visually in comparison to untreated controls (herbicidal action in percent (%): 100% activity=the plants have died, 0% activity=like control plants). Here, the compounds Nos. 1-001, 1-002, 1-004, 1-005, 1-007, 1-008, 1-014, 1-015, 1-017, 1-018, 1-020, 1-033, 1-040, 1-041, 1-043, 1-044, 1-046, 1-047, 1-053, 1-054, 1-056, 1-057, 1-059, 1-060, 1-079, 1-080, 1-082, 1-083, 1-086, 1-092, 1-093, 1-095, 1-096, 1-098, 1-099, 2-015, 3-014, 3-015, 3-017, 3-018, 3-020, 5-082, 5-095, 6-017, 7-017 and 8-014 each show, at an application rate of 80 g/ha, an activity of at least 80% against *Abuthilon theophrasti*, *Amaranthus retroflexus* and *Stellaria media*. The compounds Nos. 4-092, 4-093, 5-004, 5-017, 5-043 and 5-056 each show, at an application rate of 80 g/ha, an activity of at least 80% against *Echinocloa crus galli*, *Pharbitis purpureum* and *Stellaria media*.

The invention claimed is:

1. A benzoyl amide of formula (I) and/or a salt thereof

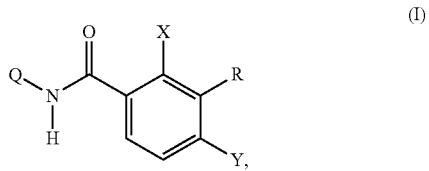

in which the substituents are defined as follows:
Q is a Q1, Q2, Q3 or Q4 radical,

R is —CH═N—OR$^1$, —CH$_2$—O—N═CR$^2$R$^3$,

X is nitro, halogen, cyano, formyl, thiocyanato, (C$_1$-C$_6$)-alkyl, halo-(C$_1$-C$_6$)-alkyl, (C$_2$-C$_6$)-alkenyl, halo-(C$_2$-C$_6$)-alkenyl, (C$_2$-C$_6$)-alkynyl, halo-(C$_3$-C$_6$)-alkynyl, (C$_3$-C$_6$)-cycloalkyl, halo-(C$_3$-C$_6$)-cycloalkyl, (C$_3$-C$_6$)-cycloalkyl-(C$_1$-C$_6$)-alkyl, halo-(C$_3$-C$_6$)-cycloalkyl-(C$_1$-C$_6$)-alkyl, COR$^7$, COOR$^7$, OCOOR$^8$, NR$^7$COOR$^8$, C(O)N(R$^7$)$_2$, NR$^7$C(O)N(R$^7$)$_2$, OC(O)N(R$^7$)$_2$, C(O)NR$^7$OR$^7$, OR$^7$, OCOR$^7$, OSO$_2$R$^8$, S(O)$_n$R$^8$, SO$_2$OR$^7$, SO$_2$N(R$^7$)$_2$, NR$^7$SO$_2$R$^8$, NR$^7$OR$^7$, (C$_1$-C$_6$)-alkyl-S(O)$_n$R$^8$, (C$_1$-C$_6$)-alkyl-OR$^7$, (C$_1$-C$_6$)-alkyl-OCOR$^7$, ($C_1$-$C_6$)-alkyl-OSO$_2$R$^8$, ($C_1$-$C_6$)-alkyl-CO$_2$R$^7$, ($C_1$-$C_6$)-alkyl-SO$_2$OR$^8$, ($C_1$-$C_6$)-alkyl-CON(R$^7$)$_2$, ($C_1$-$C_6$)-alkyl-SO$_2$N(R$^7$)$_2$, ($C_1$-$C_6$)-alkyl-NR$^7$COR$^7$, ($C_1$-$C_6$)-alkyl-NR$^7$SO$_2$R$^8$, N(R$^7$)$_2$, P(O)(OR$^9$)$_2$, CH$_2$P(O)(OR$^9$)$_2$, heteroaryl, heterocyclyl, phenyl, ($C_1$-$C_6$)-alkyl-heteroaryl or ($C_1$-$C_6$)-alkyl-heterocyclyl, where the five last-mentioned radicals are each substituted by s radicals from the group consisting of halogen, nitro, cyano, ($C_1$-$C_6$)-alkyl, halo-($C_1$-$C_6$)-alkyl, S(O)$_n$-($C_1$-$C_6$)-alkyl, ($C_1$-$C_6$)-alkoxy and halo-($C_1$-$C_6$)-alkoxy, and where heterocyclyl carries n oxo groups, Y is nitro, halogen, cyano, formyl, thiocyanato, ($C_1$-$C_6$)-alkyl, halo-($C_1$-$C_6$)-alkyl, ($C_2$-$C_6$)-alkenyl, halo-($C_2$-$C_6$)-alkenyl, ($C_2$-$C_6$)-alkynyl, halo-($C_2$-$C_6$)-alkynyl, ($C_3$-$C_6$)-cycloalkyl, halo-($C_3$-$C_6$)-cycloalkyl, ($C_3$-$C_6$)-cycloalkyl-($C_1$-$C_6$)-alkyl, halo-($C_3$-$C_6$)-cycloalkyl-($C_1$-$C_6$)-alkyl, COR$^7$, COOR$^7$, OCOOR$^8$, NR$^1$COOR$^8$, C(O)N(R$^7$)$_2$, NR$^7$C(O)N(R$^7$)$_2$, OC(O)N(R$^7$)$_2$, C(O)NR$^7$OR$^7$, OR$^7$, OSO$_2$R$^8$, S(O)$_n$R$^8$, SO$_2$OR$^8$, SO$_2$N(R$^7$)$_2$, NR$^7$SO$_2$R$^8$, NR$^7$COR$^7$, ($C_1$-$C_6$)-alkyl-S(O)$_n$R$^8$, ($C_1$-$C_6$)-alkyl-OR$^7$, ($C_1$-$C_6$)-alkyl-OCOR$^7$, ($C_1$-$C_6$)-alkyl-OSO$_2$R$^8$, ($C_1$-$C_6$)-alkyl-CO$_2$R$^7$, ($C_1$-$C_6$)-alkyl-SO$_2$OR$^7$, ($C_1$-$C_6$)-alkyl-CON(R$^7$)$_2$, ($C_1$-$C_6$)-alkyl-SO$_2$N(R$^7$)$_2$, ($C_1$-$C_6$)-alkyl-NR$^7$COR$^7$, ($C_1$-$C_6$)-alkyl-NR$^7$SO$_2$R$^8$, N(R$^7$)$_2$, P(O)(OR$^9$)$_2$, heteroaryl, heterocyclyl or phenyl, where the three last-mentioned radicals are each substituted by s radicals from the group consisting of halogen, nitro, cyano, ($C_1$-$C_6$)-alkyl, halo-($C_1$-$C_6$)-alkyl, ($C_3$-$C_6$)-cycloalkyl, S(O)$_n$-($C_1$-$C_6$)-alkyl, ($C_1$-$C_6$)-alkoxy and halo-($C_1$-$C_6$)-alkoxy, and where heterocyclyl carries n oxo groups, R$^1$ is hydrogen, ($C_1$-$C_6$)-alkyl, ($C_2$-$C_6$)-alkenyl, ($C_2$-$C_6$)-alkynyl, ($C_3$-$C_6$)-cycloalkyl, ($C_3$-$C_6$)-cycloalkenyl, ($C_3$-$C_6$)-cycloalkyl-($C_1$-$C_6$)-alkyl, where the six last-mentioned radicals are each substituted by s radicals from the group consisting of cyano, halogen, nitro, thiocyanato, OR$^{10}$, S(O)$_n$R$^{11}$, N(R$^{10}$)$_2$, NR$^{10}$OR$^{10}$, COR$^{10}$, OCOR$^{10}$, SCOR$^{11}$, NR$^{10}$COR$^{10}$, NR$^{10}$SO$_2$R$^{11}$, CO$_2$R$^{10}$, COSR$^{11}$, CON(R$^{10}$)$_2$ and ($C_1$-$C_4$)-alkoxy-($C_2$-$C_6$)-alkoxycarbonyl, or R$^1$ is phenyl, phenyl-($C_1$-$C_6$)-alkyl, heteroaryl, ($C_1$-$C_6$)-alkyl-heteroaryl, heterocyclyl, ($C_1$-$C_6$)-alkyl-heterocyclyl, ($C_1$-$C_6$)-alkyl-O-heteroaryl, ($C_1$-$C_6$)-alkyl-O-heterocyclyl, ($C_1$-$C_6$)-alkyl-NR$^{10}$-heteroaryl, ($C_1$-$C_6$)-alkyl-NR$^{11}$-heterocyclyl, where the ten last-mentioned radicals are each substituted by s radicals from the group consisting of cyano, halogen, nitro, thiocyanato, ($C_1$-$C_6$)-alkyl, halo-($C_1$-$C_6$)-alkyl, OR$^{10}$, S(O)$_n$R$^{11}$, N(R$^{10}$)$_2$, NR$^{10}$OR$^{10}$, COR$^{10}$, OCOR$^{10}$, SCOR$^{11}$, NR$^{10}$COR$^{10}$, NR$^{10}$SO$_2$R$^{11}$, CO$_2$R$^{10}$, COSR$^{11}$, CON(R$^{10}$)$_2$ and ($C_1$-$C_4$)-alkoxy-($C_2$-$C_6$)-alkoxycarbonyl, and where heterocyclyl carries n oxo groups, R$^2$ and R$^3$ independently of one another are each hydrogen, ($C_1$-$C_6$)-alkyl, halo-($C_1$-$C_6$)-alkyl, ($C_2$-$C_6$)-alkenyl, halo-($C_2$-$C_6$)-alkenyl, ($C_2$-$C_6$)-alkynyl, halo-($C_2$-$C_6$)-alkynyl, ($C_3$-$C_6$)-cycloalkyl, halo-($C_3$-$C_6$)-cycloalkyl, ($C_3$-$C_6$)-cycloalkyl-($C_1$-$C_6$)-alkyl, halo-($C_3$-$C_6$)-cycloalkyl-($C_1$-$C_6$)-alkyl, ($C_1$-$C_6$)-alkoxy-($C_1$-$C_6$)-alkyl, halo-($C_1$-$C_6$)-alkoxy-($C_1$-$C_6$)-alkyl, phenyl, heteroaryl or heterocyclyl, where the three last-mentioned radicals are each substituted by s radicals from the group consisting of cyano, halogen, nitro, thiocyanato, ($C_1$-$C_6$)-alkyl, halo-($C_1$-$C_6$)-alkyl, OR$^{10}$, S(O)$_n$R$^{11}$, N(R$^{10}$)$_2$, NR$^{10}$OR$^{10}$, COR$^{10}$, OCOR$^{10}$, SCOR$^{11}$, NR$^{10}$COR$^{10}$, NR$^{10}$SO$_2$R$^{11}$, CO$_2$R$^{10}$, COSR$^{11}$, CON(R$^{10}$)$_2$ and ($C_1$-$C_4$)-alkoxy-($C_2$-$C_6$)-alkoxycarbonyl, and where heterocyclyl carries n oxo groups, or R$^2$ and R$^3$ together with the atom to which they are attached form a 5- to 6-membered unsaturated, partially saturated or saturated ring which, in addition to carbon atoms, in each case contains n oxygen and sulfur atoms, R$^4$ is ($C_1$-$C_6$)-alkyl, halo-($C_1$-$C_6$)-alkyl, ($C_2$-$C_6$)-alkenyl, halo-($C_2$-$C_6$)-alkenyl, ($C_2$-$C_6$)-alkynyl, halo-($C_2$-$C_6$)-alkynyl, where the six last-mentioned radicals are each substituted by s radicals from the group consisting of nitro, cyano, SiR$^9_3$, PO(OR$^9$)$_3$, S(O)$_n$-($C_1$-$C_6$)-alkyl, ($C_1$-$C_6$)-alkoxy, halo-($C_1$-$C_6$)-alkoxy, N(R$^7$)$_2$, COR$^7$, COOR$^7$, OCOR$^7$, OCO$_2$R$^8$, NR$^7$COR$^7$, NR$^7$SO$_2$R$^8$, ($C_3$-$C_6$)-cycloalkyl, heteroaryl, heterocyclyl, phenyl, W-heteroaryl, W-heterocyclyl, W-phenyl or W-benzyl, where the seven last-mentioned radicals for their part are substituted by s radicals from the group consisting of ($C_1$-$C_6$)-alkyl, halo-($C_1$-$C_6$)-alkyl, ($C_1$-$C_6$)-alkoxy, halo-($C_1$-$C_6$)-alkoxy and halogen, and where heterocyclyl carries n oxo groups, or R$^4$ is ($C_3$-$C_7$)-cycloalkyl, heteroaryl, heterocyclyl or phenyl, where the four last-mentioned radicals are each substituted by s radicals from the group consisting of halogen, nitro, cyano, ($C_1$-$C_6$)-alkyl, halo-($C_1$-$C_6$)-alkyl, ($C_3$-$C_6$)-cycloalkyl, S(O)$_n$-($C_1$-$C_6$)-alkyl, ($C_1$-$C_6$)-alkoxy, halo-($C_1$-$C_6$)-alkoxy and ($C_1$-$C_6$)-alkoxy-($C_1$-$C_4$)-alkyl, R$^5$ is hydrogen, ($C_1$-$C_6$)-alkyl, halo-($C_1$-$C_6$)-alkyl, ($C_2$-$C_6$)-alkenyl, ($C_2$-$C_6$)-haloalkenyl, ($C_2$-$C_6$)-alkynyl, ($C_2$-$C_6$)-haloalkynyl, ($C_3$-$C_7$)-cycloalkyl, ($C_1$-$C_6$)-alkoxy, halo-($C_1$-$C_6$)-alkoxy, ($C_2$-$C_6$)-alkenyloxy, ($C_2$-$C_6$)-alkynyloxy, cyano, nitro, methylsulfenyl, methylsulfinyl, methylsulfonyl, acetylamino, benzoylamino, methoxycarbonyl, ethoxycarbonyl, methoxycarbonylmethyl, ethoxycarbonylmethyl, benzoyl, methylcarbonyl, piperidinylcarbonyl, trifluoromethylcarbonyl, halogen, amino, aminocarbonyl, methylaminocarbonyl, dimethylaminocarbonyl, methoxymethyl, or heteroaryl, heterocyclyl or phenyl, each of which is substituted by s radicals from the group consisting of ($C_1$-$C_6$)-alkyl, halo-($C_1$-$C_6$)-alkyl, ($C_1$-$C_6$)-alkoxy, halo-($C_1$-$C_6$)-alkoxy and halogen, and where heterocyclyl carries n oxo groups, R$^6$ is hydrogen, ($C_1$-$C_6$)-alkyl, R$^7$O—($C_1$-$C_6$)-alkyl, CH$_2$R$^{12}$, ($C_3$-$C_7$)-cycloalkyl, halo-($C_1$-$C_6$)-alkyl, ($C_2$-$C_6$)-alkenyl, halo-($C_2$-$C_6$)-alkenyl, ($C_2$-$C_6$)-alkynyl, halo-($C_2$-$C_6$)-alkynyl, OR$^7$, NHR$^7$, methoxycarbonyl, ethoxycarbonyl, methoxycarbonylmethyl, ethoxycarbonylmethyl, methylcarbonyl, trifluoromethylcarbonyl, dimethylamino, acetylamino, methylsulfenyl, methylsulfinyl, methylsulfonyl, or heteroaryl, heterocyclyl, benzyl or phenyl, each of which is substituted by s radicals from the group consisting of halogen, nitro, cyano, ($C_1$-$C_6$)-alkyl, halo-($C_1$-$C_6$)-alkyl, ($C_3$-$C_6$)-cycloalkyl, S(O)$_n$-($C_1$-$C_6$)-alkyl, ($C_1$-$C_6$)-alkoxy, halo-($C_1$-$C_6$)-alkoxy and ($C_1$-$C_6$)-alkoxy-($C_1$-$C_4$)-alkyl, where heterocyclyl carries n oxo groups, R$^7$ is hydrogen, ($C_1$-$C_6$)-alkyl, ($C_2$-$C_6$)-alkenyl, ($C_2$-$C_6$)-alkynyl, ($C_3$-$C_6$)-cycloalkyl, ($C_3$-$C_6$)-cycloalkenyl, ($C_3$-$C_6$)-cycloalkyl-($C_1$-$C_6$)-alkyl, phenyl, phenyl-($C_1$-$C_6$)-alkyl, heteroaryl, ($C_1$-$C_6$)-alkylheteroaryl, heterocyclyl, ($C_1$-$C_6$)-alkylheterocyclyl, ($C_1$-$C_6$)-alkyl-O-heteroaryl, ($C_1$-$C_6$)-alkyl-O-heterocyclyl, ($C_1$-$C_6$)-alkyl-NR$^{10}$-heteroaryl, ($C_1$-$C_6$)-alkyl-NR$^{10}$-heterocyclyl, where the 16 last-mentioned radicals are each substituted by s radicals from the group consisting of cyano, halogen, nitro, thiocyanato, OR$^{10}$, S(O)$_n$R$^{11}$, N(R$^{10}$)$_2$, NR$^{10}$OR$^{10}$, COR$^{10}$, OCOR$^{10}$, SCOR$^{11}$, NR$^{10}$COR$^{10}$, NR$^{10}$SO$_2$R$^{11}$, CO$_2$R$^{11}$, COSR$^{11}$, CON(R$^{10}$)$_2$ and ($C_1$-$C_4$)-alkoxy-($C_2$-$C_6$)-alkoxycarbonyl, and where heterocyclyl carries n oxo groups, R⁸ is $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkenyl, $(C_3-C_6)$-cycloalkyl-$(C_1-C_6)$-alkyl, phenyl, phenyl-$(C_1-C_6)$-alkyl, heteroaryl, $(C_1-C_6)$-alkyl-heteroaryl, heterocyclyl, $(C_1-C_6)$-alkyl-heterocyclyl, $(C_1-C_6)$-alkyl-O-heteroaryl, $(C_1-C_6)$-alkyl-O-heterocyclyl, $(C_1-C_6)$-alkyl-NR$^{10}$-heteroaryl, $(C_1-C_6)$-alkyl-NR$^{10}$-heterocyclyl, where the 16 last-mentioned radicals are each substituted by s radicals from the group consisting of cyano, halogen, nitro, thiocyanato, OR$^{10}$, S(O)$_n$R$^{11}$, N(R$^{10}$)$_2$, NR$^{10}$OR$^{10}$, COR$^{10}$, OCOR$^{10}$, SCOR$^{11}$, NR$^{10}$COR$^{10}$, NR$^{10}$SO$_2$R$^{11}$, CO$_2$R$^{10}$, COSR$^{11}$, CON(R$^{10}$)$_2$ and $(C_1-C_4)$-alkoxy-$(C_2-C_6)$-alkoxycarbonyl, and where heterocyclyl carries n oxo groups, R⁹ is methyl or ethyl, R¹⁰ is hydrogen, $(C_1-C_6)$-alkyl, halo-$(C_1-C_6)$-alkyl $(C_2-C_6)$-alkenyl, $(C_2-C_6)$-alkynyl, $(C_3-C_6)$-cycloalkyl or $(C_3-C_6)$-cycloalkyl-$(C_1-C_6)$-alkyl, R¹¹ is $(C_1-C_6)$-alkyl, $(C_2-C_6)$-alkenyl or $(C_2-C_6)$-alkynyl, R¹² is acetoxy, acetamido, N-methylacetamido, benzoyloxy, benzamido, N-methylbenzamido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, $(C_1-C_6)$-alkoxy, $(C_3-C_6)$-cycloalkyl, or heteroaryl, heterocyclyl or phenyl each substituted by s radicals from the group consisting of methyl, ethyl, methoxy, trifluoromethyl and halogen, R¹³ is $(C_1-C_6)$-alkyl, $(C_2-C_6)$-alkenyl or $(C_2-C_6)$-alkynyl, phenyl W is O, S, or NR¹³, n is 0, 1 or 2, s is 0, 1, 2 or 3.

2. The benzoylamide and/or salt as claimed in claim 1, in which

Q is a Q1, Q2, Q3 or Q4 radical,

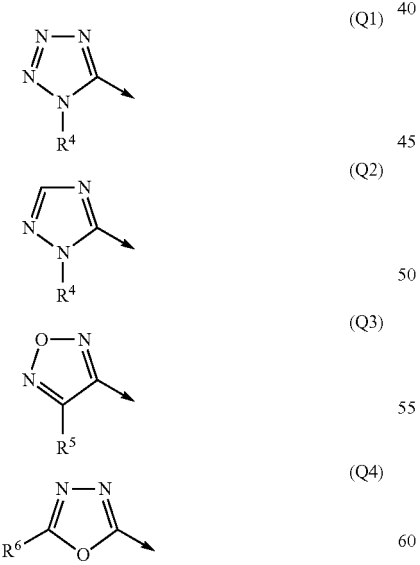

R is —CH═N—OR¹, —CH₂—O—N═CR²R³,

X is nitro, halogen, cyano, $(C_1-C_6)$-alkyl, halo-$(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl, OR⁷, S(O)$_n$R⁸, SO₂N(R⁷)₂, NR⁷SO₂R⁸, $(C_1-C_6)$-alkyl-S(O)$_n$R⁸, $(C_1-C_6)$-alkyl-OR⁷, $(C_1-C_6)$-alkyl-CO₂R⁷, $(C_1-C_6)$-alkyl-CON(R⁷)₂, $(C_1-C_6)$-alkyl-SO₂N(R⁷)₂, $(C_1-C_6)$-alkyl-NR⁷COR⁷, $(C_1-C_6)$-alkyl-NR⁷SO₂R⁸, N(R⁷)₂, P(O)(OR⁹)₂, CH₂P(O)(OR⁹)₂, heteroaryl, heterocyclyl, phenyl, $(C_1-C_6)$-alkyl-heteroaryl or $(C_1-C_6)$-alkyl-heterocyclyl, where the five last-mentioned radicals are each substituted by s radicals from the group consisting of halogen, nitro, cyano, $(C_1-C_6)$-alkyl, halo-$(C_1-C_6)$-alkyl, S(O)$_n$-$(C_1-C_6)$-alkyl, $(C_1-C_6)$-alkoxy and halo-$(C_1-C_6)$-alkoxy, and where heterocyclyl carries n oxo groups, Y is nitro, halogen, cyano, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, OR⁷, OSO₂R⁸, S(O)$_n$R⁸, SO₂OR⁸, SO₂N(R⁷)₂, NR⁷SO₂R⁸, N(R⁷)₂, P(O)(OR⁹)₂, heteroaryl, heterocyclyl or phenyl, where the three last-mentioned radicals are each substituted by s radicals from the group consisting of halogen, nitro, cyano, $(C_1-C_6)$-alkyl, halo-$(C_1-C_6)$-alkyl, $(C_3-C_6)$-cycloalkyl, S(O)$_n$-$(C_1-C_6)$-Alkyl, $(C_1-C_6)$-alkoxy and halo-$(C_1-C_6)$-alkoxy, and where heterocyclyl carries n oxo groups, R¹ is hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl, where the five last-mentioned radicals are each substituted by s radicals from the group consisting of cyano, halogen, nitro, OR$^{10}$, S(O)$_n$R$^{11}$, COR$^{10}$, OCOR$^{10}$, NR$^{10}$COR$^{10}$, NR$^{10}$SO$_2$R$^{11}$, CO$_2$R$^{10}$, CON(R$^{10}$)$_2$ and $(C_1-C_4)$-alkoxy-$(C_2-C_6)$-alkoxycarbonyl, or R¹ is phenyl, phenyl-$(C_1-C_6)$-alkyl, heteroaryl, $(C_1-C_6)$-alkyl-heteroaryl, heterocyclyl, $(C_1-C_6)$-alkyl-heterocyclyl, $(C_1-C_6)$-alkyl-O-heteroaryl, $(C_1-C_6)$-alkyl-O-heterocyclyl, $(C_1-C_6)$-alkyl-NR$^{10}$-heteroaryl or $(C_1-C_6)$-alkyl-NR$^{10}$-heterocyclyl, where the ten last-mentioned radicals are each substituted by s radicals from the group consisting of cyano, halogen, nitro, thiocyanato, $(C_1-C_6)$-alkyl, halo-$(C_1-C_6)$-alkyl, OR$^{10}$, S(O)$_n$R$^{11}$, N(R$^{10}$)$_2$, COR$^{10}$, OCOR$^{10}$, NR$^{10}$COR$^{10}$, NR$^{10}$SO$_2$R$^{11}$, CO$_2$R$^{10}$, CON(R$^{10}$)$_2$ and $(C_1-C_4)$-alkoxy-$(C_2-C_6)$-alkoxycarbonyl, and where heterocyclyl carries n oxo groups, R² and R³ independently of one another are each hydrogen, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, $(C_3-C_6)$-cycloalkyl-$(C_1-C_6)$-alkyl, $(C_1-C_6)$-alkoxy-$(C_1-C_6)$-alkyl, halo-$(C_1-C_6)$-alkoxy-$(C_1-C_6)$-alkyl, phenyl, heteroaryl or heterocyclyl, where the three last-mentioned radicals are each substituted by s radicals from the group consisting of cyano, halogen, nitro, $(C_1-C_6)$-alkyl, halo-$(C_1-C_6)$-alkyl, OR$^{10}$, S(O)$_n$R$^{11}$, N(R$^{10}$)$_2$, COR$^{10}$, NR$^{10}$COR$^{10}$, NR$^{10}$SO$_2$R$^{11}$, CO$_2$R$^{10}$, CON(R$^{10}$)$_2$ and $(C_1-C_4)$-alkoxy-$(C_2-C_6)$-alkoxycarbonyl, and where heterocyclyl carries n oxo groups, or R² and R³ together with the atom to which they are attached form a 5- to 6-membered unsaturated, partially saturated or saturated ring which, in addition to carbon atoms, in each case contains n oxygen and sulfur atoms, R⁴ is $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, where the six last-mentioned radicals are each substituted by s radicals from the group consisting of nitro, cyano, S(O)$_n$—$(C_1-C_6)$-alkyl, $(C_1-C_6)$-alkoxy, halo-$(C_1-C_6)$-alkoxy, COOR⁷, NR⁷COR⁷, NR⁷SO₂R⁸, $(C_3-C_6)$-cycloalkyl, heteroaryl, heterocyclyl, phenyl, W-heteroaryl, W-heterocyclyl, W-phenyl and W-benzyl, where the 7 last-mentioned radicals for their part are substituted by s radicals from the group consisting of (C₁-C₆)-alkyl, halo-(C₁-C₆)-alkyl, (C₁-C₆)-alkoxy, halo-(C₁-C₆)-alkoxy and halogen, and where heterocyclyl carries n oxo groups, or R⁴ is (C₃-C₇)-cycloalkyl, heteroaryl, heterocyclyl or phenyl, where the four last-mentioned radicals are each substituted by s radicals from the group consisting of halogen, nitro, cyano, (C₁-C₆)-alkyl, halo-(C₁-C₆)-alkyl, (C₃-C₆)-cycloalkyl, S(O)ₙ-(C₁-C₆)-alkyl, (C₁-C₆)-alkoxy, halo-(C₁-C₆)-alkoxy and (C₁-C₆)-alkoxy-(C₁-C₄)-alkyl, R⁵ is hydrogen, (C₁-C₆)-alkyl, halo-(C₁-C₆)-alkyl, (C₂-C₆)-alkenyl, (C₂-C₆)-haloalkenyl, (C₂-C₆)-alkynyl, (C₂-C₆)-haloalkynyl, (C₃-C₇)-cycloalkyl, (C₁-C₆)-alkoxy, halo-(C₁-C₆)-alkoxy, (C₂-C₆)-alkenyloxy, (C₂-C₆)-alkynyloxy, cyano, nitro, methylsulfenyl, methylsulfinyl, methylsulfonyl, acetylamino, methoxycarbonyl, methoxycarbonylmethyl, methylcarbonyl, trifluoromethylcarbonyl, halogen, amino, aminocarbonyl, methylaminocarbonyl, dimethylaminocarbonyl, methoxymethyl, or heteroaryl, heterocyclyl or phenyl, each of which is substituted by s radicals from the group consisting of (C₁-C₆)-alkyl, halo-(C₁-C₆)-alkyl, (C₁-C₆)-alkoxy, halo-(C₁-C₆)-alkoxy and halogen, and where heterocyclyl carries n oxo groups, R⁶ is hydrogen, (C₁-C₆)-alkyl, R⁷O—(C₁-C₆)-alkyl, CH₂R¹², (C₃-C₇)-cycloalkyl, halo-(C₁-C₆)-alkyl, (C₂-C₆)-alkenyl, (C₂-C₆)-alkynyl, OR⁷, NHR⁷, methoxycarbonyl, methoxycarbonylmethyl, methylcarbonyl, trifluoromethylcarbonyl, dimethylamino, acetylamino, methylsulfenyl, methylsulfinyl, methylsulfonyl, or heteroaryl, heterocyclyl, benzyl or phenyl, each of which is substituted by s radicals from the group consisting of halogen, nitro, cyano, (C₁-C₆)-alkyl, halo-(C₁-C₆)-alkyl, (C₃-C₆)-cycloalkyl, S(O)ₙ-(C₁-C₆)-alkyl, (C₁-C₆)-alkoxy, halo-(C₁-C₆)-alkoxy, (C₁-C₆)-alkoxy-(C₁-C₄)-alkyl, and where heterocyclyl carries n oxo groups, R⁷ is hydrogen, (C₁-C₆)-alkyl, (C₂-C₆)-alkenyl, (C₂-C₆)-alkynyl, (C₃-C₆)-cycloalkyl, (C₃-C₆)-cycloalkenyl, (C₃-C₆)-cycloalkyl-(C₁-C₆)-alkyl, phenyl, heteroaryl, heterocyclyl, where the nine last-mentioned radicals are each substituted by s radicals from the group consisting of cyano, halogen, nitro, OR¹⁰, S(O)ₙR¹¹, N(R¹⁰)₂, NR¹⁰SO₂R¹¹, CO₂R¹⁰, CON(R¹⁰)₂ and (C₁-C₄)-alkoxy-(C₂-C₆)-alkoxycarbonyl, and where heterocyclyl carries n oxo groups, R⁸ is (C₁-C₆)-alkyl, (C₂-C₆)-alkenyl, (C₂-C₆)-alkynyl, (C₃-C₆)-cycloalkyl, (C₃-C₆)-cycloalkenyl, (C₃-C₆)-cycloalkyl-(C₁-C₆)-alkyl, phenyl, heteroaryl, heterocyclyl, where the nine last-mentioned radicals are each substituted by s radicals from the group consisting of cyano, halogen, nitro, OR¹⁰, S(O)ₙR¹¹, N(R¹⁰)₂, NR¹⁰SO₂R¹¹, CO₂R¹⁰, CON(R¹⁰)₂ and (C₁-C₄)-alkoxy-(C₂-C₆)-alkoxycarbonyl, and where heterocyclyl carries n oxo groups, R⁹ is methyl or ethyl, R¹⁰ is hydrogen, (C₁-C₆)-alkyl, halo-(C₁-C₆)-alkyl (C₂-C₆)-alkenyl, (C₂-C₆)-alkynyl, (C₃-C₆)-cycloalkyl or (C₃-C₆)-cycloalkyl-(C₁-C₆)-alkyl, R¹¹ is (C₁-C₆)-alkyl, (C₂-C₆)-alkenyl or (C₂-C₆)-alkynyl, R¹² is acetoxy, acetamido, N-methylacetamido, benzoyloxy, benzamido, N-methylbenzamido, methoxycarbonyl, ethoxycarbonyl, benzoyl, methylcarbonyl, trifluoromethylcarbonyl, aminocarbonyl, methylaminocarbonyl, dimethylaminocarbonyl, (C₁-C₆)-alkoxy, (C₃-C₆)-cycloalkyl, or heteroaryl, heterocyclyl or phenyl each substituted by s radicals from the group consisting of methyl, methoxy, trifluoromethyl and halogen, R¹³ is (C₁-C₆)-alkyl, W is O, S or NR¹³, n is 0, 1 or 2;

s is 0, 1, 2 or 3.

3. The benzoylamide and/or salt as claimed in claim 1, in which

Q is a Q1 or Q2 radical,

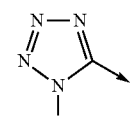

(Q1)

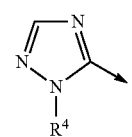

(Q2)

R is —CH═N—OR¹, —CH₂—O—N═CR²R³,

X is nitro, halogen, (C₁-C₆)-alkyl, halo-(C₁-C₆)-alkyl, S(O)ₙR⁸, (C₁-C₆)-alkyl-S(O)ₙR⁸, (C₁-C₆)-alkyl-OR⁷, (C₁-C₆)-alkyl-SO₂N(R⁷)₂ or (C₁-C₆)-alkyl-NR⁷SO₂R⁸, Y is nitro, halogen, halo-(C₁-C₆)-alkyl or S(O)ₙR⁸, R¹ is hydrogen, (C₁-C₆)-alkyl, (C₂-C₆)-alkenyl, (C₂-C₆)-alkynyl, (C₃-C₆)-cycloalkyl or (C₃-C₆)-cycloalkyl-(C₁-C₆)-alkyl, where the five last-mentioned radicals are each substituted by s radicals from the group consisting of cyano, halogen, OR¹⁰ and S(O)ₙR¹¹, R² and R³ independently of one another are each hydrogen, (C₁-C₆)-alkyl, halo-(C₁-C₆)-alkyl, (C₂-C₆)-alkenyl, (C₂-C₆)-alkynyl, (C₁-C₆)-alkoxy-(C₁-C₆)-alkyl or halo-(C₁-C₆)-alkoxy-(C₁-C₆)-alkyl, R⁴ is (C₁-C₆)-alkyl, (C₂-C₆)-alkenyl or (C₂-C₆)-alkynyl, where these three radicals are each substituted by s radicals (C₁-C₆)-alkoxy, R⁵ is (C₁-C₆)-alkyl, (C₂-C₆)-alkenyl, (C₂-C₆)-alkynyl, (C₃-C₇)-cycloalkyl, (C₁-C₆)-alkoxy, (C₂-C₆)-alkenyloxy, (C₂-C₆)-alkynyloxy, acetylamino, halogen or methoxymethyl, R⁶ is (C₁-C₆)-alkyl, R⁷O-(C₁-C₆)-alkyl, CH₂R¹², (C₃-C₇)-cycloalkyl, (C₂-C₆)-alkenyl or (C₂-C₆)-alkynyl, R⁷ is hydrogen, (C₁-C₆)-alkyl, (C₂-C₆)-alkenyl, (C₂-C₆)-alkynyl, (C₃-C₆)-cycloalkyl or (C₃-C₆)-cycloalkyl-(C₁-C₆)-alkyl, R⁸ is (C₁-C₆)-alkyl, (C₂-C₆)-alkenyl, (C₂-C₆)-alkynyl, (C₃-C₆)-cycloalkyl, (C₃-C₆)-cycloalkenyl or (C₃-C₆)-cycloalkyl-(C₁-C₆)-alkyl, R⁹ is methyl or ethyl, R¹⁰ is hydrogen, (C₁-C₆)-alkyl, (C₂-C₆)-alkenyl, (C₂-C₆)-alkynyl, (C₃-C₆)-cycloalkyl or (C₃-C₆)-cycloalkyl-(C₁-C₆)-alkyl, R¹¹ is (C₁-C₆)-alkyl, (C₂-C₆)-alkenyl or (C₂-C₆)-alkynyl, R¹² is acetoxy, acetamido or (C₃-C₆)-cycloalkyl, R¹³ is (C₁-C₆)-alkyl, W is O, S or NR¹³, n is 0, 1 or 2;

s is 0, 1, 2 or 3.

4. A herbicidal composition comprising a herbicidally effective amount of at least one compound of formula (I) and/or salt as claimed in claim 1.

5. The herbicidal composition as claimed in claim 4 in a mixture with one or more formulation auxiliaries.

6. The herbicidal composition as claimed in claim 4, comprising at least one further pesticidally active substance from the group of insecticides, acaricides, herbicides, fungicides, safeners and growth regulators.

7. The herbicidal composition as claimed in claim 6, comprising a safener.

8. The herbicidal composition as claimed in claim 7, comprising cyprosulfamide, cloquintocet-mexyl, mefenpyr-diethyl or isoxadifen-ethyl.

9. The herbicidal composition as claimed in claim 6, comprising a further herbicide.

10. A method for controlling an unwanted plant, comprising applying an effective amount of at least one compound of formula (I) and/or salt as claimed in claim 1 to a plant and/or a site of unwanted plant growth.

* * * * *